US009868747B2

(12) United States Patent
Li et al.

(10) Patent No.: US 9,868,747 B2
(45) Date of Patent: Jan. 16, 2018

(54) MARINOPYRROLE DERIVATIVES AND METHODS OF MAKING AND USING SAME

(71) Applicants: H. LEE MOFFITT CANCER CENTER AND RESEARCH INSTITUTE, INC., Tampa, FL (US); CHONGQING ZEIN PHARMACEUTICAL CO., LTD, Chongqing (CN)

(72) Inventors: Rongshi Li, Omaha, NE (US); Said Sebti, Tampa, FL (US); Yan Liu, Omaha, NE (US); Yong Qin, Chongqing (CN); Hao Song, Chengdu (CN); Chunwei Cheng, Zhumadian (CN)

(73) Assignees: H. LEE MOFFITT CANCER CENTER AND RESEARCH INSTITUTE, INC., Tampa, FL (US); CHONGQING ZEIN PHARMACEUTICAL CO., LTD, Chongping (CN)

(*) Notice: Subject to any disclaimer, the term of this patent is extended or adjusted under 35 U.S.C. 154(b) by 0 days.

(21) Appl. No.: 15/118,975

(22) PCT Filed: Feb. 18, 2015

(86) PCT No.: PCT/US2015/016336
§ 371 (c)(1),
(2) Date: Aug. 15, 2016

(87) PCT Pub. No.: WO2015/126912
PCT Pub. Date: Aug. 27, 2015

(65) Prior Publication Data
US 2017/0050981 A1 Feb. 23, 2017

Related U.S. Application Data

(60) Provisional application No. 61/941,374, filed on Feb. 18, 2014, provisional application No. 61/981,357, filed on Apr. 18, 2014.

(51) Int. Cl.
| | | |
|---|---|---|
| A01N 43/36 | (2006.01) |
| A01N 43/647 | (2006.01) |
| A01N 47/02 | (2006.01) |
| A61K 45/06 | (2006.01) |
| A61K 31/553 | (2006.01) |
| A61K 31/662 | (2006.01) |
| A61K 31/407 | (2006.01) |
| C07D 498/14 | (2006.01) |
| C07D 403/14 | (2006.01) |
| C07D 403/04 | (2006.01) |
| A61K 31/4192 | (2006.01) |
| A61N 5/10 | (2006.01) |
| C07F 9/6561 | (2006.01) |

(52) U.S. Cl.
CPC ........... *C07D 498/14* (2013.01); *A01N 43/36* (2013.01); *A01N 43/647* (2013.01); *A01N 47/02* (2013.01); *A61K 31/407* (2013.01); *A61K 31/4192* (2013.01); *A61K 31/553* (2013.01); *A61K 31/662* (2013.01); *A61K 45/06* (2013.01); *A61N 5/10* (2013.01); *C07D 403/04* (2013.01); *C07D 403/14* (2013.01); *C07F 9/6561* (2013.01)

(58) Field of Classification Search
CPC ...... A01N 43/36; A01N 43/647; A01N 47/02; A61K 45/06; A61K 31/353; A61K 31/662; A61K 31/407; C07D 498/14; C07D 403/14; C07D 403/04
See application file for complete search history.

(56) References Cited

U.S. PATENT DOCUMENTS

2010/0305092 A1    12/2010   Quattropani et al.

FOREIGN PATENT DOCUMENTS

| WO | 2013024048 A1 | 2/2013 |
| WO | 2013158197 A1 | 10/2013 |

OTHER PUBLICATIONS

Produrg, 2017, https://en.wikipedia.org/wiki/Prodrug.*
Bladder, 2017, http://www.webmd.com/cancer/bladder-cancer/bladder-cancer-prevention.*
Brain, 2017, http://www.medicinenet.com/brain_cancer/page10.htm.*
BreastCancer, 2017, https://www.cancer.org/cancer/breast-cancer/risk-and-prevention.html.*
Li et al., 2014, caplus an 2014:2035034.*
International Search Report and Written Opinion issued in related International Application No. PCT/US15/16336, dated Apr. 30, 2015.
International Preliminary Report on Patentability Opinion issued in related International Application No. PCT/US15/16336, dated Sep. 1, 2016.
Abulwerdi, et al., "A novel small-molecule inhibitor of Mcl-1 blocks pancreatic cancer growth in vitro and in vivo", Mol. Cancer Ther. 2013, published OnlineFirst Sep. 9, 2013. doi:10.1158/1535-7163.MCT-12-0767.
Balasis, et al., "Combination of farnesyltransferase and Akt inhibitors is synergistic in breast cancer cells and causes significant breast tumor regression in ErbB2 transgenic mice", Clin. Cancer Res. 2011, 17, 2852-2862.

(Continued)

*Primary Examiner* — Sun Jae Yoo
(74) *Attorney, Agent, or Firm* — Meunier Carlin & Curfman LLC

(57) ABSTRACT

Marinopyrrole derivatives and methods for their synthesis and use are described herein. Novel cyclic and symmetric marinopyrroles with triazole substituents having antibacterial activity against resistant bacterial strains, such as MRSA are introduced. Also provided are methods of using the compounds for treating or preventing cancer and/or microbial infections.

20 Claims, 7 Drawing Sheets

(56) References Cited

OTHER PUBLICATIONS

Berge, et al., "Pharmaceuticals Salts",J. Pharm. Sci., 1977, 66, p. 1-19.
Beroukhim, et al., "The landscape of somatic copy-number alteration across human cancers", Nature 2010,463, 899-905.
Chen, et al., "Mcl-1 Down-regulation Potentiates ABT-737 Lethality by Cooperatively Inducing Bak Activation and Bax Translocation", Cancer Res 2007, 67, 782-791.
Cheng, et al., "Marinopyrrole Derivatives as Potential Antibiotic Agents against Methicillin-Resistant *Staphylococcus aureus* (II)", Mar. Drugs 2013, 11, 2927-2948.
Cheng, et al., "Racemic marinopyrrole B by total synthesis", Chem. Commun. 2013, 49, 558-560.
Cheng, et al., "Total Synthesis of (+_) -Marinopyrrole A and its library as potential antibiotic and Anticancer Agents", J. Comb. Chem. 2010, 12, 541-547.
Derrick, et al., "The marinopyrroles", Tetrahedron 2013, 69, 5067-5078.
Csizmadia, et al., "Prediction of distribution coefficient from structure. 1. Estimation method", J. Pharm. Sci. 1997, 86, 865-871.
Day, et al., "Structure of the BH3 Domains from the p53-Inducible BH3-Only Proteins Noxa and Puma in Complex with Mcl-1", J. Mol. Biol. 2008, 380, 958-971.
Dixon, et al., "Estimation of pKa for organic oxyacids using calculated atomic charge", J. Comp. Chem. 1993, 14, 1460-1467.
Doi, et al., "Discovery of marinopyrrole A (Maritoclax) as a selective Mcl-1 antagonist that overcomes ABT-737 resistance by binding to and targeting Mcl-1 for proteasomal degradation", J Biol Chem. 2012, 287(13), 10224-10235.
Fire, et al., "Mcl-1—Bim complexes accommodate surprising point mutations via minor structural changes", Protein Science 2010, 19, 507-519.
Friesner, et al., "Extra precision glide: docking and scoring incorporating a model of hydrophobic enclosure for protein-ligand complexes", J. Med. Chem. 2006, 49, 6177-6196.
Friesner, et al., "Glide: A New Approach for Rapid, Accurate Docking and Scoring. 1. Method and Assessment of Docking Accuracy", J. Med. Chem. 2004, 47, 1739-1749.
Gavathiotis, et al., "Direct and selective small-molecule activation of proapoptotic BAX", Nat. Chem. Biol. 2012, 8, 639-645.
Halgren, et al., "Glide: a new approach for rapid, accurate docking and scoring. 2. Enrichment factors in database screening.", J. Med. Chem. 2004, 47, 1750-1759.
Hikita, et al., "The Bcl-xL inhibitor, ABT-737, efficiently induces apoptosis and suppresses growth of hepatoma cells in combination with sorafenib", Hepatology 2010 52, 1310-1321.
Hughes, et al., "Structures, reactivities, and antibiotic properties of the marinopyrroles A-F", J. Org. Chem. 2010, 75, 3240-3250.
Hughes, et al., "The marinopyrroles, antibiotics of an unprecedented structure class from a marine", *Streptomyces* sp. Org. Lett. 2008, 10, 629-631.
Kanakis, et al., "Total synthesis of (±)-marinopyrrole A via copper-mediated N-arylation", Org. Lett. 2010, 12, 4872-4875.
Kazi, et al., "The BH3 alpha-helical mimic BH3-M6 disrupts Bcl-X(L), Bcl-2, and MCL-1 protein-protein interactions with Bax, Bak, Bad, or Bim and induces apoptosis in a Bax- and Bim-dependent manner", J Biol Chem 2011, 286, 9382-9392.
Kim, et al. "Structure-activity relationships of pyridoxal phosphate derivatives as potent and selective antagonists of P2X1 receptors", J. Med. Chem. 2001, 44, 340-349.
Kolb, et al., "Click Chemistry: Diverse Chemical Function from a Few Good Reactions", Angew. Chem. Int. Ed. Engl. 2001, 40, 2004-2021.
Konopleva, et al., "Mechanisms of apoptosis sensitivity and resistance to the BH3 mimetic ABT-737 in acute myeloid leukemia", Cancer Cell 2006, 10, 375-388.

Kuhn, et al., "Intramolecular hydrogen bonding in medicinal chemistry", J. Med. Chem. 2010, 53, 2601-2611.
Lin, et al., "'Seed' analysis of off-target siRNAs reveals an essential role of Mcl-1 in resistance to the small-molecule Bcl-2/Bcl-XL inhibitor ABT-737", Oncogene 2007, 26, 3972-3979.
Lipinski, et al., "Experimental and computational approaches to estimate solubility and permeability in drug discovery and development settings", Drug Deliv. Rev. 23, 1997, 3-25.
Liptak, et al., "Absolute pK(a) determinations for substituted phenols", J. Am. Chem. Soc. 2002, 124, 6421-6427.
Liu, et al., "Marinopyrrole Derivatives as Potential Antibiotic Agents against Methicillin-Resistant *Staphylococcus aureus* (I)", Marine drugs 10, 953-962, 2012.
Liu, et al., "Marinopyrrole Derivatives as Potential Antibiotic Agents against Methicillin-Resistant *Staphylococcus aureus* (II)", Mar. Drugs 2013, 11, 2927-2948; doi:10.3390/md11082927.
Nicolaou, et al., "Total Synthesis and biological evaluation of marinopyrrole A and analogs", Tetrahedron Lett. 2011, 52, 2041-2043.
Oltersdorf, et al., "An inhibitor of Bcl-2 family proteins induces regression of solid tumours", Nature 2005, 435, 677-681.
Pan, et al., "Optimization of synthetic method of marinopyrrole A derivatives", Chem. J. Chinese Universities 2012, 33, 1476-1480.
Petrakis, et al., "Palladium-catalyzed substituions of triflates derivaed from tyrosine-containing peptides and simpler hydroxyarenens forming 4-(diethoxyphosphinyl)phenylalanines and diethyl aryphosphonates", J. Am. Chem. Soc. 1987, 109, 2831-2833.
Reed, et al., "BCL-2 Family Proteins: Strategies for Overcoming Chemoresistance in Cancer", Adv Pharmacol 1997, 41, 501-532.
Reed, et al., "BCL-2 family proteins: regulators of cell death involved in the pathogenesis of cancer and resistance to therapy", J Cell Biochem. 1996, 60: 23-32.
Sattler, et al., "Structure of Bcl-xL-Bak Peptide Complex: Recognition Between Regulators of Apoptosis", Science 1997, 275, 983-986.
Tahir, et al., "Influence of Bcl-2 Family Members on the Cellular Response of Small-Cell Lung Cancer Cell Lines to ABT-737", Cancer Res 2007, 67, 1176-1183.
Toyoizumi, et al., "Combined therapy with chemotherapeutic agents and herpes simplex virus type IICP34.5 mutant (HSV-1716) in human non-small cell lung cancer", Human Gene Therapy 10(18), 1999, 3013-3029.
Tse, et al., "ABT-263: A Potent and Orally Bioavailable Bcl-2 Family Inhibitor", Cancer Res 2008, 68, 3421-3428.
Uyanik, et al., "Catalytic diastereoselective polycyclization of homo(polyprenyl)arene analogues bearing terminal siloxyvinyl groups", Org. Lett. 2006, 8, 5649-5652.
Van Delft, et al., "The BH3 mimetic ABT-737 targets selective Bcl-2 proteins and efficiently induces apoptosis via Bak/Bax if Mcl-1 is neutralized", Cancer Cell 2006, 10, 389-399.
Vogler, et al., "Bcl-2 inhibitors: small molecules with a big impact on cancer therapy", Cell Death Differ 2009,16, 360-367.
Vranken, et al., "The CCPN data model for NMR spectroscopy: development of a software pipeline", Proteins. 2005, 59, 687-696.
Willis, et al., "Proapoptotic Bak is sequestered by Mcl-1 and Bcl-xL, but not Bcl-2, until displaced by BH3-only proteins", Genes Dev 2005, 19, 1294-1305.
Yamanaka, et al., "Flavoenzyme-catalyzed atropo-selective N,C-bipyrrole homocoupling in marinopyrrole biosynthesis", J. Am. Chem. Soc. 2012, 134, 12434-12437.
Yecies, et al. "Acquired resistance to ABT-737 in lymphoma cells that up-regulate MCL-1 and BFL-1" Blood 2009, 233-304.
Yip, et al., "Bcl-2 family proteins and cancer", Oncogene 2008, 27, 6398-6406.

* cited by examiner

| Compd | Substituent | Mcl-1/Bim [a] | Bcl-xL/Bim [a] | pKa 1 [b] | pKa 2 [b] | pKa 3/4 [b] | pKa 5/6 [b] | Clog p [b] |
|---|---|---|---|---|---|---|---|---|
| (±)-1 | R = H | 8.9 ± 1.0 | 16.4 ± 3.3 | 7.8 | 8.4 | - | - | 5.6 |
| (+)-1 | R = H | 12.7 ± 1.0 | 19.7 ± 3.6 | 7.8 | 8.4 | - | - | 5.6 |
| (−)-1 | R = H | 12.5 ± 1.4 | 12.0 ± 2.8 | 7.8 | 8.4 | - | - | 5.6 |
| 4a | R = COOMe | 16.9 ± 2.3 | > 100 | 7.5 | 8.1 | - | - | 5.9 |
| 5a | R = PO(EtO)$_2$ | 7.7 ± 2.2 | > 100 | 6.8 | 7.4 | - | - | 6.7 |
| 7a | R = COOH | 61.4 ± 7.6 | > 100 | 7.8 | 8.4 | 3.8 | 3.2 | 4.6 |
| 8a | R = PO(OH)$_2$ | 10.9 ± 3.1 | 27.3 ± 7.2 | 7.8 | 8.1 | 0.7/5.5 [c] | 1.0/5.8 [c] | 2.4 |
| 9 | Tetrabromo-(±)-1 | 4.5 ± 0.9 | 7.3 ± 0.9 | 7.8 | 8.4 | - | - | 6.7 |

[a] IC$_{50}$ in µM (Average ± SEM, n ≥ 3); [b] Calculated using ChemAxon Software Version 5.12.3; [c] pKa values from two hydroxyl groups.

| Compd | Substituent | Mcl-1/Bim a | Bcl-xL/Bim a | pKa 1 c | pKa 2/3 c | pKa 4/5 c | Clog p c |
|---|---|---|---|---|---|---|---|
| 3 | R = OSO₂CF₃ | 1.4 ± 0.3 | 2.3 ± 1.1 | 7.4 | - | - | 7.0 |
| 4 | R = COOMe | 4.3 ± 1.5 | 3.4 ± 0.9 | 7.8 | - | - | 4.7 |
| 5 | R = PO(EtO)₂ | > 100 b | > 100 | 7.1 | - | 7.2 | 5.5 |
| 6 | R = OH | 42.5 ± 6.0 | > 100 | 9.0 | 7.9 | 3.2 | 3.8 |
| 7 | R = COOH | 66.6 ± 2.6 | > 100 | 8.1 | 3.8 | 0.6/5.5 | 3.4 |
| 8 | R = PO(OH)₂ | > 100 | > 100 | 8.1 | 1.1/5.9 d | d | 1.3 | a IC₅₀ in μM (Average ± SEM, n ≥ 3); b n = 2; c Calculated using ChemAxon Software Version 5.12.3; d pKa values from two hydroxyl groups.

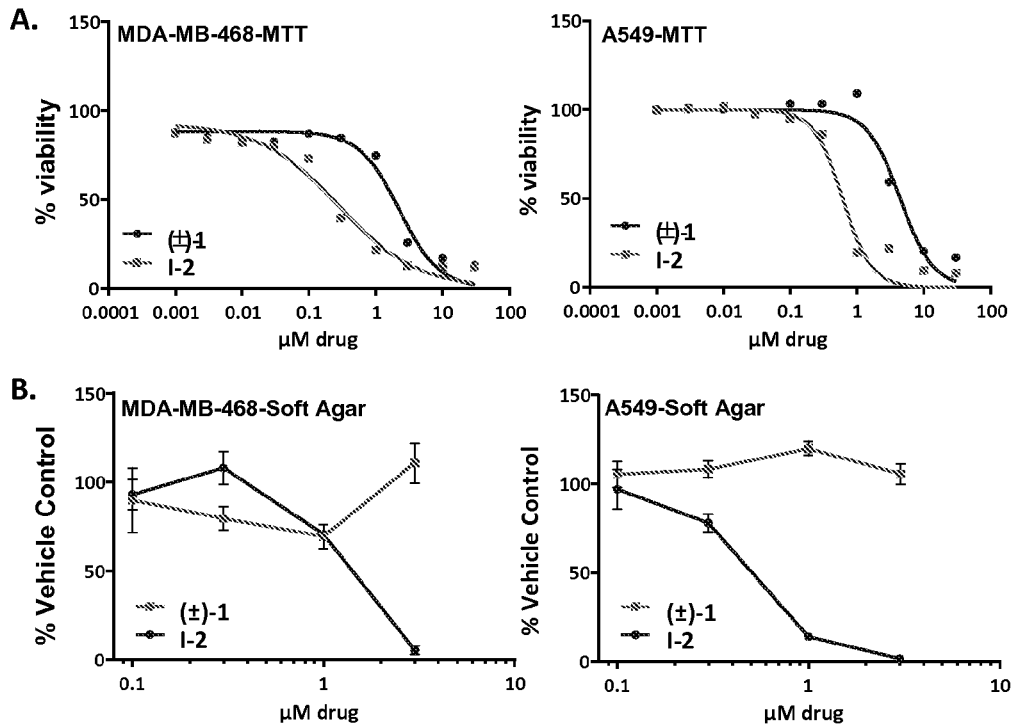
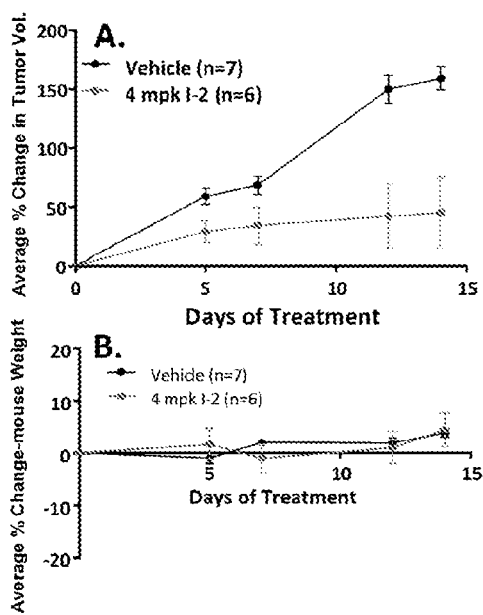
Figure 9
Figure 10

MARINOPYRROLE DERIVATIVES AND METHODS OF MAKING AND USING SAME

CROSS-REFERENCE TO RELATED APPLICATIONS

This application claims benefit of U.S. Provisional Application No. 61/941,374, filed Feb. 18, 2014, and U.S. Provisional Application No. 61/981,357, filed Apr. 18, 2014, which are hereby incorporated herein by reference in their entireties.

FIELD

The subject matter disclosed herein generally relates to marinopyrrole derivatives and methods of use thereof.

BACKGROUND

Apoptosis is the best-characterized mode of physiological cell death, which plays an essential role in the development and homeostasis of multicellular organisms. Apoptosis is executed by caspases, a family of cysteine proteases, whose activation is initiated via two major pathways: the death receptor (extrinsic) pathway and the mitochondrial (intrinsic) pathway. The activated caspases cleave a number of cellular proteins to generate many of the hallmark morphological features of apoptosis, including DNA fragmentation and membrane blebbing.

The Bcl-2 family of proteins plays a pivotal role in apoptosis by regulating the mitochondrial outer membrane permeabilization (MOMP). MOMP results in the release of apoptogenic factors (e.g., cytochrome c and Smac) from the mitochondria into the cytosol where they directly promote caspase activation and subsequent cell death. Members of the Bcl-2 family contain up to four evolutionarily conserved domains called Bcl-2 homology (BH) domains 1 to 4 and can be classified into three groups based on their domain architecture and function in apoptosis: multidomain (BH1-4) anti-apoptotic Bcl-2 proteins (e.g., Bcl-2, Bcl-$X_L$ and Mcl-1), multidomain (BH1-3) pro-apoptotic Bcl-2 proteins (e.g., Bax and Bak), and BH3-only Bcl-2 proteins (e.g., Bad, Bid, Bim, Noxa and Puma). Many of the Bcl-2 family proteins can interact with each other to determine the cell fate. The three-dimensional structures reveal that the BH1-3 domains of anti-apoptotic Bcl-2 proteins form a hydrophobic surface groove to which the BH3 domains of pro-apoptotic Bcl-2 family members bind (Sattler et al., (1997) Science 275:983-986; Day et al., (2008) J Mol Biol 380: 958-971). The multidomain pro-apoptotic Bcl-2 proteins Bax and Bak are two major effectors of MOMP, which homo-oligomerize and form pores in the mitochondrial outer membrane to induce MOMP upon apoptotic stimulation. The anti-apoptotic Bcl-2 proteins prevent MOMP by directly binding to both classes of pro-apoptotic Bcl-2 proteins. In contrast, the BH3-only proteins trigger Bax and Bak to induce MOMP. Based on their ability to interact with the multidomain anti- and pro-apoptotic Bcl-2 proteins, the BH3-only proteins are often further divided into two subgroups: direct activators and sensitizers/de-repressors. The direct activators, including Bid, Bim and Puma, are able to not only interact with and inhibit all the anti-apoptotic Bcl-2 proteins but also directly bind to and activate the effectors Bax and Bak. On the other hand, the sensitizers/de-repressors appear to function essentially as transdominant inhibitors by occupying the hydrophobic groove of anti-apoptotic Bcl-2 proteins, thereby displacing the direct activators to promote MOMP and preventing any future bindings of the direct activators or effectors to anti-apoptotic Bcl-2 proteins. Moreover, unlike the direct activators, the sensitizers/de-repressors are more selective in binding to the anti-apoptotic Bcl-2 members. For example, Bad binds and antagonizes Bcl-2 and Bcl-$X_L$ but not Mcl-1, whereas Noxa binds and antagonizes Mcl-1 but not Bcl-2 and Bcl-$X_L$. This observation indicates that the BH3-only proteins provide a fine control of MOMP in a Bax/Bak-dependent manner and opportunities to design specific inhibitors for each of the anti-apoptotic Bcl-2 family members.

The evasion of apoptosis is considered to be a hallmark of cancers and a cause of resistance to radiation and chemo-therapies. Consistently, high levels of the anti-apoptotic Bcl-2 family proteins are associated with the pathogenesis of cancer and resistance to therapy (Reed et al., (1996) J Cell Biochem 60:23-32; Reed, (1997) Adv Pharmacol 41:501-532). A recent analysis of somatic copy-number alterations (SCNAs) showed that two anti-apoptotic Bcl-2 family genes (Bcl-$X_L$ and Mcl-1) undergo frequent somatic amplifications in multiple cancers and that cancer cells carrying Bcl-$X_L$ and Mcl-1 amplifications are dependent on the expression of these genes for survival (Beroukhim et al., (2010) Nature 463:899-905). Thus, Bcl-$X_L$ and Mcl-1 are very attractive targets for the development of anticancer agents.

Over the last few years, several small-molecule Bcl-2 inhibitors have been synthesized as BH3 mimetics and some of these molecules have entered clinical trials (Yip et al., (2008) Oncogene 27:6398-6406; Vogler et al., (2009) Cell Death Differ 16:360-367; Kazi et al., (2011) J Biol Chem 286:9382-9392). Although Bcl-2 and Bcl-$X_L$ have been the primary focus for the design of small-molecule inhibitors, recent studies have demonstrated that Mcl-1 also plays an important role for cancer cell survival and that it is necessary to neutralize both arms of the anti-apoptotic Bcl-2 family (Bcl-2/Bcl-$X_L$ and Mcl-1) for apoptosis to occur in many cell types (Willis et al., (2005) Genes Dev 19:1294-1305).

To date, the most potent and selective small-molecule Bcl-2 inhibitors are ABT-737 and its orally active analog ABT-263, which inhibit Bcl-2 and Bcl-$X_L$ at subnanomolar concentrations but only weakly target Mcl-1 (Tse et al., (2008) Cancer Res 68:3421-3428). Consequently, these agents generally lack efficacy in cancers with elevated Mcl-1 and in many instances this resistance can be overcome by downregulation of Mcl-1 (Id.; Oltersdorf et al., (2005) Nature 435:677-681; van Delft et al., (2006) Cancer Cell 10:389-399; Chen et al., (2007) Cancer Res 67, 782-791; Konopleva et al., (2006) Cancer Cell 10:375-388; Lin et al., (2007) Oncogene 26:3972-3979; Tahir et al., (2007) Cancer Res 67:1176-1183). Moreover, it has recently been shown that cancer cells can quickly acquire resistance to ABT-737 by upregulation of Mcl-1 (Yecies et al., (2009) Blood 233-304; Hikita et al., (2010) Hepatology 52:1310-1321). What are thus needed are compounds that specifically bind to Mcl-1 to overcome such resistance. Such compounds can be used to treat and/or prevent various cancers. The compositions and methods disclosed herein address these and other needs.

SUMMARY

In accordance with the purposes of the disclosed materials, compounds, compositions, kits, and methods, as embodied and broadly described herein, the disclosed subject matter relates to compositions, methods of making said compositions, and methods of using said compositions. More specifically, marinopyrrole derivatives are provided herein. Also disclosed herein are methods of use of the marinopyrrole derivatives as anticancer agents. Also disclosed herein are methods of use of the marinopyrrole derivatives as antimicrobial agents. Also disclosed herein are methods of use of the marinopyrrole derivatives as antibacterial agents.

Methods of making and using marinopyrrole derivatives are also disclosed herein.

Additional advantages will be set forth in part in the description that follows or may be learned by practice of the aspects described below. The advantages described below will be realized and attained by means of the elements and combinations particularly pointed out in the appended claims. It is to be understood that both the foregoing general description and the following detailed description are exemplary and explanatory only and are not restrictive.

BRIEF DESCRIPTION OF THE FIGURES

The accompanying figures, which are incorporated in and constitute a part of this specification, illustrate several aspects described below.

FIG. 6 (B) displays a structural model of Mcl-1 with a view of the BH3 pocket highlighting the position of residues undergoing significant chemical shift perturbations. The NMR data are consistent with the II-4 and I-20 binding to the BH3 pocket of Mcl-1. BIM BH3 bound to Mcl-1 is shown for comparison. FIG. 6(C) displays cartoons highlighting the structure of each compound and specific interactions with the Mcl-1 binding site.

FIG. 9 displays the MTT and soft agar (anchorage-independent growth) results for MDA-MB-468 and A-549 cells treated with 1 or I-2 in (A) 96-well plate for 48 hours (MTT) and (B) 12-well plates for 21 days (soft agar).

FIG. 10 displays the average % change in (A) tumor size and (B) mouse weight in Nude mice bearing s/c/A-549 xenografts injected with vehicle or I-2 (4 mpk/day) for 14 days.

DETAILED DESCRIPTION

Figure 1:
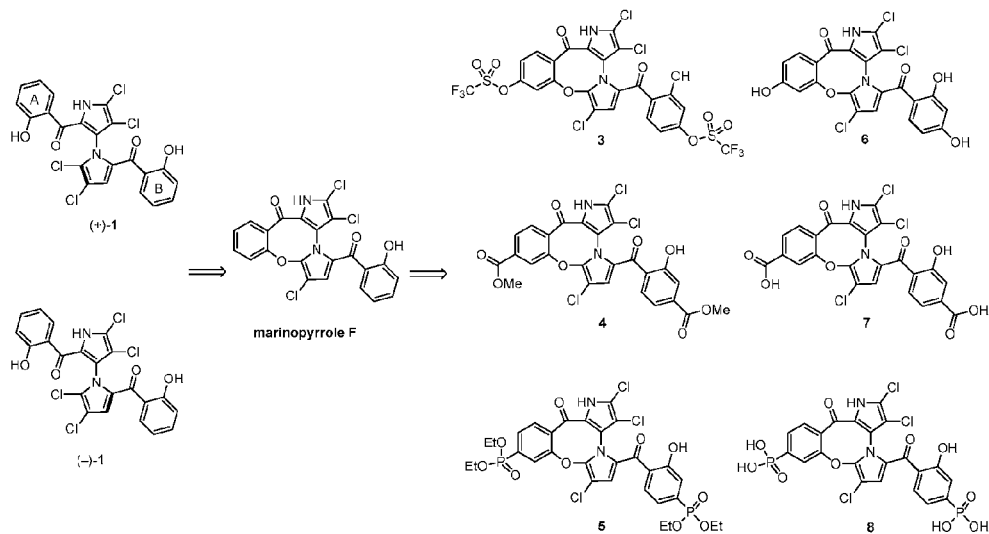
FIG. 1 shows the structure of marinopyrrole A (1) and cyclic marinopyrroles 3-8.

The materials, compounds, compositions, articles, and methods described herein may be understood more readily by reference to the following detailed description of specific aspects of the disclosed subject matter and the Examples included therein.

Before the present materials, compounds, compositions, kits, and methods are disclosed and described, it is to be understood that the aspects described below are not limited to specific synthetic methods or specific reagents, as such may, of course, vary. It is also to be understood that the terminology used herein is for the purpose of describing particular aspects only and is not intended to be limiting.

Also, throughout this specification, various publications are referenced. The disclosures of these publications in their entireties are hereby incorporated by reference into this application in order to more fully describe the state of the art to which the disclosed matter pertains. The references disclosed are also individually and specifically incorporated by reference herein for the material contained in them that is discussed in the sentence in which the reference is relied upon.

General Definitions

In this specification and in the claims that follow, reference will be made to a number of terms, which shall be defined to have the following meanings:

Throughout the description and claims of this specification the word "comprise" and other forms of the word, such as "comprising" and "comprises," means including but not limited to, and is not intended to exclude, for example, other additives, components, integers, or steps.

As used in the description and the appended claims, the singular forms "a," "an," and "the" include plural referents unless the context clearly dictates otherwise. Thus, for example, reference to "a composition" includes mixtures of two or more such compositions, reference to "the compound" includes mixtures of two or more such compounds, reference to "an agent" includes mixture of two or more such agents, and the like.

"Optional" or "optionally" means that the subsequently described event or circumstance can or cannot occur, and that the description includes instances where the event or circumstance occurs and instances where it does not.

Ranges can be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that when a value is disclosed, then "less than or equal to" the value, "greater than or equal to the value," and possible ranges between values are also disclosed, as appropriately understood by the skilled artisan. For example, if the value "10" is disclosed, then "less than or equal to 10" as well as "greater than or equal to 10" is also disclosed. It is also understood that throughout the application data are provided in a number of different formats and that this data represent endpoints and starting points and ranges for any combination of the data points. For example, if a particular data point "10" and a particular data point "15" are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

As used herein, by a "subject" is meant an individual. Thus, the "subject" can include domesticated animals (e.g., cats, dogs, etc.), livestock (e.g., cattle, horses, pigs, sheep, goats, etc.), laboratory animals (e.g., mouse, rabbit, rat, guinea pig, etc.), and birds. "Subject" can also include a mammal, such as a primate or a human.

By "reduce" or other forms of the word, such as "reducing" or "reduction," is meant lowering of an event or characteristic (e.g., tumor growth). It is understood that this is typically in relation to some standard or expected value, in other words it is relative, but that it is not always necessary for the standard or relative value to be referred to. For example, "reduces tumor growth" means reducing the rate of growth of a tumor relative to a standard or a control. For example, "reduces bacterial infection" means reducing the spread of a bacterial infection relative to a standard or a control.

By "prevent" or other forms of the word, such as "preventing" or "prevention," is meant to stop a particular event or characteristic, to stabilize or delay the development or progression of a particular event or characteristic, or to minimize the chances that a particular event or characteristic will occur. Prevent does not require comparison to a control as it is typically more absolute than, for example, reduce. As used herein, something could be reduced but not prevented, but something that is reduced could also be prevented. Likewise, something could be prevented but not reduced, but something that is prevented could also be reduced. It is understood that where reduce or prevent are used, unless specifically indicated otherwise, the use of the other word is also expressly disclosed.

By "treat" or other forms of the word, such as "treated" or "treatment," is meant to administer a composition or to perform a method in order to reduce, prevent, inhibit, or eliminate a particular characteristic or event (e.g., tumor growth or survival). The term "control" is used synonymously with the term "treat."

The term "anticancer" refers to the ability to treat or control cellular proliferation and/or tumor growth at any concentration.

By "antimicrobial" is meant the ability to treat or control (e.g., reduce, prevent, or eliminate) the growth of a microbe at any concentration. Similarly, the term "antibacterial" refers to the ability to treat or control cellular bacteria growth at any concentration.

It is understood that throughout this specification the identifiers "first" and "second" are used solely to aid in distinguishing the various components and steps of the disclosed subject matter. The identifiers "first" and "second" are not intended to imply any particular order, amount, preference, or importance to the components or steps modified by these terms.

Chemical Definitions

As used herein, the term "substituted" is contemplated to include all permissible substituents of organic compounds. In a broad aspect, the permissible substituents include acyclic and cyclic, branched and unbranched, carbocyclic and heterocyclic, and aromatic and nonaromatic substituents of organic compounds. Illustrative substituents include, for example, those described below. The permissible substituents can be one or more and the same or different for appropriate organic compounds. For purposes of this disclosure, the heteroatoms, such as nitrogen, can have hydrogen substituents and/or any permissible substituents of organic compounds described herein which satisfy the valences of the heteroatoms. This disclosure is not intended to be limited in any manner by the permissible substituents of organic compounds. Also, the terms "substitution" or "substituted with" include the implicit proviso that such substitution is in accordance with permitted valence of the substituted atom and the substituent, and that the substitution results in a stable compound, e.g., a compound that does not spontaneously undergo transformation such as by rearrangement, cyclization, elimination, etc.

"$Z^1$," "$Z^2$," "$Z^3$," and "$Z^4$" are used herein as generic symbols to represent various specific substituents. These symbols can be any substituent, not limited to those disclosed herein, and when they are defined to be certain substituents in one instance, they can, in another instance, be defined as some other substituents.

The term "aliphatic" as used herein refers to a non-aromatic hydrocarbon group and includes branched and unbranched, alkyl, alkenyl, or alkynyl groups.

The term "alkyl" as used herein is a branched or unbranched saturated hydrocarbon group of 1 to 24 carbon atoms, such as methyl, ethyl, n-propyl, isopropyl, n-butyl, isobutyl, t-butyl, pentyl, hexyl, heptyl, octyl, nonyl, decyl, dodecyl, tetradecyl, hexadecyl, eicosyl, tetracosyl, and the like. The alkyl group can also be substituted or unsubstituted. The alkyl group can be substituted with one or more groups including, but not limited to, alkyl, halogenated alkyl, alkoxy, alkenyl, alkynyl, aryl, heteroaryl, aldehyde, amino, carboxylic acid, ester, ether, halide, hydroxy, ketone, nitro, silyl, sulfo-oxo, sulfonyl, sulfone, sulfoxide, or thiol, as described below.

Throughout the specification "alkyl" is generally used to refer to both unsubstituted alkyl groups and substituted alkyl groups; however, substituted alkyl groups are also specifically referred to herein by identifying the specific substituent(s) on the alkyl group. For example, the term "halogenated alkyl" specifically refers to an alkyl group that is substituted with one or more halide, e.g., fluorine, chlorine, bromine, or iodine. The term "alkoxyalkyl" specifically refers to an alkyl group that is substituted with one or more alkoxy groups, as described below. The term "alkylamino" specifically refers to an alkyl group that is substituted with one or more amino groups, as described below, and the like. When "alkyl" is used in one instance and a specific term such as "alkylalcohol" is used in another, it is not meant to imply that the term "alkyl" does not also refer to specific terms such as "alkylalcohol" and the like.

This practice is also used for other groups described herein. That is, while a term such as "cycloalkyl" refers to both unsubstituted and substituted cycloalkyl moieties, the substituted moieties can, in addition, be specifically identified herein; for example, a particular substituted cycloalkyl can be referred to as, e.g., an "alkylcycloalkyl." Similarly, a substituted alkoxy can be specifically referred to as, e.g., a "halogenated alkoxy," a particular substituted alkenyl can be, e.g., an "alkenylalcohol," and the like. Again, the practice of using a general term, such as "cycloalkyl," and a specific term, such as "alkylcycloalkyl," is not meant to imply that the general term does not also include the specific term.

The term "alkoxy" as used herein is an alkyl group bound through a single, terminal ether linkage; that is, an "alkoxy" group can be defined as —OZ$^1$ where Z$^1$ is alkyl as defined above.

The term "alkenyl" as used herein is a hydrocarbon group of from 2 to 24 carbon atoms with a structural formula containing at least one carbon-carbon double bond. Asymmetric structures such as (Z$^1$Z$^2$)C=C(Z$^3$Z$^4$) are intended to include both the E and Z isomers. This can be presumed in structural formulae herein wherein an asymmetric alkene is present, or it can be explicitly indicated by the bond symbol C=C. The alkenyl group can be substituted with one or more groups including, but not limited to, alkyl, halogenated alkyl, alkoxy, alkenyl, alkynyl, aryl, heteroaryl, aldehyde, amino, carboxylic acid, ester, ether, halide, hydroxy, ketone, nitro, silyl, sulfo-oxo, sulfonyl, sulfone, sulfoxide, or thiol, as described below.

The term "alkynyl" as used herein is a hydrocarbon group of 2 to 24 carbon atoms with a structural formula containing at least one carbon-carbon triple bond. The alkynyl group can be substituted with one or more groups including, but not limited to, alkyl, halogenated alkyl, alkoxy, alkenyl, alkynyl, aryl, heteroaryl, aldehyde, amino, carboxylic acid, ester, ether, halide, hydroxy, ketone, nitro, silyl, sulfo-oxo, sulfonyl, sulfone, sulfoxide, or thiol, as described below.

The term "aryl" as used herein is a group that contains any carbon-based aromatic group including, but not limited to, benzene, naphthalene, phenyl, biphenyl, phenoxybenzene, and the like. The term "heteroaryl" is defined as a group that contains an aromatic group that has at least one heteroatom incorporated within the ring of the aromatic group. Examples of heteroatoms include, but are not limited to, nitrogen, oxygen, sulfur, and phosphorus. The term "non-heteroaryl," which is included in the term "aryl," defines a group that contains an aromatic group that does not contain a heteroatom. The aryl or heteroaryl group can be substituted or unsubstituted. The aryl or heteroaryl group can be substituted with one or more groups including, but not limited to, alkyl, halogenated alkyl, alkoxy, alkenyl, alkynyl, aryl, heteroaryl, aldehyde, amino, carboxylic acid, ester, ether, halide, hydroxy, ketone, nitro, silyl, sulfo-oxo, sulfonyl, sulfone, sulfoxide, or thiol as described herein. The term "biaryl" is a specific type of aryl group and is included in the definition of aryl. Biaryl refers to two aryl groups that are bound together via a fused ring structure, as in naphthalene, or are attached via one or more carbon-carbon bonds, as in biphenyl.

The term "cycloalkyl" as used herein is a non-aromatic carbon-based ring composed of at least three carbon atoms. Examples of cycloalkyl groups include, but are not limited to, cyclopropyl, cyclobutyl, cyclopentyl, cyclohexyl, etc. The term "heterocycloalkyl" is a cycloalkyl group as defined above where at least one of the carbon atoms of the ring is substituted with a heteroatom such as, but not limited to, nitrogen, oxygen, sulfur, or phosphorus. The cycloalkyl group and heterocycloalkyl group can be substituted or unsubstituted. The cycloalkyl group and heterocycloalkyl group can be substituted with one or more groups including, but not limited to, alkyl, alkoxy, alkenyl, alkynyl, aryl, heteroaryl, aldehyde, amino, carboxylic acid, ester, ether, halide, hydroxy, ketone, nitro, silyl, sulfo-oxo, sulfonyl, sulfone, sulfoxide, or thiol as described herein.

The term "cycloalkenyl" as used herein is a non-aromatic carbon-based ring composed of at least three carbon atoms and containing at least one double bound, i.e., C=C. Examples of cycloalkenyl groups include, but are not limited to, cyclopropenyl, cyclobutenyl, cyclopentenyl, cyclopentadienyl, cyclohexenyl, cyclohexadienyl, and the like. The term "heterocycloalkenyl" is a type of cycloalkenyl group as defined above, and is included within the meaning of the term "cycloalkenyl," where at least one of the carbon atoms of the ring is substituted with a heteroatom such as, but not limited to, nitrogen, oxygen, sulfur, or phosphorus. The cycloalkenyl group and heterocycloalkenyl group can be substituted or unsubstituted. The cycloalkenyl group and heterocycloalkenyl group can be substituted with one or more groups including, but not limited to, alkyl, alkoxy, alkenyl, alkynyl, aryl, heteroaryl, aldehyde, amino, carboxylic acid, ester, ether, halide, hydroxy, ketone, nitro, silyl, sulfo-oxo, sulfonyl, sulfone, sulfoxide, or thiol as described herein.

The term "cyclic group" is used herein to refer to either aryl groups, non-aryl groups (i.e., cycloalkyl, heterocycloalkyl, cycloalkenyl, and heterocycloalkenyl groups), or both. Cyclic groups have one or more ring systems that can be substituted or unsubstituted. A cyclic group can contain one or more aryl groups, one or more non-aryl groups, or one or more aryl groups and one or more non-aryl groups.

The term "aldehyde" as used herein is represented by the formula —C(O)H. Throughout this specification "C(O)" or "CO" is a short hand notation for C=O.

The terms "amine" or "amino" as used herein are represented by the formula —NZ$^1$Z$^2$, where Z$^1$ and Z$^2$ can each be substitution group as described herein, such as hydrogen, an alkyl, halogenated alkyl, alkenyl, alkynyl, aryl, heteroaryl, cycloalkyl, cycloalkenyl, heterocycloalkyl, or heterocycloalkenyl group described above.

The term "carboxylic acid" as used herein is represented by the formula —C(O)OH. A "carboxylate" or "carboxyl" group as used herein is represented by the formula —C(O)O$^-$.

The term "ester" as used herein is represented by the formula —OC(O)Z$^1$ or —C(O)OZ$^1$, where Z$^1$ can be an alkyl, halogenated alkyl, alkenyl, alkynyl, aryl, heteroaryl, cycloalkyl, cycloalkenyl, heterocycloalkyl, or heterocycloalkenyl group described above.

The term "ether" as used herein is represented by the formula Z$^1$OZ$^2$, where Z$^1$ and Z$^2$ can be, independently, an alkyl, halogenated alkyl, alkenyl, alkynyl, aryl, heteroaryl, cycloalkyl, cycloalkenyl, heterocycloalkyl, or heterocycloalkenyl group described above.

The term "ketone" as used herein is represented by the formula Z$^1$C(O)Z$^2$, where Z$^1$ and Z$^2$ can be, independently, an alkyl, halogenated alkyl, alkenyl, alkynyl, aryl, heteroaryl, cycloalkyl, cycloalkenyl, heterocycloalkyl, or heterocycloalkenyl group described above.

The term "halide" or "halogen" as used herein refers to the fluorine, chlorine, bromine, and iodine.

The term "hydroxyl" as used herein is represented by the formula —OH.

The term "nitro" as used herein is represented by the formula —NO$_2$.

The term "silyl" as used herein is represented by the formula —SiZ$^1$Z$^2$Z$^3$, where Z$^1$, Z$^2$, and Z$^3$ can be, independently, hydrogen, alkyl, halogenated alkyl, alkoxy, alkenyl, alkynyl, aryl, heteroaryl, cycloalkyl, cycloalkenyl, heterocycloalkyl, or heterocycloalkenyl group described above.

The term "sulfonyl" is used herein to refer to the sulfo-oxo group represented by the formula —S(O)$_2$Z$^1$, where Z$^1$ can be hydrogen, an alkyl, halogenated alkyl, alkenyl, alkynyl, aryl, heteroaryl, cycloalkyl, cycloalkenyl, heterocycloalkyl, or heterocycloalkenyl group described above.

The term "sulfonylamino" or "sulfonamide" as used herein is represented by the formula —S(O)$_2$NH—.

The term "phosphonyl" is used herein to refer to the phospho-oxo group represented by the formula —P(O)(OZ$^1$)$_2$, where Z$^1$ can be hydrogen, an alkyl, halogenated alkyl, alkenyl, alkynyl, aryl, heteroaryl, cycloalkyl, cycloalkenyl, heterocycloalkyl, or heterocycloalkenyl group described above.

The term "thiol" as used herein is represented by the formula —SH.

The term "thio" as used herein is represented by the formula —S—.

"R$^1$," "R$^2$," "R$^3$," "R$^n$," etc., where n is some integer, as used herein can, independently, possess one or more of the groups listed above. For example, if R$^1$ is a straight chain alkyl group, one of the hydrogen atoms of the alkyl group can optionally be substituted with a hydroxyl group, an alkoxy group, an amine group, an alkyl group, a halide, and the like. Depending upon the groups that are selected, a first group can be incorporated within second group or, alternatively, the first group can be pendant (i.e., attached) to the second group. For example, with the phrase "an alkyl group comprising an amino group," the amino group can be incorporated within the backbone of the alkyl group. Alternatively, the amino group can be attached to the backbone of the alkyl group. The nature of the group(s) that is (are) selected will determine if the first group is embedded or attached to the second group.

Unless stated to the contrary, a formula with chemical bonds shown only as solid lines and not as wedges or dashed lines contemplates each possible isomer, e.g., each enantiomer, diastereomer, and meso compound, and a mixture of isomers, such as a racemic or scalemic mixture.

The following abbreviations are used herein: ADME, absorption, distribution, metabolism and excretion; DCM, dichloromethane; DPPP, bis(diphenylphosphino)propane; DIEA, diisopropylethylamine; DMF, dimethylformamide; DMSO, dimethyl sulfoxide; EtOAc, ethyl acetate; ESI, electrospray ionization; IBX, 2-iodoxybenzoic acid; KBr, potassium bromide; KF, potassium fluoride; MeCN, acetonitrile; MeOH, methyl alcohol; NCS, N-chlorosuccinimide; SAR, Structure Activity Relationship; TBAF, tetrabutylammonium fluoride; TBDMS, t-butyldimethylsilyl; TBDMSCl, t-butyldimethylsilyl chloride; Tf, trifluoromethanesulfonyl; THF, tetrahydrofuran.

Reference will now be made in detail to specific aspects of the disclosed materials, compounds, compositions, articles, and methods, examples of which are illustrated in the accompanying Examples and Figures.

Compounds

Marinopyrrole derivatives are described herein. The marinopyrrole derivatives can have the following Formula I:

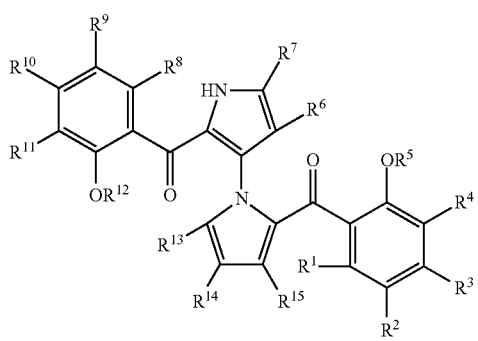

I wherein R$^1$, R$^2$, R$^3$, R$^4$, R$^6$, R$^7$, R$^8$, R$^9$, R$^{10}$, R$^{11}$, R$^{14}$, and R$^{15}$ are each independently selected from hydrogen, halogen, hydroxyl, cyano, nitro, sulfonyl, phosphonyl, carboxylate, substituted or unsubstituted amino, substituted or unsubstituted alkyl, substituted or unsubstituted heteroalkyl, substituted or unsubstituted alkenyl, substituted or unsubstituted heteroalkenyl, substituted or unsubstituted alkynyl, substituted or unsubstituted heteroalkynyl, substituted or unsubstituted aryl, substituted or unsubstituted heteroaryl, substituted or unsubstituted alkoxyl, substituted or unsubstituted aryloxyl, and substituted or unsubstituted carboxyl;

wherein R$^1$, R$^2$, R$^3$, R$^4$, R$^6$, R$^7$, R$^8$, R$^9$, R$^{10}$, R$^{11}$, R$^{13}$, and R$^{14}$ are independently chosen from hydrogen, halogen, hydroxyl, cyano, nitro, sulfonyl, phosphonyl, substituted or unsubstituted amino, substituted or unsubstituted alkyl, substituted or unsubstituted cycloalkyl, substituted or unsubstituted heteroalkyl, substituted or unsubstituted heterocycloalkyl, substituted or unsubstituted alkenyl, substituted or unsubstituted cycloalkenyl, substituted or unsubstituted heteroalkenyl, substituted or unsubstituted heterocycloalkenyl, substituted or unsubstituted alkynyl, substituted or unsubstituted heteroalkynyl, substituted or unsubstituted aryl, substituted or unsubstituted heteroaryl, substituted or unsubstituted alkoxyl, substituted or unsubstituted aryloxyl, and substituted or unsubstituted carboxyl;

R$^5$ and R$^{12}$ are independently chosen from hydrogen, halogen, substituted or unsubstituted alkyl, substituted or unsubstituted heteroalkyl, substituted or unsubstituted aryl, substituted or unsubstituted heteroaryl, and a monovalent cation and (+), (−), and (±) isomers, and pharmaceutically acceptable salts and prodrugs thereof.

In some examples of Formula I, adjacent R groups, e.g., R$^1$ and R$^2$, can be combined to form a substituted or unsubstituted aryl, substituted or unsubstituted heteroaryl, substituted or unsubstituted cycloalkyl, substituted or unsubstituted cycloalkenyl, substituted or unsubstituted cycloalkynyl, substituted or unsubstituted heterocycloalkyl, substituted or unsubstituted heterocycloalkenyl, or substituted or unsubstituted heterocycloalkynyl. For example, R$^1$ can be a substituted or unsubstituted ethylene group and R$^2$ can be a substituted or unsubstituted propylene group that combine to form a substituted or unsubstituted phenyl. Other adjacent R groups include the combinations of R$^2$ and R$^3$; R$^3$ and R$^4$; R$^6$ and R$^7$; R$^8$ and R$^9$; R$^9$ and R$^{10}$; R$^{10}$ and R$^{11}$; and R$^{14}$ and R$^{15}$.

In some examples of Formula I, the marinopyrrole derivatives can be of Formula II:

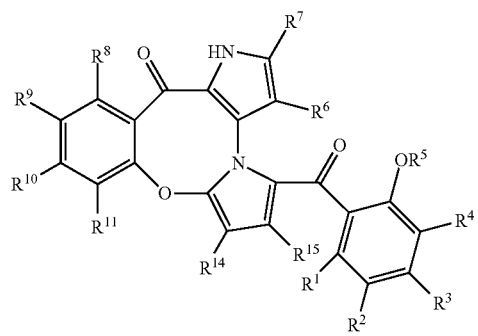

II wherein R$^1$, R$^2$, R$^3$, R$^4$, R$^6$, R$^7$, R$^8$, R$^9$, R$^{10}$, R$^{11}$, R$^{14}$, and R$^{15}$ are each independently selected from hydrogen, halogen, hydroxyl, cyano, nitro, sulfonyl, phosphonyl, carboxylate, substituted or unsubstituted amino, substituted or unsubstituted alkyl, substituted or unsubstituted heteroalkyl, substituted or unsubstituted alkenyl, substituted or unsubstituted heteroalkenyl, substituted or unsubstituted alkynyl, substituted or unsubstituted heteroalkynyl, substituted or unsubstituted aryl, substituted or unsubstituted heteroaryl, substituted or unsubstituted alkoxyl, substituted or unsubstituted aryloxyl, and substituted or unsubstituted carboxyl;

$R^5$ is selected from hydrogen, substituted or unsubstituted alkyl, substituted or unsubstituted heteroalkyl, substituted or unsubstituted aryl, substituted or unsubstituted heteroaryl, and a monovalent cation;

and (+), (−), and (±) isomers, and pharmaceutically acceptable salts and prodrugs thereof.

Examples of monovalent cations include, but are not limited to $Na^+$, $Li^+$, $K^+$, and $NH_4^+$.

In some examples of Formula II, $R^1$, $R^2$, $R^3$, $R^4$, $R^5$, $R^9$, $R^{10}$, and $R^{11}$ are independently selected from hydrogen, halogen, hydroxyl, sulfonyl, phosphonyl, carboxylate, substituted or unsubstituted amino, and substituted or unsubstituted carboxyl. In some examples of Formula II, $R^1$, $R^2$, $R^3$, $R^4$, $R^8$, $R^9$, $R^{10}$, and $R^{11}$ are independently selected from hydrogen, $OCH_3$, $OR^{16}$, $NH_2$, $NHR^{16}$, $S(O)_2R^{16}$, $P(O)(OR^{16})_2$, and $CO_2R^{16}$, wherein $R^{16}$ is H, substituted or unsubstituted alkyl, substituted or unsubstituted cycloalkyl, substituted or unsubstituted heteroalkyl, substituted or unsubstituted heterocycloalkyl, substituted or unsubstituted aryl, or substituted or unsubstituted heteroaryl.

In some examples of Formula II, one or more of $R^1$, $R^2$, $R^3$, $R^4$, $R^8$, $R^9$, $R^{10}$, and $R^{11}$ is a halogen (e.g., F, Cl, Br, I). In some examples of Formula II, one of $R^1$, $R^2$, $R^3$, and $R^4$ is a halogen (e.g., F, Cl, Br, I).

In some examples of Formula II, $R^6$, $R^7$, $R^{14}$ and $R^{15}$ are independently selected from hydrogen, halogen (e.g., F, Cl, Br, I) and hydroxyl. In some examples of Formula II, one of $R^6$, $R^7$, $R^{14}$ and $R^{15}$ is a halogen (e.g., F, Cl, Br, I). In some examples of Formula II, $R^6$, $R^7$, $R^{14}$ and $R^{15}$ are independently selected from F, Cl, Br, and I.

In some examples of Formula II, $R^5$ is selected from hydrogen, substituted or unsubstituted alkyl, substituted or unsubstituted heteralkyl, substituted or unsubstituted aryl, substituted or unsubstituted heteroaryl, and a monovalent cation (e.g., $Na^+$, $Li^+$, $K^+$, or $NH_4^+$).

In some examples of Formula II, adjacent R groups, e.g., $R^1$ and $R^2$, can be combined to form a substituted or unsubstituted aryl, substituted or unsubstituted heteroaryl, substituted or unsubstituted cycloalkyl, substituted or unsubstituted cycloalkenyl, substituted or unsubstituted cycloalkynyl, substituted or unsubstituted heterocycloalkyl, substituted or unsubstituted heterocycloalkenyl, or substituted or unsubstituted heterocycloalkynyl. For example, $R^1$ can be a substituted or unsubstituted ethylene group and $R^2$ can be a substituted or unsubstituted propylene group that combine to form a substituted or unsubstituted phenyl. Other adjacent R groups include the combinations of $R^2$ and $R^3$; $R^3$ and $R^4$; $R^6$ and $R^7$; $R^8$ and $R^9$; $R^9$ and $R^{10}$; $R^{10}$ and $R^{11}$; and $R^{14}$ and $R^{15}$.

In some examples of Formula II, $R^{15}$ is hydrogen.

In some examples of Formula II, the compounds are of Formula II-1:

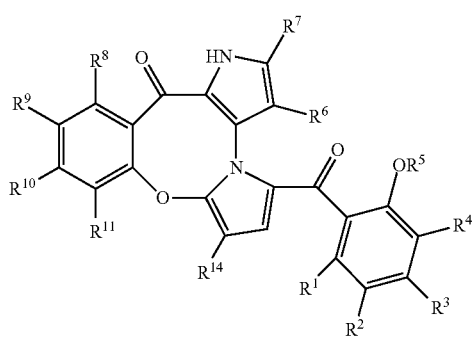

II-1 wherein $R^1$, $R^2$, $R^3$, $R^4$, $R^8$, $R^9$, $R^{10}$, and $R^{11}$ are independently selected from hydrogen, halogen, hydroxyl, cyano, nitro, sulfonyl, phosphonyl, substituted or unsubstituted amino, substituted or unsubstituted alkyl, substituted or unsubstituted heteroalkyl, substituted or unsubstituted alkenyl, substituted or unsubstituted heteroalkenyl, substituted or unsubstituted alkynyl, substituted or unsubstituted heteroalkynyl, substituted or unsubstituted aryl, substituted or unsubstituted heteroaryl, substituted or unsubstituted alkoxyl, substituted or unsubstituted aryloxyl, and substituted or unsubstituted carboxyl;

$R^6$, $R^7$, and $R^{14}$ are independently selected from F, Cl, Br, and I;

$R^5$ is selected from hydrogen, substituted or unsubstituted alkyl, substituted or unsubstituted heteroalkyl, substituted or unsubstituted aryl, substituted or unsubstituted heteroaryl, and a monovalent cation;

and (+), (−), and (±) isomers, and pharmaceutically acceptable salts and prodrugs thereof.

In some examples of Formula II, one or more of $R^1$, $R^2$, $R^4$, $R^8$, $R^9$, and $R^{11}$ is hydrogen.

In some examples of Formula II, the compounds are of Formula III:

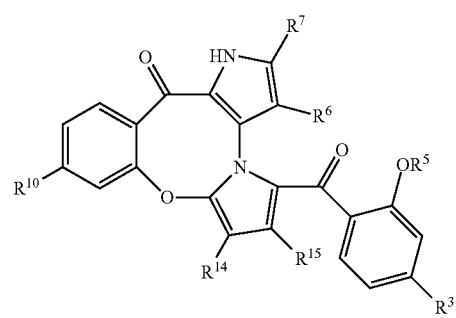

III wherein $R^3$, $R^6$, $R^7$, $R^{10}$, $R^{14}$, and $R^{15}$ are independently selected from hydrogen, halogen, hydroxyl, cyano, nitro, sulfonyl, phosphonyl, substituted or unsubstituted amino, substituted or unsubstituted alkyl, substituted or unsubstituted heteroalkyl, substituted or unsubstituted alkenyl, substituted or unsubstituted heteroalkenyl, substituted or unsubstituted alkynyl, substituted or unsubstituted heteroalkynyl, substituted or unsubstituted aryl, substituted or unsubstituted heteroaryl, substituted or unsubstituted alkoxyl, substituted or unsubstituted aryloxyl, and substituted or unsubstituted carboxyl;

$R^5$ is selected from hydrogen, substituted or unsubstituted alkyl, substituted or unsubstituted heteroalkyl, substituted or unsubstituted aryl, substituted or unsubstituted heteroaryl, and a monovalent cation;

and (+), (−), and (±) isomers, and pharmaceutically acceptable salts and prodrugs thereof.

In some examples of Formula III, $R^3$ and $R^{10}$ are independently selected from hydrogen, halogen, hydroxyl, sulfonyl, phosphonyl, carboxylate, substituted or unsubstituted amino, and substituted or unsubstituted carboxyl. In some examples of Formula III, $R^3$ and $R^{10}$ are independently selected from hydrogen, $OCH_3$, $OR^{16}$, $NH_2$, $NHR^{16}$, $S(O)_2R^{16}$, $P(O)(OR^{16})_2$, and $CO_2R^{16}$, wherein $R^{16}$ is H, substituted or unsubstituted alkyl, substituted or unsubstituted herteroalkyl, substituted or unsubstituted heterocycloalkyl, substituted or unsubstituted aryl, or substituted or unsubstituted heteroaryl.

In some examples of Formula III, the compounds are of Formula III-1:

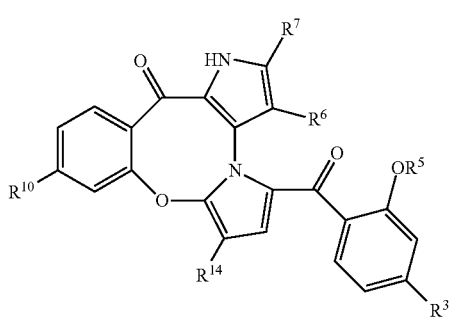

wherein $R^3$, and $R^{10}$ are independently selected from hydrogen, halogen, hydroxyl, cyano, nitro, sulfonyl, phosphonyl, substituted or unsubstituted amino, substituted or unsubstituted alkyl, substituted or unsubstituted heteroalkyl, substituted or unsubstituted alkenyl, substituted or unsubstituted heteroalkenyl, substituted or unsubstituted alkynyl, substituted or unsubstituted heteroalkynyl, substituted or unsubstituted aryl, substituted or unsubstituted heteroaryl, substituted or unsubstituted alkoxyl, substituted or unsubstituted aryloxyl, and substituted or unsubstituted carboxyl;

$R^6$, $R^7$, and $R^{14}$, are independently selected from F, Cl, Br, and I;

$R^5$ is selected from hydrogen, substituted or unsubstituted alkyl, substituted or unsubstituted heteroalkyl, substituted or unsubstituted aryl, substituted or unsubstituted heteroaryl, and a monovalent cation;

and (+), (−), and (±) isomers, and pharmaceutically acceptable salts and prodrugs thereof.

In some examples of Formula III, the compounds are of Formula III-2:

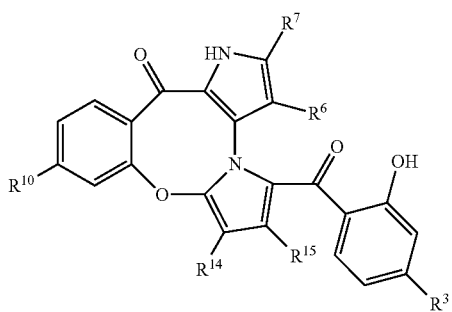

wherein $R^3$, $R^6$, $R^7$, $R^{10}$, $R^{14}$ and $R^{15}$ are independently selected from hydrogen, halogen, hydroxyl, cyano, nitro, sulfonyl, phosphonyl, substituted or unsubstituted amino, substituted or unsubstituted alkyl, substituted or unsubstituted heteroalkyl, substituted or unsubstituted alkenyl, substituted or unsubstituted heteroalkenyl, substituted or unsubstituted alkynyl, substituted or unsubstituted heteroalkynyl, substituted or unsubstituted aryl, substituted or unsubstituted heteroaryl, substituted or unsubstituted alkoxyl, substituted or unsubstituted aryloxyl, and substituted or unsubstituted carboxyl;

and (+), (−), and (±) isomers, and pharmaceutically acceptable salts and prodrugs thereof.

In some examples of Formula III, the compounds are of Formula III-3:

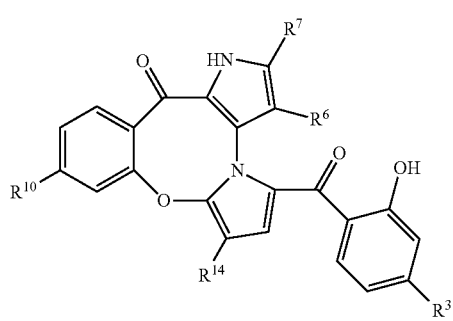

wherein $R^3$ and $R^{10}$ are independently selected from halogen, hydroxyl, cyano, nitro, sulfonyl, phosphonyl, substituted or unsubstituted amino, substituted or unsubstituted alkyl, substituted or unsubstituted heteroalkyl, substituted or unsubstituted alkenyl, substituted or unsubstituted heteroalkenyl, substituted or unsubstituted alkynyl, substituted or unsubstituted heteroalkynyl, substituted or unsubstituted aryl, substituted or unsubstituted heteroaryl, substituted or unsubstituted alkoxyl, substituted or unsubstituted aryloxyl, and substituted or unsubstituted carboxyl;

$R^6$, $R^7$, and $R^{14}$, are independently selected from F, Cl, Br, and I;

and (+), (−), and (±) isomers, and pharmaceutically acceptable salts and prodrugs thereof.

In some examples of Formula III-3, one or more of $R^6$, $R^7$, and $R^{14}$ is Cl. In some examples of Formula III-3, $R^6$ is Cl. In some examples of Formula III-3, $R^7$ is Cl. In some examples of Formula III-3, $R^{14}$ is Cl. In some examples of Formula III-3, $R^6$ and $R^7$ are Cl. In some examples of Formula III-3, $R^7$, and $R^{14}$ are Cl. In some examples of Formula III-3, $R^6$ and $R^{14}$ are Cl.

In some examples of Formula III-3, the compounds are of Formula III-4:

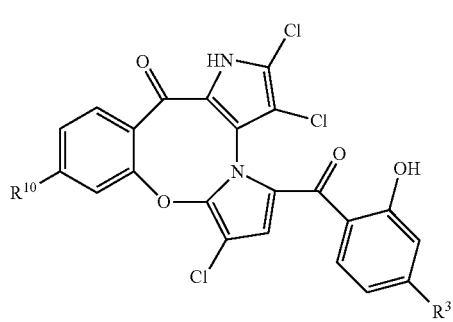

wherein $R^3$ and $R^{10}$ are independently selected from halogen, hydroxyl, cyano, nitro, sulfonyl, phosphonyl, substituted or unsubstituted amino, substituted or unsubstituted alkyl, substituted or unsubstituted heteroalkyl, substituted or unsubstituted alkenyl, substituted or unsubstituted heteroalkenyl, substituted or unsubstituted alkynyl, substituted or unsubstituted heteroalkynyl, substituted or unsubstituted aryl, substituted or unsubstituted heteroaryl, substituted or unsubstituted alkoxyl, substituted or unsubstituted aryloxyl, and substituted or unsubstituted carboxyl;

and (+), (−), and (±) isomers, and pharmaceutically acceptable salts and prodrugs thereof.

In some examples of Formula III-4, the compounds are of Formula IV:

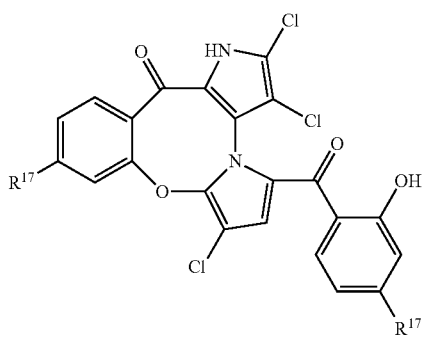

IV wherein $R^{17}$ is selected from halogen, hydroxyl, cyano, nitro, sulfonyl, phosphonyl, substituted or unsubstituted amino, substituted or unsubstituted alkyl, substituted or unsubstituted heteroalkyl, substituted or unsubstituted alkenyl, substituted or unsubstituted heteroalkenyl, substituted or unsubstituted alkynyl, substituted or unsubstituted heteroalkynyl, substituted or unsubstituted aryl, substituted or unsubstituted heteroaryl, substituted or unsubstituted alkoxyl, substituted or unsubstituted aryloxyl, and substituted or unsubstituted carboxyl;

and (+), (−), and (±) isomers, and pharmaceutically acceptable salts and prodrugs thereof.

In some examples of Formula IV, $R^{17}$ is selected from hydroxyl, sulfonyl, phosphonyl, and substituted or unsubstituted carboxyl. In some examples of Formula IV, $R^{17}$ is selected from hydroxyl, $S(O)_2R^{16}$, $P(O)(OR^{16})_2$, and $CO_2R^{16}$, wherein $R^{16}$ is H, substituted or unsubstituted alkyl, substituted or unsubstituted cycloalkyl, substituted or unsubstituted herteroalkyl, substituted or unsubstituted heterocycloalkyl, substituted or unsubstituted aryl, or substituted or unsubstituted heteroaryl. In some examples of Formula IV, $R^{17}$ is selected from $SO_2CF_3$, OH, $CO_2CH_3$, $CO_2H$, $PO(OCH_2CH_3)_2$, and $PO(OH)_2$.

In some examples of Formula IV, the compounds are of Formula IV-1:

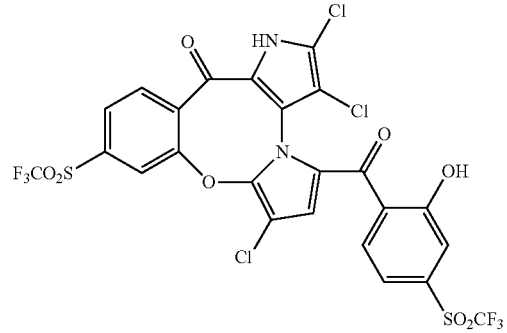

IV-1 and (+), (−), and (±) isomers, and pharmaceutically acceptable salts and prodrugs thereof.

In some examples of Formula IV, the compounds are of Formula IV-2:

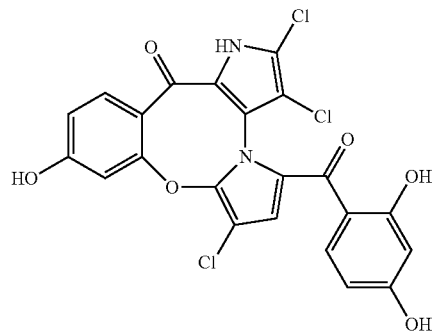

IV-2 and (+), (−), and (±) isomers, and pharmaceutically acceptable salts and prodrugs thereof.

In some examples of Formula IV, the compounds are of Formula IV-3:

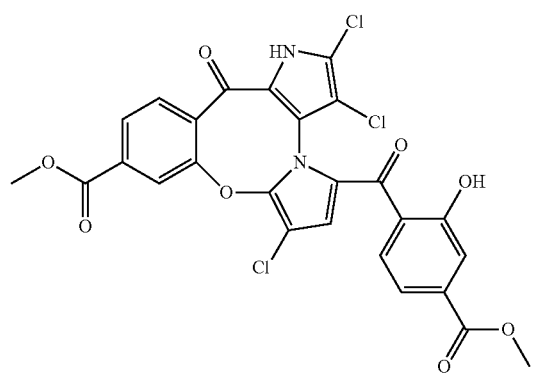

IV-3 and (+), (−), and (±) isomers, and pharmaceutically acceptable salts and prodrugs thereof.

In some examples of Formula IV, the compounds are of Formula IV-4:

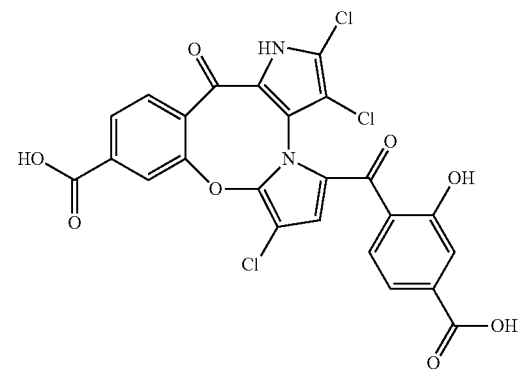

IV-4 and (+), (−), and (±) isomers, and pharmaceutically acceptable salts and prodrugs thereof.

In some examples of Formula IV, the compounds are of Formula IV-5:

and (+), (−), and (±) isomers, and pharmaceutically acceptable salts and prodrugs thereof.

In some examples of Formula IV, the compounds are of Formula IV-6:

and (+), (−), and (±) isomers, and pharmaceutically acceptable salts and prodrugs thereof.

In some examples of Formula I, the marinopyrrole derivatives can have the following Formula V:

wherein $R^6$, $R^7$, $R^{13}$, and $R^{14}$ are independently chosen from hydrogen, halogen, and hydroxyl;

$R^5$ and $R^{12}$ are independently chosen from hydrogen, halogen, and substituted or unsubstituted alkyl;

$R^2$, $R^9$, $R^{18}$ and $R^{19}$ are independently chosen from hydrogen, halogen, hydroxyl, cyano, nitro, sulfonyl, phosphonyl, substituted or unsubstituted amino, substituted or unsubstituted alkyl, substituted or unsubstituted cycloalkyl, substituted or unsubstituted heteroalkyl, substituted or unsubstituted heterocycloalkyl, substituted or unsubstituted alkenyl, substituted or unsubstituted cycloalkenyl, substituted or unsubstituted heteroalkenyl, substituted or unsubstituted heterocycloalkenyl, substituted or unsubstituted alkynyl, substituted or unsubstituted heteroalkynyl, substituted or unsubstituted aryl, substituted or unsubstituted heteroaryl, substituted or unsubstituted alkoxyl, substituted or unsubstituted aryloxyl, and substituted or unsubstituted carboxyl;

and (+), (−), and (±) isomers, and pharmaceutically acceptable salts and prodrugs thereof.

In some examples of Formula V, $R^6$, $R^7$, $R^{13}$ and $R^{14}$ are each independently a halogen (e.g., F, Cl, Br, or I). In some examples of Formula V, $R^6$, $R^7$, $R^{13}$ and $R^{14}$ are each Cl.

In some examples of Formula V, $R^5$ and $R^{12}$ are each H.

In some examples of Formula V, where $R^6$, $R^7$, $R^{13}$ and $R^{14}$ are each Cl, $R^5$ and $R^{12}$ are each H, $R^2$ and $R^9$ are each $R^a$, and $R^{18}$ and $R^{19}$ are each $R^b$, the compounds are of Formula B:

wherein $R^a$ and $R^b$ are independently chosen from hydrogen, halogen, hydroxyl, cyano, nitro, sulfonyl, phosphonyl, substituted or unsubstituted amino, substituted or unsubstituted alkyl, substituted or unsubstituted cycloalkyl, substituted or unsubstituted heteroalkyl, substituted or unsubstituted heterocycloalkyl, substituted or unsubstituted alkenyl, substituted or unsubstituted cycloalkenyl, substituted or unsubstituted heteroalkenyl, substituted or unsubstituted heterocycloalkenyl, substituted or unsubstituted alkynyl, substituted or unsubstituted heteroalkynyl, substituted or unsubstituted aryl, substituted or unsubstituted heteroaryl, substituted or unsubstituted alkoxyl, substituted or unsubstituted aryloxyl, and substituted or unsubstituted carboxyl;

and (+), (−), and (±) isomers, and pharmaceutically acceptable salts and prodrugs thereof.

In some examples of Formula B, $R^a$ is chosen from hydrogen and halogen (e.g., F, Cl, Br and I). In some examples of Formula B, $R^a$ is chosen from hydrogen and Cl. In some examples of Formula B, $R^b$ is chosen from substituted or unsubstituted alkyl, substituted or unsubstituted cycloalkyl, substituted or unsubstituted aryl, and substituted or unsubstituted carboxyl. In some examples of Formula B, $R^b$ is chosen from $CH_2CO_2CH_2CH_3$, $CH_2CO_2Bu$ (where Bu indicates a butyl group), $CH_2CO_2H$, $CH_2Ph$ (where Ph indicates a phenyl group), Ph, cyclohexane, and n-octane.

In some examples for Formula B, where $R^a$ comprises H, the compounds are of Formula B-1:

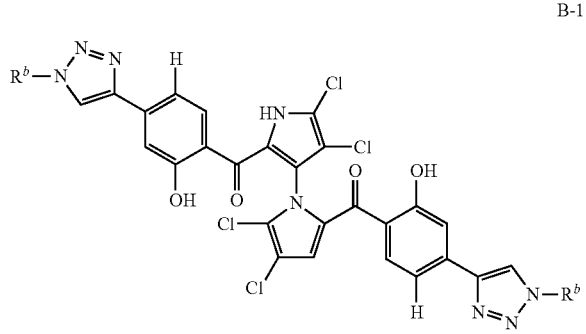

B-1 wherein $R^b$ is chosen from substituted or unsubstituted alkyl, substituted or unsubstituted cycloalkyl, substituted or unsubstituted aryl, and substituted or unsubstituted carboxyl; and (+), (−), and (±) isomers, and pharmaceutically acceptable salts and prodrugs thereof.

In some examples of Formula B-1, $R^b$ is chosen from $CH_2CO_2CH_2CH_3$, $CH_2CO_2Bu$ (where Bu indicates a butyl group, such as n-butyl, isobutyl, sec-butyl, or tert-butyl), $CH_2CO_2H$, $CH_2Ph$ (where Ph indicates a phenyl group), Ph, cyclohexane, and n-octane.

In some examples for Formula B, where $R^a$ is Cl, the compounds are of Formula B-2:

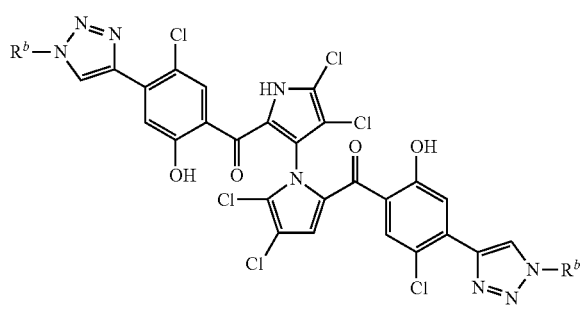

B-2 wherein $R^b$ is chosen from substituted or unsubstituted alkyl, substituted or unsubstituted cycloalkyl, substituted or unsubstituted aryl, and substituted or unsubstituted carboxyl; and (+), (−), and (±) isomers, and pharmaceutically acceptable salts and prodrugs thereof.

In some examples of Formula B-2, $R^b$ is chosen from $CH_2CO_2CH_2CH_3$, $CH_2CO_2Bu$ (where Bu indicates a butyl group), $CH_2CO_2H$, $CH_2Ph$ (where Ph indicates a phenyl group), Ph, cyclohexane, and n-octane.

In some examples for Formula B, where $R^a$ is Cl and $R^b$ is $CH_2CO_2CH_2CH_3$, the compounds are of Formula B-3:

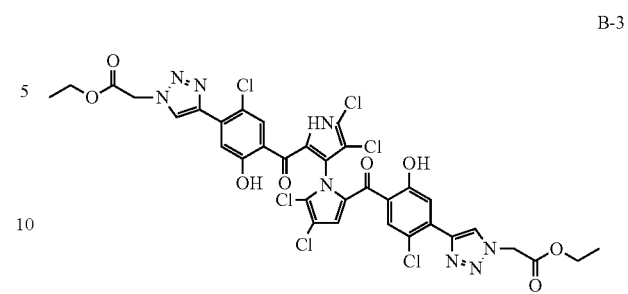

B-3 and (+), (−), and (±) isomers, and pharmaceutically acceptable salts and prodrugs thereof.

In some examples for Formula B, where $R^a$ is Cl and $R^b$ is $CH_2CO_2Bu$, the compounds are of Formula B-4:

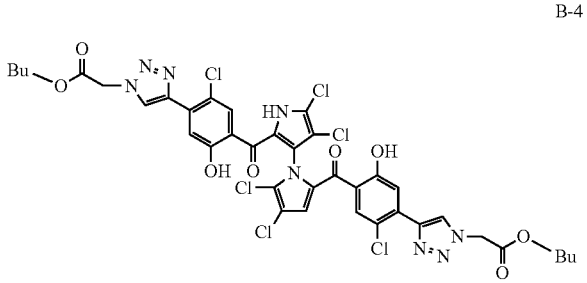

B-4 and (+), (−), and (±) isomers, and pharmaceutically acceptable salts and prodrugs thereof.

In some examples of Formula B-4, the butyl group comprises a tert-butyl group.

In some examples for Formula B, where $R^a$ is Cl and $R^b$ is $CH_2CO_2H$, the compounds are of Formula B-5:

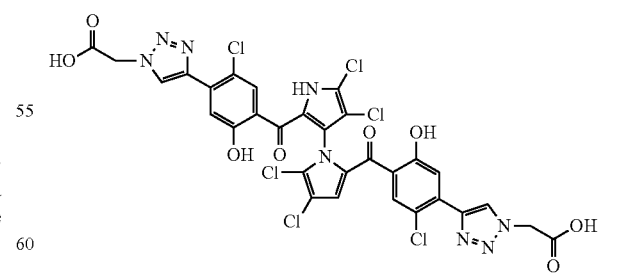

B-5 and (+), (−), and (±) isomers, and pharmaceutically acceptable salts and prodrugs thereof.

In some examples for Formula B, where $R^a$ is H and $R^b$ is $CH_2CO_2CH_2CH_3$, the compounds are of Formula B-6:

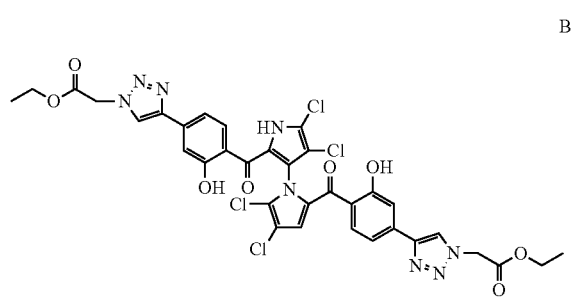

B-6 and (+), (−), and (±) isomers, and pharmaceutically acceptable salts and prodrugs thereof.

In some examples for Formula B, where $R^a$ is H and $R^b$ is $CH_2CO_2Bu$, the compounds are of Formula B-7:

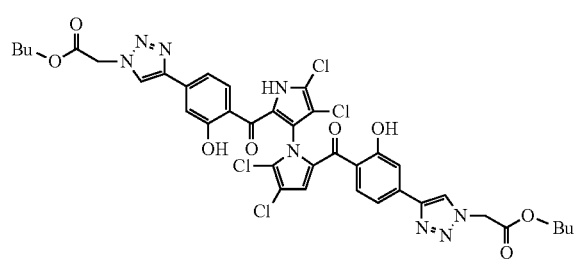

B-7 and (+), (−), and (±) isomers, and pharmaceutically acceptable salts and prodrugs thereof.

In some examples for Formula B-7, the butyl group comprises a tert-butyl group.

In some examples for Formula B, where $R^a$ is H and $R^b$ is $CH_2CO_2H$, the compounds are of Formula B-8:

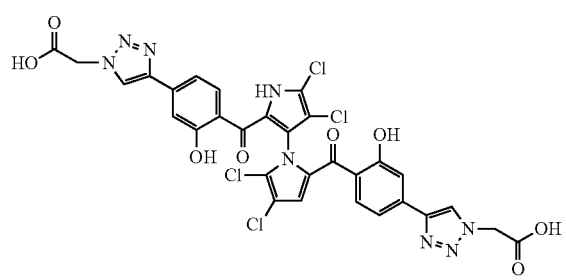

B-8 and (+), (−), and (±) isomers, and pharmaceutically acceptable salts and prodrugs thereof.

In some examples for Formula B, where $R^a$ is H and $R^b$ is $CH_2Ph$, the compounds are of Formula B-9:

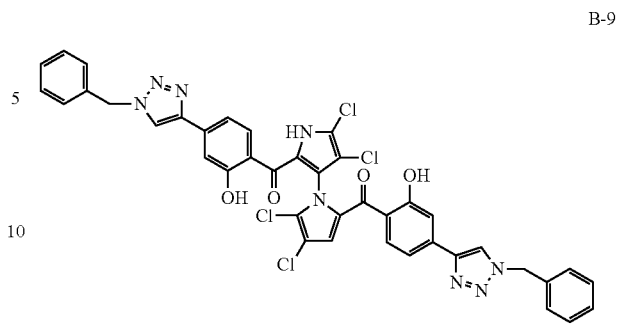

B-9 and (+), (−), and (±) isomers, and pharmaceutically acceptable salts and prodrugs thereof.

In some examples for Formula B, where $R^a$ is H and $R^b$ is Ph, the compounds are of Formula B-10:

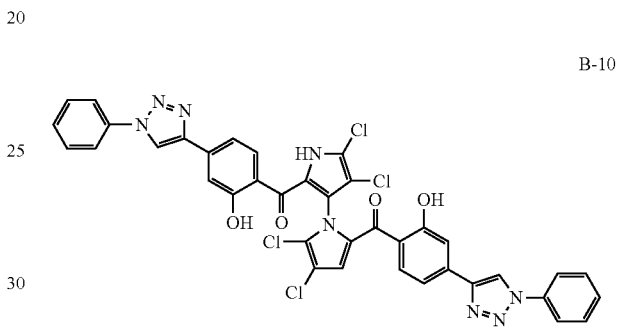

B-10 and (+), (−), and (±) isomers, and pharmaceutically acceptable salts and prodrugs thereof.

In some examples for Formula B, where $R^a$ is H and $R^b$ is cyclohexane, the compounds are of Formula B-11:

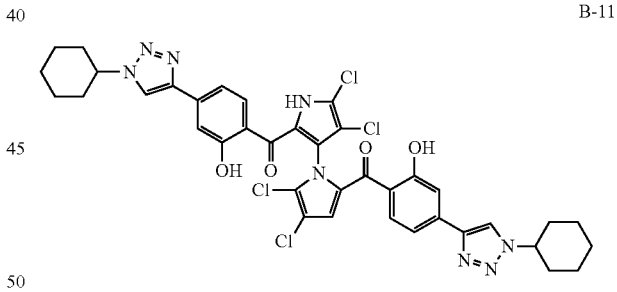

B-11 and (+), (−), and (±) isomers, and pharmaceutically acceptable salts and prodrugs thereof.

In some examples for Formula B, where $R^a$ is H and $R^b$ is n-octane, the compounds are of Formula B-12:

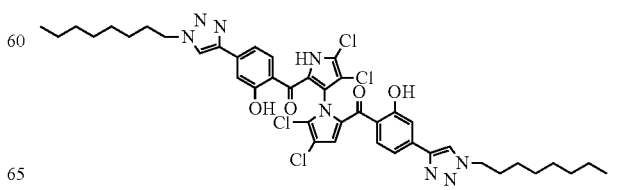

B-12 and (+), (−), and (±) isomers, and pharmaceutically acceptable salts and prodrugs thereof.

Also disclosed are compounds having Formula VI

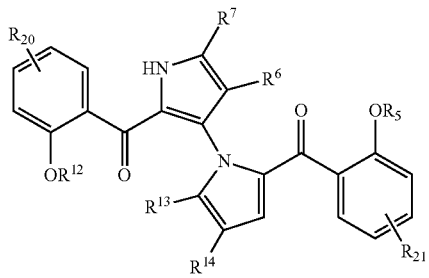

VI wherein $R^6$, $R^7$, $R^{13}$, and $R^{14}$ are independently chosen from hydrogen, halogen, and hydroxyl;

$R^5$ and $R^{12}$ are independently chosen from hydrogen, halogen, and substituted or unsubstituted alkyl;

$R^{20}$ and $R^{21}$ are independently chosen from $SR^{22}$ or $SO_2R^{22}$, where $R^{22}$ is chosen from substituted or unsubstituted alkyl, substituted or unsubstituted amino, substituted or unsubstituted cycloalkyl, substituted or unsubstituted heteroalkyl, substituted or unsubstituted heterocycloalkyl, substituted or unsubstituted alkenyl, substituted or unsubstituted cycloalkenyl, substituted or unsubstituted heteroalkenyl, substituted or unsubstituted heterocycloalkenyl, substituted or unsubstituted alkynyl, substituted or unsubstituted heteroalkynyl, substituted or unsubstituted aryl, substituted or unsubstituted heteroaryl, substituted or unsubstituted alkoxyl, substituted or unsubstituted aryloxyl, and substituted or unsubstituted carboxyl;

and (+), (−), and (±) isomers, and pharmaceutically acceptable salts and prodrugs thereof.

In specific examples of Formula VI, one or both $R^{20}$ and $R^{21}$ are $SO_2$-alkyl (e.g., methyl) substituted with $CO_2H$, $CO_2$alkyl, phenyl, or methoxylphenyl. In other examples of Formula VI, one or both $R^{20}$ and $R^{21}$ are S-alkyl (e.g., methyl) substituted with $CO_2H$, $CO_2$alkyl, phenyl, or methoxylphenyl.

Pharmaceutical Compositions

The compounds described herein or derivatives thereof can be provided in a pharmaceutical composition. Depending on the intended mode of administration, the pharmaceutical composition can be in the form of solid, semi-solid or liquid dosage forms, such as, for example, tablets, suppositories, pills, capsules, powders, liquids, or suspensions, preferably in unit dosage form suitable for single administration of a precise dosage. The compositions will include a therapeutically effective amount of the compound described herein or derivatives thereof in combination with a pharmaceutically acceptable carrier and, in addition, can include other medicinal agents, pharmaceutical agents, carriers, or diluents. By pharmaceutically acceptable is meant a material that is not biologically or otherwise undesirable, which can be administered to an individual along with the selected compound without causing unacceptable biological effects or interacting in a deleterious manner with the other components of the pharmaceutical composition in which it is contained.

As used herein, the term carrier encompasses any excipient, diluent, filler, salt, buffer, stabilizer, solubilizer, lipid, stabilizer, or other material well known in the art for use in pharmaceutical formulations. The choice of a carrier for use in a composition will depend upon the intended route of administration for the composition. The preparation of pharmaceutically acceptable carriers and formulations containing these materials is described in, e.g., *Remington's Pharmaceutical Sciences*, 21st Edition, ed. University of the Sciences in Philadelphia, Lippincott, Williams & Wilkins, Philadelphia Pa., 2005. Examples of physiologically acceptable carriers include saline, glycerol, DMSO, buffers such as phosphate buffers, citrate buffer, and buffers with other organic acids; antioxidants including ascorbic acid; low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as TWEEN™ (ICI, Inc.; Bridgewater, N.J.), polyethylene glycol (PEG), and PLURONICS™ (BASF; Florham Park, N.J.). To provide for the administration of such dosages for the desired therapeutic treatment, compositions disclosed herein can advantageously comprise between about 0.1% and 99% by weight of the total of one or more of the subject compounds based on the weight of the total composition including carrier or diluent.

Compositions containing the compound described herein or derivatives thereof suitable for parenteral injection can comprise physiologically acceptable sterile aqueous or nonaqueous solutions, dispersions, suspensions or emulsions, and sterile powders for reconstitution into sterile injectable solutions or dispersions. Examples of suitable aqueous and nonaqueous carriers, diluents, solvents or vehicles include water, ethanol, polyols (propyleneglycol, polyethyleneglycol, glycerol, and the like), suitable mixtures thereof, vegetable oils (such as olive oil) and injectable organic esters such as ethyl oleate. Proper fluidity can be maintained, for example, by the use of a coating such as lecithin, by the maintenance of the required particle size in the case of dispersions and by the use of surfactants.

These compositions can also contain adjuvants such as preserving, wetting, emulsifying, and dispensing agents. Prevention of the action of microorganisms can be promoted by various antibacterial and antifungal agents, for example, parabens, chlorobutanol, phenol, sorbic acid, and the like. Isotonic agents, for example, sugars, sodium chloride, and the like can also be included. Prolonged absorption of the injectable pharmaceutical form can be brought about by the use of agents delaying absorption, for example, aluminum monostearate and gelatin.

Solid dosage forms for oral administration of the compounds described herein or derivatives thereof include capsules, tablets, pills, powders, and granules. In such solid dosage forms, the compounds described herein or derivatives thereof is admixed with at least one inert customary excipient (or carrier) such as sodium citrate or dicalcium phosphate or (a) fillers or extenders, as for example, starches, lactose, sucrose, glucose, mannitol, and silicic acid, (b) binders, as for example, carboxymethylcellulose, alignates, gelatin, polyvinylpyrrolidone, sucrose, and acacia, (c) humectants, as for example, glycerol, (d) disintegrating agents, as for example, agar-agar, calcium carbonate, potato or tapioca starch, alginic acid, certain complex silicates, and sodium carbonate, (e) solution retarders, as for example, paraffin, (f) absorption accelerators, as for example, quaternary ammonium compounds, (g) wetting agents, as for example, cetyl alcohol, and glycerol monostearate, (h) adsorbents, as for example, kaolin and bentonite, and (i) lubricants, as for example, talc, calcium stearate, magnesium stearate, solid polyethylene glycols, sodium lauryl sulfate, or mixtures thereof. In the case of capsules, tablets, and pills, the dosage forms can also comprise buffering agents.

Solid compositions of a similar type can also be employed as fillers in soft and hard-filled gelatin capsules using such excipients as lactose or milk sugar as well as high molecular weight polyethyleneglycols, and the like.

Solid dosage forms such as tablets, dragees, capsules, pills, and granules can be prepared with coatings and shells, such as enteric coatings and others known in the art. They can contain opacifying agents and can also be of such composition that they release the active compound or compounds in a certain part of the intestinal tract in a delayed manner. Examples of embedding compositions that can be used are polymeric substances and waxes. The active compounds can also be in micro-encapsulated form, if appropriate, with one or more of the above-mentioned excipients. The disclosed compounds can also be incorporated into polymers, examples of which include poly (D-L lactide-co-glycolide) polymer for intracranial tumors; poly[bis(pcarboxyphenoxy) propane:sebacic acid] in a 20:80 molar ratio (as used in GLIADEL); chondroitin; chitin; and chitosan.

Liquid dosage forms for oral administration of the compounds described herein or derivatives thereof include pharmaceutically acceptable emulsions, solutions, suspensions, syrups, and elixirs. In addition to the active compounds, the liquid dosage forms can contain inert diluents commonly used in the art, such as water or other solvents, solubilizing agents, and emulsifiers, as for example, ethyl alcohol, isopropyl alcohol, ethyl carbonate, ethyl acetate, benzyl alcohol, benzyl benzoate, propyleneglycol, 1,3-butyleneglycol, dimethylformamide, oils, in particular, cottonseed oil, groundnut oil, corn germ oil, olive oil, castor oil, sesame oil, glycerol, tetrahydrofurfuryl alcohol, polyethyleneglycols, and fatty acid esters of sorbitan, or mixtures of these substances, and the like.

Besides such inert diluents, the composition can also include additional agents, such as wetting, emulsifying, suspending, sweetening, flavoring, or perfuming agents.

Suspensions, in addition to the active compounds, can contain additional agents, as for example, ethoxylated isostearyl alcohols, polyoxyethylene sorbitol and sorbitan esters, microcrystalline cellulose, aluminum metahydroxide, bentonite, agar-agar and tragacanth, or mixtures of these substances, and the like.

Compositions of the compounds described herein or derivatives thereof for rectal administrations are optionally suppositories, which can be prepared by mixing the compounds with suitable non-irritating excipients or carriers such as cocoa butter, polyethyleneglycol or a suppository wax, which are solid at ordinary temperatures but liquid at body temperature and therefore, melt in the rectum or vaginal cavity and release the active component.

Dosage forms for topical administration of the compounds described herein or derivatives thereof include ointments, powders, sprays, and inhalants. The compounds described herein or derivatives thereof are admixed under sterile conditions with a physiologically acceptable carrier and any preservatives, buffers, or propellants as can be required. Ophthalmic formulations, ointments, powders, and solutions are also contemplated as being within the scope of the compositions.

The compositions can include one or more of the compounds described herein and a pharmaceutically acceptable carrier. As used herein, the term pharmaceutically acceptable salt refers to those salts of the compound described herein or derivatives thereof that are, within the scope of sound medical judgment, suitable for use in contact with the tissues of subjects without undue toxicity, irritation, allergic response, and the like, commensurate with a reasonable benefit/risk ratio, and effective for their intended use, as well as the zwitterionic forms, where possible, of the compounds described herein. The term salts refers to the relatively non-toxic, inorganic and organic acid addition salts of the compounds described herein. These salts can be prepared in situ during the isolation and purification of the compounds or by separately reacting the purified compound in its free base form with a suitable organic or inorganic acid and isolating the salt thus formed. Representative salts include the hydrobromide, hydrochloride, sulfate, bisulfate, nitrate, acetate, oxalate, valerate, oleate, palmitate, stearate, laurate, borate, benzoate, lactate, phosphate, tosylate, citrate, maleate, fumarate, succinate, tartrate, naphthylate mesylate, glucoheptonate, lactobionate, methane sulphonate, and laurylsulphonate salts, and the like. These can include cations based on the alkali and alkaline earth metals, such as sodium, lithium, potassium, calcium, magnesium, and the like, as well as non-toxic ammonium, quaternary ammonium, and amine cations including, but not limited to ammonium, tetramethylammonium, tetraethylammonium, methylamine, dimethylamine, trimethylamine, triethylamine, ethylamine, and the like. (See S. M. Barge et al., *J. Pharm. Sci.* (1977) 66, 1, which is incorporated herein by reference in its entirety, at least, for compositions taught herein.)

Administration of the compounds and compositions described herein or pharmaceutically acceptable salts thereof to a subject can be carried out using therapeutically effective amounts of the compounds and compositions described herein or pharmaceutically acceptable salts thereof as described herein for periods of time effective to treat a disorder.

The effective amount of the compounds and compositions described herein or pharmaceutically acceptable salts thereof as described herein can be determined by one of ordinary skill in the art and includes exemplary dosage amounts for a mammal of from about 0.5 to about 200 mg/kg of body weight of active compound per day, which can be administered in a single dose or in the form of individual divided doses, such as from 1 to 4 times per day. Alternatively, the dosage amount can be from about 0.5 to about 150 mg/kg of body weight of active compound per day, about 0.5 to 100 mg/kg of body weight of active compound per day, about 0.5 to about 75 mg/kg of body weight of active compound per day, about 0.5 to about 50 mg/kg of body weight of active compound per day, about 0.5 to about 25 mg/kg of body weight of active compound per day, about 1 to about 20 mg/kg of body weight of active compound per day, about 1 to about 10 mg/kg of body weight of active compound per day, about 20 mg/kg of body weight of active compound per day, about 10 mg/kg of body weight of active compound per day, or about 5 mg/kg of body weight of active compound per day. The expression effective amount, when used to describe an amount of compound in a method, refers to the amount of a compound that achieves the desired pharmacological effect or other effect, for example an amount that results in enzyme inhibition.

Those of skill in the art will understand that the specific dose level and frequency of dosage for any particular subject can be varied and will depend upon a variety of factors, including the activity of the specific compound employed, the metabolic stability and length of action of that compound, the species, age, body weight, general health, sex and diet of the subject, the mode and time of administration, rate of excretion, drug combination, and severity of the particular condition.

Methods of Making the Compounds

The compounds described herein can be prepared in a variety of ways known to one skilled in the art of organic synthesis or variations thereon as appreciated by those skilled in the art. The compounds described herein can be prepared from readily available starting materials. Optimum reaction conditions can vary with the particular reactants or solvents used, but such conditions can be determined by one skilled in the art.

Variations on the compounds discussed herein include the addition, subtraction, or movement of the various constituents as described for each compound. Similarly, when one or more chiral centers are present in a molecule, the chirality of the molecule can be changed. Additionally, compound synthesis can involve the protection and deprotection of various chemical groups. The use of protection and deprotection, and the selection of appropriate protecting groups can be determined by one skilled in the art. The chemistry of protecting groups can be found, for example, in Wuts and Greene, Protective Groups in Organic Synthesis, 4th Ed., Wiley & Sons, 2006, which is incorporated herein by reference in its entirety.

The starting materials and reagents used in preparing the disclosed compounds and compositions are either available from commercial suppliers such as Aldrich Chemical Co., (Milwaukee, Wis.), Acros Organics (Morris Plains, N.J.), Fisher Scientific (Pittsburgh, Pa.), Sigma (St. Louis, Mo.), Pfizer (New York, N.Y.), GlaxoSmithKline (Raleigh, N.C.), Merck (Whitehouse Station, N.J.), Johnson & Johnson (New Brunswick, N.J.), Aventis (Bridgewater, N.J.), AstraZeneca (Wilmington, Del.), Novartis (Basel, Switzerland), Wyeth (Madison, N.J.), Bristol-Myers-Squibb (New York, N.Y.), Roche (Basel, Switzerland), Lilly (Indianapolis, Ind.), Abbott (Abbott Park, Ill.), Schering Plough (Kenilworth, N.J.), or Boehringer Ingelheim (Ingelheim, Germany), or are prepared by methods known to those skilled in the art following procedures set forth in references such as Fieser and Fieser's Reagents for Organic Synthesis, Volumes 1-17 (John Wiley and Sons, 1991); Rodd's Chemistry of Carbon Compounds, Volumes 1-5 and Supplementals (Elsevier Science Publishers, 1989); Organic Reactions, Volumes 1-40 (John Wiley and Sons, 1991); March's Advanced Organic Chemistry, (John Wiley and Sons, 4th Edition); and Larock's Comprehensive Organic Transformations (VCH Publishers Inc., 1989). Other materials, such as the pharmaceutical carriers disclosed herein can be obtained from commercial sources.

Reactions to produce the compounds described herein can be carried out in solvents, which can be selected by one of skill in the art of organic synthesis. Solvents can be substantially nonreactive with the starting materials (reactants), the intermediates, or products under the conditions at which the reactions are carried out, i.e., temperature and pressure. Reactions can be carried out in one solvent or a mixture of more than one solvent. Product or intermediate formation can be monitored according to any suitable method known in the art. For example, product formation can be monitored by spectroscopic means, such as nuclear magnetic resonance spectroscopy (e.g., $^1$H or $^{13}$C) infrared spectroscopy, spectrophotometry (e.g., UV-visible), or mass spectrometry, or by chromatography such as high performance liquid chromatography (HPLC) or thin layer chromatography.

Activity Assays

The activity of the compounds provided herein as anticancer agents can be measured in standard assays, e.g., HPLC assays. The activities of the compounds as determined using the assays described herein can be reported in terms of $IC_{50}$. As used herein, $IC_{50}$ refers to an amount, concentration, or dosage of a particular test compound that achieves a 50% inhibition of a maximal response in an assay that measures such response.

In certain aspects, the disclosed compounds and compositions need not actually be synthesized, but instead can be used as targets for any molecular modeling technique to predict and characterize interactions with cancer associated enzymes. This is achieved through structural information and computer modeling. Computer modeling technology allows visualization of the three-dimensional atomic structure of a selected molecule and the rational design of new compounds that will interact with an enzyme. The three-dimensional construct of the enzyme typically depends on data from x-ray crystallographic analyses or NMR imaging of the selected molecule. The molecular dynamics require force field data (e.g., Merck Molecular Force Field). The computer graphics systems enable prediction of how a new compound will link to the enzyme and allow experimental manipulation of the structures of the compound to perfect binding specificity. Prediction of what the interactions will be when small changes are made in one or both requires molecular mechanics software and computationally intensive computers, usually coupled with user-friendly, menu-driven interfaces between the molecular design program and the user.

Examples of molecular modeling systems are the CHARMm and QUANTA programs, Polygen Corporation, Waltham, Mass. CHARMm performs the energy minimization and molecular dynamics functions. QUANTA performs the construction, graphic modeling and analysis of molecular structure. QUANTA allows interactive construction, modification, visualization, and analysis of the behavior of molecules with each other. Upon identification of compounds that interact in a desired way with the enzyme in silico, actual compounds can be synthesized and assayed as disclosed herein.

The activity of the compounds provided herein as antibacterial agents can be measured in standard assays, e.g., HPLC assays. The compounds can also be evaluated for antibacterial activity using the Mueller Hinton (MH) broth antibacterial assay as specified by the Clinical and Laboratory Standards Institute MIC broth microdilution protocol (see Methods for Dilution Antimicrobial Susceptibility Tests for Bacteria That Grow Aerobically; Approved Standard, In *The Clinical and Laboratory Standards Institute (CLSI, formerly NCCLS)*, 7th ed., January 2006, 26 (2), M7-A7; see also Performance Standards for Antimicrobial Susceptibility Testing; Eighteenth Informational Supplement, In *The Clinical and Laboratory Standards Institute (CLSI, formerly NCCLS)*, January 2008, 28 (1), M100-S18.

The activities of the compounds as determined using the assays described herein can be reported in terms of $IC_{50}$ and/or MIC 100. As used herein, $IC_{50}$ refers to an amount, concentration or dosage of a particular test compound that achieves a 50% inhibition of a maximal response in an assay that measures such response. MIC 100 is used to measure the growth inhibition of cells and refers to a 100% inhibition of cell growth.

In certain aspects, the disclosed compounds and compositions need not actually be synthesized, but instead can be used as targets for any molecular modeling technique to predict and characterize interactions with bacterial enzymes. This is achieved through structural information and computer modeling. Computer modeling technology allows visualization of the three-dimensional atomic structure of a selected molecule and the rational design of new compounds that will interact with a bacterial enzyme. The three-dimensional construct of the enzyme typically depends on data from x-ray crystallographic analyses or NMR imaging of the selected molecule. The molecular dynamics require force field data (e.g., Merck Molecular Force Field). The computer graphics systems enable prediction of how a new compound will link to the enzyme and allow experimental manipulation of the structures of the compound to perfect binding specificity. Prediction of what the interactions will be when small changes are made in one or both requires molecular mechanics software and computationally intensive computers, usually coupled with user-friendly, menu-driven interfaces between the molecular design program and the user.

Examples of molecular modeling systems are the CHARMm and QUANTA programs, Polygen Corporation, Waltham, Mass. CHARMm performs the energy minimization and molecular dynamics functions. QUANTA performs the construction, graphic modeling and analysis of molecular structure. QUANTA allows interactive construction, modification, visualization, and analysis of the behavior of molecules with each other. Upon identification of compounds that interact in a desired way with the bacterial enzyme in silico, actual compounds can be synthesized and assayed as disclosed herein.

Methods of Use

Marinopyrroles were reported to show antibiotic activity against methicillin-resistant *Staphylococcus aureus* (MRSA) in 2008 by the Fenical group (Hughes C C et al. *Org. Lett.* 2008, 10, 629-631). Due to their molecular structures and promising biological properties, marinopyrroles have attracted considerable attention (Hughes C C et al. *J. Org. Chem.* 2010, 75, 3240-3250; Cheng C et al. *J. Comb. Chem.* 2010, 12, 541-547; Kanakis A A and Sarli V. *Org. Lett.* 2010, 12, 4872-4875; Nicolaou K C et al. *Tetrahedron Lett.* 2011, 52, 2041-2043; Liu Y et al. *Mar. Drugs* 2012, 10, 953-962; Pan L et al. *Chem. J. Chinese Universities* 2012, 33, 1476-1480; Yamanaka K et al. *J. Am. Chem. Soc.* 2012, 134, 12434-12437; Cheng P et al. *Chem. Commun.* 2013, 49, 558-560; Clive D L J and Cheng, P. *Tetrahedron* 2013, 69, 5067-5078; Cheng C et al. *Mar. Drugs* 2013, 11, 2927-2948). The total synthesis of (±)-marinopyrrole A (1) was reported along with 12 derivatives in early 2010 (Cheng C et al. *J. Comb. Chem.* 2010, 12, 541-547). This was soon followed by a report of the synthesis of (±)-marinopyrrole A via an intermolecular Ullman coupling to form the bispyrrole system (Kanakis A A and Sarli V. *Org. Lett.* 2010, 12, 4872-4875). A five-step method to access marinopyrrole derivatives, (+)-1 and (−)-1 atropisomers after a chiral separation of (±)-1 using HPLC, as well as their antibiotic activities against MRSA was reported in 2011 (Nicolaou K C et al. *Tetrahedron Lett.* 2011, 52, 2041-2043). Afterwards, a biosynthetic approach toward marinopyrrole A via an N, C-bispyrrole homocoupling catalyzed by two flavin-dependent halogenases was described (Yamanaka K et al. *J. Am. Chem. Soc.* 2012, 134, 12434-12437). More recently, the total synthesis of marinopyrrole B and a review of the marinopyrroles were reported (Cheng P et al. *Chem. Commun.* 2013, 49, 558-560; Clive D L J and Cheng, P. *Tetrahedron* 2013, 69, 5067-5078). After the synthesis of a series of "non-symmetrical" marinopyrrole derivatives and their antibiotic activities was reported (Liu Y et al. *Mar. Drugs* 2012, 10, 953-962), optimization studies of the steps to avoid the formation of oxazepine byproduct was reported (Pan L et al. *Chem. J. Chinese Universities* 2012, 33, 1476-1480). Most recently, potent marinopyrrole derivatives against MRSA were reported (Cheng C et al. *Mar. Drugs* 2013, 11, 2927-2948). Furthermore, it was also reported was that (±)-marinopyrrole A antagonizes Mcl-1 and overcomes resistance of human cancer cells to the Bcl-$x_L$ antagonist ABT-737 (Doi K et al. *J. Biol. Chem.* 2012, 287, 10224-10235). A selective Mcl-1 small-molecule inhibitor blocking pancreatic cancer growth in vitro and in vivo resulted from high throughput screening followed by structure-based chemical optimization was reported recently (Abulwerdi F et al. *Mol. Cancer Ther.* 2013, published OnlineFirst Sep. 9, 2013. doi: 10.1158/1535-7163.MCT-12-0767).

Provided herein are methods of treating, preventing, or ameliorating cancer in a subject. The methods include administering to a subject an effective amount of one or more of the compounds or compositions described herein, or a pharmaceutically acceptable salt thereof. The compounds and compositions described herein or pharmaceutically acceptable salts thereof are useful for treating cancer in humans, e.g., pediatric and geriatric populations, and in animals, e.g., veterinary applications. The disclosed methods can optionally include identifying a patient who is or can be in need of treatment of a cancer. Examples of cancer types treatable by the compounds and compositions described herein include bladder cancer, brain cancer, breast cancer, colorectal cancer, cervical cancer, gastrointestinal cancer, genitourinary cancer, head and neck cancer, lung cancer, ovarian cancer, pancreatic cancer, prostate cancer, renal cancer, skin cancer, and testicular cancer. Further examples include cancer and/or tumors of the anus, bile duct, bone, bone marrow, bowel (including colon and rectum), eye, gall bladder, kidney, mouth, larynx, esophagus, stomach, testis, cervix, mesothelioma, neuroendocrine, penis, skin, spinal cord, thyroid, vagina, vulva, uterus, liver, muscle, blood cells (including lymphocytes and other immune system cells). Some examples of cancers contemplated for treatment include carcinomas, Karposi's sarcoma, melanoma, mesothelioma, soft tissue sarcoma, pancreatic cancer, lung cancer, leukemia (acute lymphoblastic, acute myeloid, chronic lymphocytic, chronic myeloid, and other), and lymphoma (Hodgkin's and non-Hodgkin's), and multiple myeloma.

The methods of treatment or prevention described herein can further include treatment with one or more additional agents (e.g., an anti-cancer agent or ionizing radiation). The one or more additional agents and the compounds and compositions or pharmaceutically acceptable salts thereof as described herein can be administered in any order, including simultaneous administration, as well as temporally spaced order of up to several days apart. The methods can also include more than a single administration of the one or more additional agents and/or the compounds and compositions or pharmaceutically acceptable salts thereof as described herein. The administration of the one or more additional agents and the compounds and compositions or pharmaceutically acceptable salts thereof as described herein can be by the same or different routes. When treating with one or more additional agents, the compounds and compositions or pharmaceutically acceptable salts thereof as described herein can be combined into a pharmaceutical composition that includes the one or more additional agents.

For example, the compounds or compositions or pharmaceutically acceptable salts thereof as described herein can be combined into a pharmaceutical composition with an additional anti-cancer agent, such as 13-cis-Retinoic Acid, 2-Amino-6-Mercaptopurine, 2-CdA, 2-Chlorodeoxyadenosine, 5-fluorouracil, 6-Thioguanine, 6-Mercaptopurine, Accutane, Actinomycin-D, Adriamycin, Adrucil, Agrylin, Ala-Cort, Aldesleukin, Alemtuzumab, Alitretinoin, Alkaban-AQ, Alkeran, All-transretinoic acid, Alpha interferon, Altretamine, Amethopterin, Amifostine, Aminoglutethimide, Anagrelide, Anandron, Anastrozole, Arabinosylcytosine, Aranesp, Aredia, Arimidex, Aromasin, Arsenic trioxide, Asparaginase, ATRA, Avastin, BCG, BCNU, Bevacizumab, Bexarotene, Bicalutamide, BiCNU, Blenoxane, Bleomycin, Bortezomib, Busulfan, Busulfex, C225, Calcium Leucovorin, Campath, Camptosar, Camptothecin-11, Capecitabine, Carac, Carboplatin, Carmustine, Carmustine wafer, Casodex, CCNU, CDDP, CeeNU, Cerubidine, cetuximab, Chlorambucil, Cisplatin, Citrovorum Factor, Cladribine, Cortisone, Cosmegen, CPT-11, Cyclophosphamide, Cytadren, Cytarabine, Cytarabine liposomal, Cytosar-U, Cytoxan, Dacarbazine, Dactinomycin, Darbepoetin alfa, Daunomycin, Daunorubicin, Daunorubicin hydrochloride, Daunorubicin liposomal, DaunoXome, Decadron, Delta-Cortef, Deltasone, Denileukin diftitox, DepoCyt, Dexamethasone, Dexamethasone acetate, Dexamethasone sodium phosphate, Dexasone, Dexrazoxane, DHAD, DIC, Diodex, Docetaxel, Doxil, Doxorubicin, Doxorubicin liposomal, Droxia, DTIC, DTIC-Dome, Duralone, Efudex, Eligard, Ellence, Eloxatin, Elspar, Emcyt, Epirubicin, Epoetin alfa, Erbitux, Erwinia L-asparaginase, Estramustine, Ethyol, Etopophos, Etoposide, Etoposide phosphate, Eulexin, Evista, Exemestane, Fareston, Faslodex, Femara, Filgrastim, Floxuridine, Fludara, Fludarabine, Fluoroplex, Fluorouracil, Fluorouracil (cream), Fluoxymesterone, Flutamide, Folinic Acid, FUDR, Fulvestrant, G-CSF, Gefitinib, Gemcitabine, Gemtuzumab ozogamicin, Gemzar, Gleevec, Lupron, Lupron Depot, Matulane, Maxidex, Mechlorethamine, -Mechlorethamine Hydrochlorine, Medralone, Medrol, Megace, Megestrol, Megestrol Acetate, Melphalan, Mercaptopurine, Mesna, Mesnex, Methotrexate, Methotrexate Sodium, Methylprednisolone, Mylocel, Letrozole, Neosar, Neulasta, Neumega, Neupogen, Nilandron, Nilutamide, Nitrogen Mustard, Novaldex, Novantrone, Octreotide, Octreotide acetate, Oncospar, Oncovin, Ontak, Onxal, Oprevelkin, Orapred, Orasone, Oxaliplatin, Paclitaxel, Pamidronate, Panretin, Paraplatin, Pediapred, PEG Interferon, Pegaspargase, Pegfilgrastim, PEG-INTRON, PEG-L-asparaginase, Phenylalanine Mustard, Platinol, Platinol-AQ, Prednisolone, Prednisone, Prelone, Procarbazine, PROCRIT, Proleukin, Prolifeprospan 20 with Carmustine implant, Purinethol, Raloxifene, Rheumatrex, Rituxan, Rituximab, Roveron-A (interferon alfa-2a), Rubex, Rubidomycin hydrochloride, Sandostatin, Sandostatin LAR, Sargramostim, Solu-Cortef, Solu-Medrol, STI-571, Streptozocin, Tamoxifen, Targretin, Taxol, Taxotere, Temodar, Temozolomide, Teniposide, TESPA, Thalidomide, Thalomid, TheraCys, Thioguanine, Thioguanine Tabloid, Thiophosphoamide, Thioplex, Thiotepa, TICE, Toposar, Topotecan, Toremifene, Trastuzumab, Tretinoin, Trexall, Trisenox, TSPA, VCR, Velban, Velcade, VePesid, Vesanoid, Viadur, Vinblastine, Vinblastine Sulfate, Vincasar Pfs, Vincristine, Vinorelbine, Vinorelbine tartrate, VLB, VP-16, Vumon, Xeloda, Zanosar, Zevalin, Zinecard, Zoladex, Zoledronic acid, Zometa, Gliadel wafer, Glivec, GM-CSF, Goserelin, granulocyte colony stimulating factor, Halotestin, Herceptin, Hexadrol, Hexalen, Hexamethylmelamine, HMM, Hycamtin, Hydrea, Hydrocort Acetate, Hydrocortisone, Hydrocortisone sodium phosphate, Hydrocortisone sodium succinate, Hydrocortone phosphate, Hydroxyurea, Ibritumomab, Ibritumomab Tiuxetan, Idamycin, Idarubicin, Ifex, IFN-alpha, Ifosfamide, IL 2, IL-11, Imatinib mesylate, Imidazole Carboxamide, Interferon alfa, Interferon Alfa-2b (PEG conjugate), Interleukin 2, Interleukin-11, Intron A (interferon alfa-2b), Leucovorin, Leukeran, Leukine, Leuprolide, Leurocristine, Leustatin, Liposomal Ara-C, Liquid Pred, Lomustine, L-PAM, L-Sarcolysin, Meticorten, Mitomycin, Mitomycin-C, Mitoxantrone, M-Prednisol, MTC, MTX, Mustargen, Mustine, Mutamycin, Myleran, Iressa, Irinotecan, Isotretinoin, Kidrolase, Lanacort, L-asparaginase, and LCR. The additional anti-cancer agent can also include biopharmaceuticals such as, for example, antibodies.

Further, the additional agent can include ABT-263 (CAS#923564-51-6) also known as navitoclax and/or ABT-737 (CAS#852808-04-9), both of which are commercially. Still further the disclosed compositions can further include compounds that inhibit transcription of Mcl-1, such as with the cyclin-dependent kinase inhibitors Seliciclib (CAS#186692-46-6) and Flavopiridol (CAS#146426-40-6) or translation, such as with the multikinase inhibitor BAY 43-9006 (CAS#284461-73-0). Further examples of additional compounds that can be present in the disclosed compositions include, but are not limited to, dexamethasone (CAS#50-02-2), melphalan (CAS#148-82-3), obatoclax (CAS#803712-67-6), BH3-M6, and gossypol (CAS#303-45-7).

Many tumors and cancers have viral genome present in the tumor or cancer cells. For example, Epstein-Barr Virus (EBV) is associated with a number of mammalian malignancies. The compounds disclosed herein can also be used alone or in combination with anticancer or antiviral agents, such as ganciclovir, azidothymidine (AZT), lamivudine (3TC), etc., to treat patients infected with a virus that can cause cellular transformation and/or to treat patients having a tumor or cancer that is associated with the presence of viral genome in the cells. The compounds disclosed herein can also be used in combination with viral based treatments of oncologic disease. For example, the compounds can be used with mutant herpes simplex virus in the treatment of non-small cell lung cancer (Toyoizumi, et al., "Combined therapy with chemotherapeutic agents and herpes simplex virus type IICP34.5 mutant (HSV-1716) in human non-small cell lung cancer," *Human Gene Therapy*, 1999, 10(18):17).

Also described herein are methods of killing a tumor cell in a subject. The method includes contacting the tumor cell with an effective amount of a compound or composition as described herein, and optionally includes the step of irradiating the tumor cell with an effective amount of ionizing radiation. Additionally, methods of radiotherapy of tumors are provided herein. The methods include contacting the tumor cell with an effective amount of a compound or composition as described herein, and irradiating the tumor with an effective amount of ionizing radiation. As used herein, the term ionizing radiation refers to radiation comprising particles or photons that have sufficient energy or can produce sufficient energy via nuclear interactions to produce ionization. An example of ionizing radiation is x-radiation. An effective amount of ionizing radiation refers to a dose of ionizing radiation that produces an increase in cell damage or death when administered in combination with the compounds described herein. The ionizing radiation can be delivered according to methods as known in the art, including administering radiolabeled antibodies and radioisotopes.

The methods and compounds as described herein are useful for both prophylactic and therapeutic treatment. As used herein the term treating or treatment includes prevention; delay in onset; diminution, eradication, or delay in exacerbation of signs or symptoms after onset; and prevention of relapse. For prophylactic use, a therapeutically effective amount of the compounds and compositions or pharmaceutically acceptable salts thereof as described herein are administered to a subject prior to onset (e.g., before obvious signs of cancer), during early onset (e.g., upon initial signs and symptoms of cancer), or after an established development of cancer. Prophylactic administration can occur for several days to years prior to the manifestation of symptoms of an infection. Prophylactic administration can be used, for example, in the chemopreventative treatment of subjects presenting precancerous lesions, those diagnosed with early stage malignancies, and for subgroups with susceptibilities (e.g., family, racial, and/or occupational) to particular cancers. Therapeutic treatment involves administering to a subject a therapeutically effective amount of the compounds and compositions or pharmaceutically acceptable salts thereof as described herein after cancer is diagnosed.

In some examples, the compounds disclosed herein are effective at inhibiting Mcl-1. In some examples, the compounds disclosed herein can be used for treating cancers where Mcl-1 is expressed or over expressed, and killing Mcl-1 dependent cells.

Also provided herein are methods to treat, prevent, or limit microbial infections in a subject. The methods include administering to a subject an effective amount of one or more of the compounds or compositions described herein, or a pharmaceutically acceptable salt thereof. The compounds and compositions described herein or pharmaceutically acceptable salts thereof are useful for treating microbial infections and cancer in humans, e.g., pediatric and geriatric populations, and in animals, e.g., veterinary applications. Microbial infections include, for example, bacterial and fungal infections. Bacterial infections include infections caused by bacilli, cocci, spirochaetes, and vibrio bacteria. In some examples, the microbial infection is a bacterial infection (e.g., a Gram positive bacterial infection). In some examples, the bacterial infection is *Staphylococcus* infection, such as a *Staphylococcus aureus*. The compounds and compositions described herein are useful in treating a variety of *Staphylococcus aureus* infections, including drug-resistant *Staphylococcus aureus* infections and biofilm-associated *Staphylococcus aureus* infections. In some embodiments, the *Staphylococcus aureus* infection is methocillin-resistant *S. aureus* (MRSA). For example, the MRSA can be hospital-associated MRSA or community associated MRSA.

The methods of treatment or prevention described herein can further include treatment with one or more additional agents (e.g., an antibacterial agent). The one or more additional agents and the compounds and compositions or pharmaceutically acceptable salts thereof as described herein can be administered in any order, including simultaneous administration, as well as temporally spaced order of up to several days apart. The methods can also include more than a single administration of the one or more additional agents and/or the compounds and compositions or pharmaceutically acceptable salts thereof as described herein. The administration of the one or more additional agents and the compounds and compositions or pharmaceutically acceptable salts thereof as described herein can be by the same or different routes. When treating with one or more additional agents, the compounds and compositions or pharmaceutically acceptable salts thereof as described herein can be combined into a pharmaceutical composition that includes the one or more additional agents. For example, the compounds or compositions or pharmaceutically acceptable salts thereof as described herein can be combined into a pharmaceutical composition with an additional antibacterial agent, such as acedapsone; acetosulfone sodium; alamecin; alexidine; amdinocillin; amdinocillin pivoxil; amicycline; amifloxacin; amifloxacin mesylate; amikacin; amikacin sulfate; aminosalicylic acid; aminosalicylate sodium; amoxicillin; amphomycin; ampicillin; ampicillin sodium; apalcillin sodium; apramycin; aspartocin; astromicin sulfate; avilamycin; avoparcin; azithromycin; azlocillin; azlocillin sodium; bacampicillin hydrochloride; bacitracin; bacitracin methylene disalicylate; bacitracin zinc; bambermycins; benzoylpas calcium; berythromycin; betamicin sulfate; biapenem; biniramycin; biphenamine hydrochloride; bispyrithione magsulfex; butikacin; butirosin sulfate; capreomycin sulfate; carbadox; carbenicillin disodium; carbenicillin indanyl sodium; carbenicillin phenyl sodium; carbenicillin potassium; carumonam sodium; cefaclor; cefadroxil; cefamandole; cefamandole nafate; cefamandole sodium; cefaparole; cefatrizine; cefazaflur sodium; cefazolin; cefazolin sodium; cefbuperazone; cefdinir; cefepime; cefepime hydrochloride; cefetecol; cefixime; cefmenoxime hydrochloride; cefmetazole; cefmetazole sodium; cefonicid monosodium; cefonicid sodium; cefoperazone sodium; ceforanide; cefotaxime sodium; cefotetan; cefotetan disodium; cefotiam hydrochloride; cefoxitin; cefoxitin sodium; cefpimizole; cefpimizole sodium; cefpiramide; cefpiramide sodium; cefpirome sulfate; cefpodoxime proxetil; cefprozil; cefroxadine; cefsulodin sodium; ceftazidime; ceftibuten; ceftizoxime sodium; ceftriaxone sodium; cefuroxime; cefuroxime axetil; cefuroxime pivoxetil; cefuroxime sodium; cephacetrile sodium; cephalexin; cephalexin hydrochloride; cephaloglycin; cephaloridine; cephalothin sodium; cephapirin sodium; cephradine; cetocycline hydrochloride; cetophenicol; chloramphenicol; chloramphenicol palmitate; chloramphenicol pantothenate complex; chloramphenicol sodium succinate; chlorhexidine phosphanilate; chloroxylenol; chlortetracycline bisulfate; chlortetracycline hydrochloride; cinoxacin; ciprofloxacin; ciprofloxacin hydrochloride; cirolemycin; clarithromycin; clinafloxacin hydrochloride; clindamycin; clindamycin hydrochloride; clindamycin palmitate hydrochloride; clindamycin phosphate; clofazimine; cloxacillin benzathine; cloxacillin sodium; cloxyquin; colistimethate sodium; colistin sulfate; coumermycin; coumermycin sodium; cyclacillin; cycloserine; dalfopristin; dapsone; daptomycin; demeclocycline; demeclocycline hydrochloride; demecycline; denofungin; diaveridine; dicloxacillin; dicloxacillin sodium; dihydrostreptomycin sulfate; dipyrithione; dirithromycin; doxycycline; doxycycline calcium; doxycycline fosfatex; doxycycline hyclate; droxacin sodium; enoxacin; epicillin; epitetracycline hydrochloride; erythromycin; erythromycin acistrate; erythromycin estolate; erythromycin ethylsuccinate; erythromycin gluceptate; erythromycin lactobionate; erythromycin propionate; erythromycin stearate; ethambutol hydrochloride; ethionamide; fleroxacin; floxacillin; fludalanine; flumequine; fosfomycin; fosfomycin tromethamine; fumoxicillin; furazolium chloride; furazolium tartrate; fusidate sodium; fusidic acid; gentamicin sulfate; gloximonam; gramicidin; haloprogin; hetacillin; hetacillin potassium; hexedine; ibafloxacin; imipenem; isoconazole; isepamicin; isoniazid; josamycin; kanamycin sulfate; kitasamycin; levofuraltadone; levopropylcillin potassium; lexithromycin; lincomycin; lincomycin hydrochloride; lomefloxacin; Lomefloxacin hydrochloride; lomefloxacin mesylate; loracarbef; mafenide; meclocycline; meclocycline sulfosalicylate; megalomicin potassium phosphate; mequidox; meropenem; methacycline; methacycline hydrochloride; methenamine;

methenamine hippurate; methenamine mandelate; methicillin sodium; metioprim; metronidazole hydrochloride; metronidazole phosphate; mezlocillin; mezlocillin sodium; minocycline; minocycline hydrochloride; mirincamycin hydrochloride; monensin; monensin sodiumr; nafcillin sodium; nalidixate sodium; nalidixic acid; natainycin; nebramycin; neomycin palmitate; neomycin sulfate; neomycin undecylenate; netilmicin sulfate; neutramycin; nifuiradene; nifuraldezone; nifuratel; nifuratrone; nifurdazil; nifurimide; nifiupirinol; nifurquinazol; nifurthiazole; nitrocycline; nitrofurantoin; nitromide; norfloxacin; novobiocin sodium; ofloxacin; onnetoprim; oxacillin; oxacillin sodium; oximonam; oximonam sodium; oxolinic acid; oxytetracycline; oxytetracycline calcium; oxytetracycline hydrochloride; paldimycin; parachlorophenol; paulomycin; pefloxacin; pefloxacin mesylate; penamecillin; penicillin G benzathine; penicillin G potassium; penicillin G procaine; penicillin G sodium; penicillin V; penicillin V benzathine; penicillin V hydrabamine; penicillin V potassium; pentizidone sodium; phenyl aminosalicylate; piperacillin sodium; pirbenicillin sodium; piridicillin sodium; pirlimycin hydrochloride; pivampicillin hydrochloride; pivampicillin pamoate; pivampicillin probenate; polymyxin B sulfate; porfiromycin; propikacin; pyrazinamide; pyrithione zinc; quindecamine acetate; quinupristin; racephenicol; ramoplanin; ranimycin; relomycin; repromicin; rifabutin; rifametane; rifamexil; rifamide; rifampin; rifapentine; rifaximin; rolitetracycline; rolitetracycline nitrate; rosaramicin; rosaramicin butyrate; rosaramicin propionate; rosaramicin sodium phosphate; rosaramicin stearate; rosoxacin; roxarsone; roxithromycin; sancycline; sanfetrinem sodium; sarmoxicillin; sarpicillin; scopafungin; sisomicin; sisomicin sulfate; sparfloxacin; spectinomycin hydrochloride; spiramycin; stallimycin hydrochloride; steffimycin; streptomycin sulfate; streptonicozid; sulfabenz; sulfabenzamide; sulfacetamide; sulfacetamide sodium; sulfacytine; sulfadiazine; sulfadiazine sodium; sulfadoxine; sulfalene; sulfamerazine; sulfameter; sulfamethazine; sulfamethizole; sulfamethoxazole; sulfamonomethoxine; sulfamoxole; sulfanilate zinc; sulfanitran; sulfasalazine; sulfasomizole; sulfathiazole; sulfazamet; sulfisoxazole; sulfisoxazole acetyl; sulfisboxazole diolamine; sulfomyxin; sulopenem; sultamricillin; suncillin sodium; talampicillin hydrochloride; teicoplanin; temafloxacin hydrochloride; temocillin; tetracycline; tetracycline hydrochloride; tetracycline phosphate complex; tetroxoprim; thiamphenicol; thiphencillin potassium; ticarcillin cresyl sodium; ticarcillin disodium; ticarcillin monosodium; ticlatone; tiodonium chloride; tobramycin; tobramycin sulfate; tosufloxacin; trimethoprim; trimethoprim sulfate; trisulfapyrimidines; troleandomycin; trospectomycin sulfate; tyrothricin; vancomycin; vancomycin hydrochloride; virginiamycin; or zorbamycin.

The methods and compounds as described herein are useful for both prophylactic and therapeutic treatment. As used herein the term treating or treatment includes prevention; delay in onset; diminution, eradication, or delay in exacerbation of signs or symptoms after onset; and prevention of relapse. For prophylactic use, a therapeutically effective amount of the compounds and compositions or pharmaceutically acceptable salts thereof as described herein are administered to a subject prior to onset (e.g., before obvious signs of a bacterial infection), during early onset (e.g., upon initial signs and symptoms of a bacterial infection), or after an established inflammatory response or development of a bacterial infection. Prophylactic administration can occur for several days to years prior to the manifestation of symptoms of an infection. Prophylactic administration can be used, for example, in the preventative treatment of subjects exposed to *Staphylococcus aureus*. Therapeutic treatment involves administering to a subject a therapeutically effective amount of the compounds and compositions or pharmaceutically acceptable salts thereof as described herein after a bacterial infection is diagnosed.

Kits

Also provided herein are kits for treating or preventing cancer in a subject. A kit can include any of the compounds or compositions described herein. A kit can further include one or more anti-cancer agents (e.g., paclitaxel). A kit can include an oral formulation of any of the compounds or compositions described herein. A kit can additionally include directions for use of the kit (e.g., instructions for treating a subject).

Also provided herein are kits for treating or preventing a bacterial infection in a subject. A kit can include any of the compounds or compositions described herein. A kit can further include one or more antibacterial agents (e.g., oxacillin). A kit can include an oral formulation of any of the compounds or compositions described herein. A kit can additionally include directions for use of the kit (e.g., instructions for treating a subject).

The examples below are intended to further illustrate certain aspects of the methods and compounds described herein, and are not intended to limit the scope of the claims.

EXAMPLES

The following examples are set forth below to illustrate the methods, compositions, and results according to the disclosed subject matter. These examples are not intended to be inclusive of all aspects of the subject matter disclosed herein, but rather to illustrate representative methods, compositions, and results. These examples are not intended to exclude equivalents and variations of the present invention, which are apparent to one skilled in the art.

Efforts have been made to ensure accuracy with respect to numbers (e.g., amounts, temperature, etc.) but some errors and deviations should be accounted for. Unless indicated otherwise, parts are parts by weight, temperature is in ° C. or is at ambient temperature, and pressure is at or near atmospheric. There are numerous variations and combinations of reaction conditions, e.g., component concentrations, temperatures, pressures, and other reaction ranges and conditions that can be used to optimize the product purity and yield obtained from the described process. Only reasonable and routine experimentation will be required to optimize such process conditions.

All chemicals were purchased from commercial suppliers and used without further purification. All solvents were dried and distilled before use. Tetrahydrofuran was distilled from sodium/benzophenone. Dichloromethane and acetonitrile were distilled over calcium hydride. Flash column chromatography was performed with silica gel (200-300 mesh). $^1$H NMR spectra were recorded at either 400 MHz or 600 MHz at ambient temperature. $^{13}$C NMR spectra were recorded at either 100 or 150 MHz at ambient temperature. Infrared spectra were recorded on a spectrophotometer (Perkin-Elmer Spectrum 100). Melting points were determined with melting point apparatus (Fukai X-4). High resolution mass spectra were performed by electrospray ionization (ESI) on an Agilent ESI-TOF LC-MS 6200 system. Analytical HPLC was performed on an Agilent 1100 series with

Example 1

Previous reports have discussed the ability of marinopyrrole A to inhibit the binding of Mcl-1 to Bim. However, marinopyrrole A only moderately inhibits the binding to Mcl-1 to Bim (8.9 µM), its selectivity for Mcl-1 over Bcl-xL is only two fold, and it suffers from poor solubility. Herein, new marinopyrrole A analogues were synthesized which can: have improved solubility and potency, identify chemical probes selective for Mcl-1, Bcl-xL or Bcl-2, and be developed as anti-cancer drugs. The molecular geometry of marinopyrrole A offers excellent opportunities to reach these goals by decorating this natural product based bispyrrole system with a large number of diverse functional groups. Marinopyrrole has at least eight sites amenable to optimization to accomplish the desired activity and selectivity.

Structure activity relationship studies using Mcl-1/Bim and Bcl-xL/Bim ELISA assays were used to identify marinopyrrole A analogues that are Mcl-1-selective and Bcl-xL-selective antagonists as well as dual inhibitors of Bim binding to both Mcl-1 and Bcl-xL. The parent marinopyrrole A [1=(±)–(1)] inhibits the binding of Mcl-1 to Bim with only moderate potency ($IC_{50}$=8.9 µM) (Table 1). The potency of 1 at inhibiting Bcl-xL/Bim binding had an $IC_{50}$ of 16.4 µM. All ELISA data reported herein were performed with both Mcl-1 and Bcl-xL at 10 nM.

Scheme 1. Marinoyrrole A and cyclic derivative (III) structures.

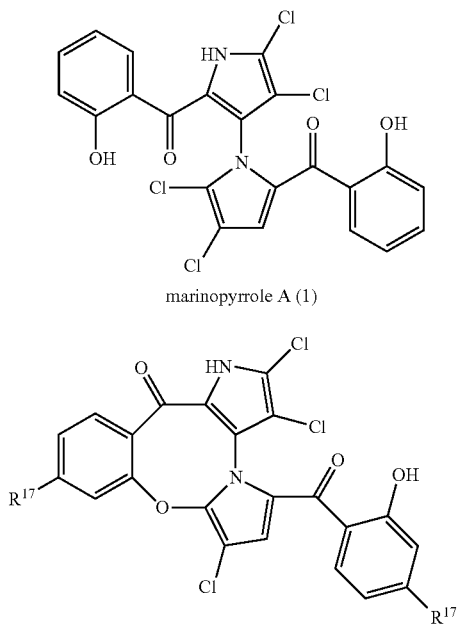

marinopyrrole A (1)

IV

TABLE 1

ELISA results of selected marinopyroles

| ID | $R^{17e}$ | Mcl-1-Bim[a] | Bcl-xL-Bim[a] |
|---|---|---|---|
| (±)-1 | — | 8.9 ± 1.0 | 16.4 ± 3.3 |
| (+)-1 | — | 12.7 ± 1.0 | 19.7 ± 3.6 |
| (−)-1 | — | 12.5 ± 1.4 | 12.0 ± 2.8 |
| IV-1 | $OSO_2CF_3$ | 1.4 ± 0.3 | 2.3 ± 1.1 |
| IV-2 | OH | 42.5 ± 6.0 | >100 |
| IV-3 | $CO_2CH_3$ | 4.3 ± 1.5 | 3.4 ± 0.9 |
| IV-4 | $CO_2H$ | 66.6 ± 2.6 | >100 |
| IV-5 | $PO(OCH_2CH_3)_2$ | >100 | >100 |
| IV-6 | $PO(OH)_2$ | >100 | >100 |

[a]$IC_{50}$ (average ± SEM) in µM, n ≥ 3.

Example 2

Marinopyrrole F (FIG. 1) was chosen as a starting point for optimization (Hughes C C et al. *J. Org. Chem.* 2010, 75, 3240-3250). Marinopyrrole F adopted specific conformations that locked one aromatic ring to the bispyrrole system due to the fused eight-membered ether linkage as shown by crystallographic X-ray analysis (Hughes C C et al. *J. Org. Chem.* 2010, 75, 3240-3250). Introduction of substituents in the para-position relative to the carbonyl group on both aromatic rings such as trifluoromethanesulfonate 3, methyl ester 4 or diethyl phosphonate 5 functionality generated a series of compounds that can have hydrogen bonding (acceptor) and hydrophobic interactions with the target. Furthermore, the unmasked hydroxyl 6, carboxylic acid 7 and phosphonic acid 8 groups in the corresponding positions can serve as both a hydrogen bond donor/acceptor and a functional group to improve aqueous solubility. To evaluate the potential differences in potency between the atropisomers of 1, both (+)-1 and (−)-1 marinopyrrole A were included in this study (Nicolaou K C et al. *Tetrahedron Lett.* 2011, 52, 2041-2043). The biological activity of brominated marinopyrrole A analog 9 was evaluated by ELISA assays (Nicolaou K C et al. *Tetrahedron Lett.* 2011, 52, 2041-2043).

Synthesis of Marinopyrrole Derivatives

Starting from compound 2 (Cheng C et al. *Mar. Drugs* 2013, 11, 2927-2948), macrocycle 3 was obtained in 80% yield after heating 2 in DMF at 110° C. (Scheme 2). Removal of the trifluoromethanesulfonic groups by saponification in methanolic THF gave phenol 6 in 81% yield. Palladium-mediated carbonylation (Uyanik M et al. *Org. Lett.* 2006, 8, 5649-5652) of 2 provided symmetrical marinopyrrole 4a and cyclic marinopyrrole 4 in 25% and 22% yield, respectively. Further heating of compound 4a at 80° C. generated 4, which can be due to spontaneous cyclization of 8-OH with 5'-Cl. Saponification of 4 and 4a yielded the corresponding carboxylic acid derivatives 7 and 7a, respectively (Scheme 3). Palladium-catalyzed phosphorylation (Petrakis K S and Nagabhushan T L. *J. Am. Chem. Soc.* 1987, 109, 2831-2833) of 2 with HPO(OEt)₂ furnished a mixture of symmetrical marinopyrrole 5a in 43% yield as well as cyclized 5 in 54% yield (Scheme 4). Intramolecular cyclization of 5a can also occur upon heating at 81-82° C. Finally, upon treatment with $Me_3SiBr$, 5 and 5a can be smoothly converted to the corresponding bisphosphonic acids 8 and 8a (Petrakis K S and Nagabhushan T L. *J. Am. Chem. Soc.* 1987, 109, 2831-2833).

Scheme 2. Synthesis of cyclic marinopyrroles 3 and 6.
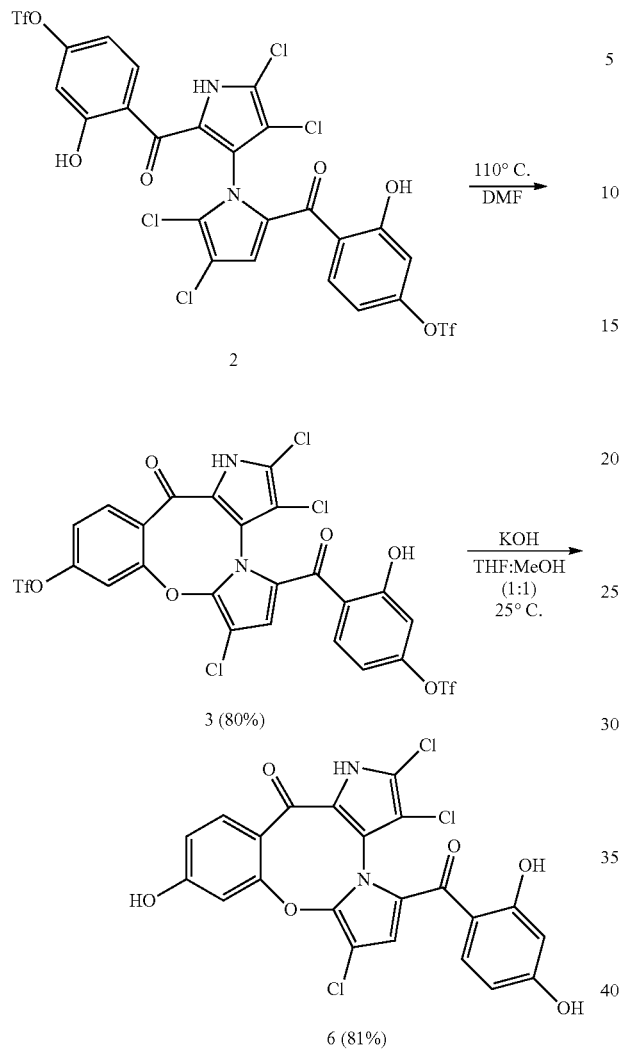
Scheme 3. Synthesis of cyclic and symmetrical marinopyrroles.
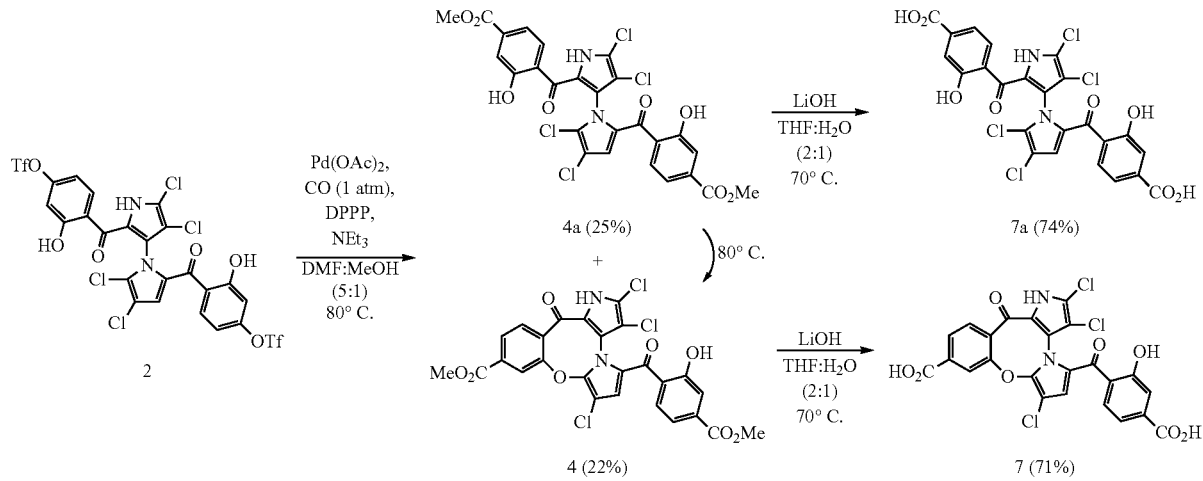

Scheme 4. Synthesis of cyclic and symmetrical marinopyrroles.

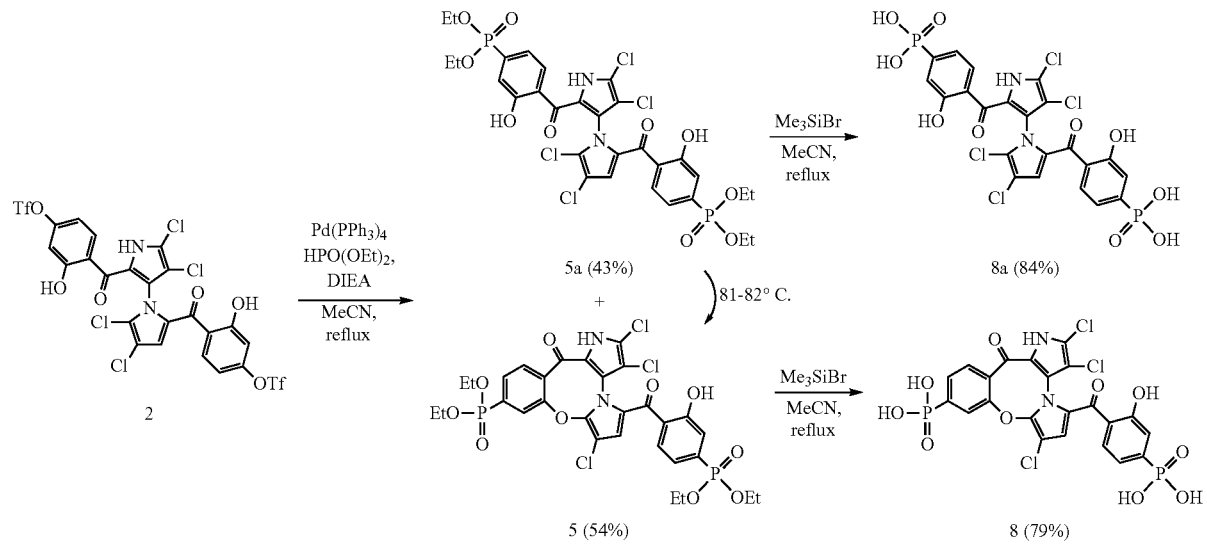

Physicochemical Properties and SAR of the Marinopyrroles

Figure 2:
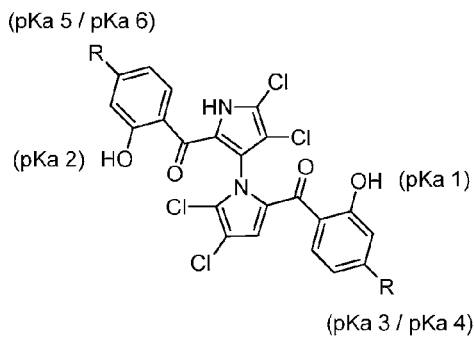
FIG. 2 shows the ELISA and physicochemical properties of 1 and symmetrical marinopyrroles.

Consistent with previous reports (Doi K et al. *J. Biol. Chem.* 2012, 287, 10224-10235), the $IC_{50}$ value of racemic marinopyrrole A to disrupt the binding of Mcl-1 to Bim was 8.9 µM. Although the activity of racemic marinopyrrole A against Bcl-$x_L$/Bim binding was lower than reported previously (Doi K et al. *J. Biol. Chem.* 2012, 287, 10224-10235), this reflects the lower Bcl-$x_L$ concentration (2.5 times lower) utilized in the present assay. No significant activity difference was observed between atropisomers (+)-1 and (−)-1, as both exhibited similar potencies against Mcl-1/Bim and Bcl-$x_L$/Bim (FIG. 2). Symmetrically para-substituted marinopyrroles with a carboxy methyl ester 4a and diethyl phosphonate 5a showed activity against Mcl-1/Bim but were inactive against Bcl-$x_L$/Bim ($IC_{50}$>100 µM). Furthermore, substitution in the para-position of the carbonyl group with carboxylic acid 7a showed lower activity than 1 against Mcl-1/Bim and little activity against Bcl-$x_L$/Bim. Bisphosphonic acid marinopyrrole 8a was slightly less potent than 1 against Mcl-1-Bim but not Bcl-$x_L$/Bim. The brominated marinopyrrole congener 9 (Nicolaou K C et al. *Tetrahedron Lett.* 2011, 52, 2041-2043) was two-fold more potent than 1 against both Mcl-1/Bim and Bcl-$x_L$/Bim.

Both $pK_a$ and log p values were calculated using ChemAxon Software Version 5.12.3 (Dixon S L and Jurs P C. *J. Comp. Chem.* 1993, 14, 1460-1467; Csizmadia F et al. *J. Pharm. Sci.* 1997, 86, 865-871). The $pK_a$ values of marinopyrrole A (1) were predicted to be 7.8 ($pK_a$ 1) and 8.4 ($pK_a$ 2), respectively (FIG. 2). As reported previously (Cheng C et al. *Mar. Drugs* 2013, 11, 2927-2948), the difference in $pK_a$ values for the hydroxyl group in ring A and ring B can be due to the axially chiral environment. The $pK_a$ values of 1 are 1.6-2.2 log units lower than that of phenol ($pK_a$=9.98) (Liptak M D et al. *J. Am. Chem. Soc.* 2002, 124, 6421-6427). An equilibrium can exist between open conformations and closed conformations in 1, similar to those observed in a report of intramolecular hydrogen bonding (Kuhn B et al. *J. Med. Chem.* 2010, 53, 2601-2611). The Fenical group reported the X-ray structure of marinopyrrole B (3'-Br analogue of 1) that indicated the preference for the formation of intramolecular hydrogen bonds between the peri-hydroxyl and the carbonyl group (Hughes C C et al. *Org. Lett.* 2008, 10, 629-631). These intramolecular hydrogen bond interactions can contribute not only to an increase of the compound's acidity but also an increase in its lipophilicity (Kuhn B et al. *J. Med. Chem.* 2010, 53, 2601-2611). The calculated log p value of 1 was 5.6, which marginally violates the Rule of Five (RO5), drug-like properties formulated by Lipinski (Lipinski C A et al. *Adv. Drug Del, Rev.* 2001, 46, 3-26). The calculated $pK_a$ 1 and $pK_a$ 2 values of marinopyrroles in FIG. 2 range from 6.8 to 8.4. Compound 7a has $pK_a$ 3 (3.8) and $pK_a$ 4 (3.2) values due to the carboxylic acid, while 8a has a $pK_a$ 3 (0.7-5.5) and $pK_a$ 4 (1.0-5.8) range of values corresponding to the phosphonic acid functional group. Clog p values of both compounds 7a (4.6) and 8a (2.4) reside within the suggested range for drug-like compounds. Despite the improvement in aqueous solubility of 7a and 8a over 1, both were found to be less active against Mcl-1/Bim and Bcl-$x_L$/Bim, which can be due to unfavorable ionic and/or hydrogen bond interactions with the targets.

Figure 3:
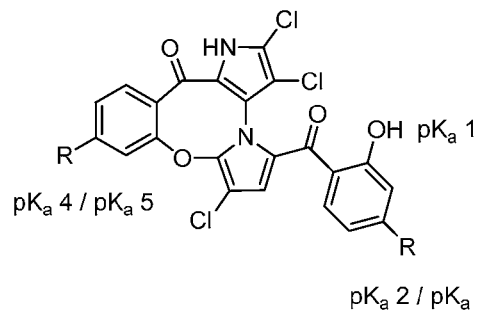
FIG. 3 shows the ELISA and physicochemical properties of cyclic marinopyrroles

Compared to the SARs of symmetrical marinopyrroles described (vide supra), cyclic marinopyrroles behaved similarly. Compounds containing functional groups with potential ionic and/or hydrogen bond interactions (6-8) reduced both anti Mcl-1/Bim and Bcl-$x_L$/Bim activity, as the cyclic marinopyrroles phosphonic acid 8 and ester 5 lack activity against both Mcl-1/Bim and Bcl-$x_L$/Bim ($IC_{50}$>100 µM in FIG. 3). Conversely, methyl ester 4 is two-fold more potent than 1 against Mcl-1/Bim and seven-fold more potent against Bcl-$x_L$/Bim. The trifluoromethanesulphonate 3 was the most potent cyclic marinopyrrole examined, showing six- and seven-fold higher potency than 1 against Mcl-1/Bim and Bcl-$x_L$/Bim, respectively. Compound 4 has a Clog p value of 4.7, while compound 3 has a Clog p value outside the advised range of RO5. The Clog p for compound 5 was marginally higher than the range of RO5, while the rest of compounds (6-8) have the Clog p values all within the recommended range for RO5. This series of cyclic marinopyrroles, which adopt constrained molecular geometries due to the locked ring system (Hughes C C et al. *J. Org.*

Chem. 2010, 75, 3240-3250), displayed enhanced ability to disrupt the binding of Bim to Mcl-1 and Bcl-$x_L$.

Activity in Intact Human Breast Cancer Cells

Figure 4:
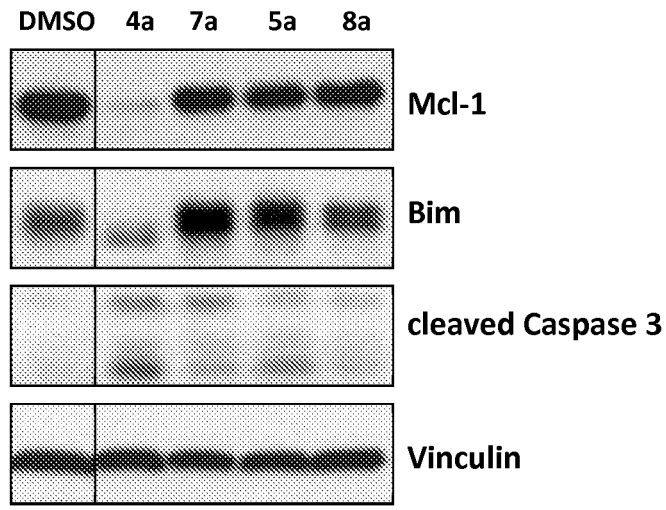
FIG. 4 shows the effect of marinopyrrole derivatives on Mcl-1, Bim and caspase 3 in human breast cancer cells.

To determine if the marinopyrroles were active in intact cells, human breast cancer MDA-MB-468 cells were treated with the marinopyrrole derivatives (10 μM for 16 h). The cells were then processed for western blotting according to a previously described methods (Balasis M E et al. *Clin. Cancer Res.* 2011, 17, 2852-2862). FIG. 4 shows that treatment of the cells with 4a resulted in a significant decrease in the levels of Mcl-1 and Bim, and cleavage of caspase 3. Compound 7a, the free carboxylic acid analogue of 4a, did not decrease Mcl-1 and Bim, and resulted in little caspase 3 cleavage. The phosphate 8a and its corresponding ethyl ester 5a had little effect on Mcl-1, Bim or caspase 3 (FIG. 4). The (±)-marinopyrrole A (1) (Doi K et al. *J. Biol. Chem.* 2012, 287, 10224-10235) and its atropisomers (+)-1 and (−)-1 as well as 9, tetrabromo-(±)-1, were able to decrease Mcl-1 and Bim and to cleave caspase 3. However, none of the cyclic marinopyrroles were active in intact cells.

Synthesis of Marinopyrrole Derivatives

3-Hydroxy-4-(2,3,7-trichloro-13-oxo-10-(((trifluoromethyl)sulfonyl)oxy)-1,13 dihydrobenzo[g]dipyrrolo[2,1-b:3',2'-d][1,3]oxazocine-5-carbonyl) phenyl trifluoromethanesulfonate (3)

Under $N_2$, (4,4',5,5'-tetrachloro-1'H-1,3'-bipyrrole-2,2'-diyl)bis(((2-hydroxy-4-hydroxytrifluoromethanesulfonate)-phenyl)methanone) (2) (Cheng C et al. *Mar. Drugs* 2013, 11, 2927-2948) (150 mg, 0.19 mmol) and NaI (120 mg, 0.75 mmol) were dissolved in DMF (5 mL). The mixture was heated to 110° C. and stirred for about 24 h. The reaction was quenched by addition of saturated aqueous $Na_2S_2O_3$ (20 mL) and extracted with EtOAc (15 mL×3). The suspension was filtered and the filtrate was concentrated in vacuum. The residue was purified by flash column chromatography (16% EtOAc/petroleum ether, $R_f$=0.2) to give 3 (115 mg, 80%) as a light yellow solid. mp 94.8-96.4° C.; $^1$H NMR (400 MHz, $CDCl_3$) δ 5.72 (s, 1H), 6.89 (dd, J=8.8, 2.0 Hz, 1H), 6.98 (d, J=2.4 Hz, 1H), 7.39 (dd, J=8.8, 2.0 Hz, 1H), 7.73 (d, J=2.4 Hz, 1H), 7.92 (d, J=8.8 Hz, 1H), 8.14 (d, J=8.8 Hz, 1H), 9.72 (br s, 1H), 11.55 (s, 1H) ppm; $^{13}$C NMR ($CDCl_3$, 100 MHz) δ 101.68, 106.22, 111.40, 112.60, 116.88, 117.00, 119.02, 120.19, 120.98, 121.12, 121.28, 122.85, 124.18, 125.33, 129.73, 134.45, 135.18, 144.90, 152.81, 154.62, 157.16, 164.28, 174.98, 186.66 ppm; HRMS (M+H$^+$) calcd for $C_{24}H_{10}Cl_3F_6N_2O_{10}S_2$ 768.8747. found 768.8809; IR (KBr) 3423, 3244, 2960, 2922, 2852, 1626, 1604, 1580, 1462, 1426, 1217, 1139, 1095, 965, 790 cm$^{-1}$. HPLC purity, 99.1% (Flow rate: 1 mL/min; Column: Agilent ZORBAX 300SB-C8, 5 μm, 150×4.6 mm; Wavelength: UV 254 nm; Temperature: 25° C.; Mobile phase: MeOH:$H_2O$=80:20; $t_R$=28.9 min).

2,3,7-Trichloro-5-(2,4-dihydroxybenzoyl)-10-hydroxybenzo[g]dipyrrolo[2,1-b:3',2'-d][1,3]oxazo-cin-13(1H)-one (6)

To a solution of 3 (65 mg, 0.08 mmol) in a mixture of MeOH/THF (1:1, 4 mL), KOH (47 mg, 0.80 mmol) was added at room temperature. The mixture was heated to 70° C. and stirred for 10 h. The reaction mixture was adjusted to pH 7.0 with 0.5 N HCl and extracted with EtOAc (10 mL×3). The combined organic layers were dried over anhydrous sodium sulfate, filtered and concentrated in vacuum.

The residue was purified by flash column chromatography (33% EtOAc/petroleum ether, $R_f$=0.3) to yield 6 (34 mg, 81%) as a yellow solid. mp 274.7-276.0° C.; $^1$H NMR (400 MHz, acetone-d$_6$) δ 6.37 (s, 1H), 6.84 (d, J=2.0 Hz, 1H), 6.95 (br s, 1H), 7.44 (dd, J=8.8, 2.4 Hz, 1H), 7.72 (d, J=2.0 Hz, 1H), 8.17 (dd, J=8.4, 3.2 Hz, 1H), 8.38 (d, J=8.4 Hz, 1H) ppm; $^{13}$C NMR ($CD_3OD$, 100 MHz) δ 91.20, 94.31, 96.54, 100.56, 100.90, 105.20, 106.97, 109.25, 113.22, 113.86, 115.03, 115.39, 115.68, 125.60, 125.62, 127.17, 150.97, 156.11, 157.43, 158.23, 168.02 178.12 ppm; HRMS (M+K$^+$) calcd for $C_{22}H_{11}Cl_3KN_2O_6$ 542.9320. found 542.9297; IR (KBr) 3415, 3251, 2962, 2924, 1619, 1581, 1547, 1476, 1456, 1310, 1090, 796 cm$^{-1}$. HPLC purity, 98.9% (Flow rate: 1 mL/min; Column: Agilent ZORBAX 300SB-C8, 5 μm, 150×4.6 mm; Wavelength: UV 254 nm; Temperature: 25° C.; Mobile phase: MeOH:$H_2O$=75:25; $t_R$=7.5 min).

Methyl-2,3,7-trichloro-5-(2-hydroxy-4-(methoxycarbonyl)benzol)-13-oxo-1,13-dihydrobenzo[g]-dipyrrolo[2,1-b:3',2'-d][1,3]oxazocine-10-carboxylate (4) and Dimethyl-4,4'-(4,4',5,5'-tetrachloro-1'H-[1,3'-bipyrrole]-2,2'-dicarbonyl)bis(3-hydroxybenzoate) (4a)

Under CO (1 atm), 2 (400 mg, 0.50 mmol), DPPP (26 mg, 0.10 mmol), Pd(OAc)$_2$ (11 mg, 0.05 mmol) and Et$_3$N (251 mg, 2.50 mmol) were dissolved in a mixture of DMF/MeOH (5:1, 5 mL). The reaction was heated to 80° C. and stirred for 3 h. The reaction mixture was quenched with water (10 mL) and extracted with EtOAc (15 mL×3). The combined organic layers were dried over anhydrous sodium sulfate, filtered and concentrated in vacuum. The residue was purified by flash column chromatography (50% EtOAc/petroleum ether, $R_f$=0.2) to give 4 (70 mg, 22%) and 4a (80 mg, 25%) as a pale yellow solid.

4: mp 135.7-137.0° C.; $^1$H NMR (400 MHz, $CDCl_3$) δ 3.96 (s, 3H), 3.98 (s, 3H), 5.72 (s, 1H), 7.56 (d, J=8.0 Hz, 1H), 7.69 (s, 1H), 7.84 (d, J=6.8 Hz, 1H), 8.07 (s, 2H), 8.40 (s, 1H), 9.88 (s, 1H), 11.22 (s, 1H) ppm; $^{13}$C NMR (acetone-d$_6$, 100 MHz) δ 52.81, 53.16, 107.56, 118.58, 118.60, 120.76, 124.61, 128.87, 132.99, 132.99, 133.71, 134.02, 134.26, 136.82, 136.99, 149.00, 157.40, 157.51, 164.91, 165.33, 166.12, 167.90, 174.87, 176.18, 178.01, 183.00 ppm; HRMS (M+H$^+$) calcd for $C_{26}H_{16}Cl_3N_2O_8$ 588.9972. found 588.9967; IR (KBr) 3416, 3236, 2954, 2852, 1730, 1609, 1580, 1461, 1414, 1288, 1207, 1090, 988, 806 cm$^{-1}$. HPLC purity, 95.6% (Flow rate: 1 mL/min; Column: Waters C18, 5 m, 150×4.6 mm; Wavelength: UV 254 nm; Temperature: 25° C.; Mobile phase: MeOH:$H_2O$=90:10; $t_R$=4.6 min).

4a: mp 99.4-101.0° C.; $^1$H NMR (400 MHz, acetone-d$_6$) δ 3.84 (s, 3H), 3.86 (s, 3H), 6.18 (s, 1H), 7.27 (dd, J=8.4, 1.6 Hz, 1H), 7.42-7.44 (m, 3H), 7.87 (d, J=8.4 Hz, 1H), 8.04 (d, J=8.0 Hz, 1H) ppm; $^{13}$C NMR (acetone-d$_6$, 100 MHz) δ 52.68, 52.75, 110.16, 118.28, 118.51, 119.94, 120.60, 122.61, 123.20, 124.43, 126.43, 126.59, 127.10, 128.72, 130.72, 133.06, 135.43, 136.51, 158.90, 159.95, 166.17, 166.17, 184.78, 185.08, 185.60, 186.13 ppm; HRMS (M+H$^+$) calcd for $C_{26}H_{17}Cl_4N_2O_8$ 624.9739. found 624.9736; IR (KBr) 3245, 2954, 1727, 1632, 1599, 1441, 1291, 1223, 1093, 884, 759, 672 cm$^{-1}$. HPLC purity, 96.3% (Flow rate: 1 mL/min; Column: Agilent ZORBAX 300SB-C8, 5 μm, 150×4.6 mm; Wavelength: UV 254 nm; Temperature: 25° C.; Mobile phase: MeOH:$H_2O$=80:20; $t_R$=6.6 min).

5-(4-Carboxy-2-hydroxybenzoyl)-2,3,7-trichloro-13-oxo-1,13-dihydrobenzo[g]dipyrrolo[2,1-b:3',2'-d][1,3]oxazocine-10-carboxylic acid (7)

To a solution of 4 (44 mg, 0.07 mmol) in a mixture of $H_2O$/THF (1:2, 5 mL), LiOH (27 mg, 1.1 mmol) was added at room temperature. The reaction was heated to 70° C. and stirred for 10 h. The reaction mixture was adjusted to pH 5.0 with 0.5 N HCl and extracted with EtOAc (10 mL×3). The combined organic layers were dried over anhydrous sodium sulfate, filtered and concentrated in vacuum. The residue was purified by reverse-phase flash column chromatography (6% AcOH, 23% $H_2O$, 71% MeOH, $R_f$=0.2) to give 7 (30 mg, 71%) as a light yellow solid. mp 215.5-217.0° C.; $^1$H NMR (400 MHz, DMSO-$d_6$) δ 6.03 (s, 1H), 7.40 (m, 3H), 8.03 (m, 2H), 8.14 (s, 1H) ppm; $^{13}$C NMR (DMSO-$d_6$, 100 MHz) δ 100.08, 107.72, 117.52, 120.03, 120.62, 123.74, 124.50, 124.73, 125.18, 128.83, 130.17, 130.78, 132.98, 133.43, 136.00, 139.29, 145.72, 156.81, 156.81, 166.57, 167.44, 173.04, 175.98, 183.02 ppm; HRMS (M+H$^+$) calcd for $C_{24}H_{12}Cl_3N_2O_8$ 560.9659. found 560.9669; IR (KBr) 3420, 3240, 3127, 2925, 2600, 1710, 1604, 1580, 1462, 1413, 1311, 1210, 1025, 996, 906, 799, 761 cm$^{-1}$. HPLC purity, 99.3% (Flow rate: 1 mL/min; Column: Waters C18, 5 m, 150×4.6 mm; Wavelength: UV 254 nm; Temperature: 25° C.; Mobile phase: MeOH:$H_2O$=55:45; $t_R$=6.7 min).

4,4'-(4,4',5,5'-Tetrachloro-1'H-[1,3'-bipyrrole]-2,2'-dicarbonyl)bis(3-hydroxybenzoic acid) (7a)

To a solution of 4a (27 mg, 0.04 mmol) in a mixture of $H_2O$/THF (1:2, 3 mL), LiOH (16 mg, 0.65 mmol) was added at room temperature. The reaction was heated to 70° C. and stirred for 10 h. The reaction mixture was adjusted to pH 5.0 with 0.5 N HCl and extracted with EtOAc (10 mL×3). The combined organic layers were dried over anhydrous sodium sulfate, filtered and concentrated in vacuum. The residue was purified by reverse-phase flash column chromatography (6% AcOH, 30% $H_2O$, 64% MeOH, $R_f$=0.2) to give 7a (19 mg, 74%) as a light yellow solid. mp 190.5-192.0° C.; $^1$H NMR (400 MHz, DMSO-$d_6$) δ 6.10 (s, 1H), 7.19 (d, J=8.0 Hz, 2H), 7.29-7.33 (m, 4H) ppm; $^{13}$C NMR (DMSO-$d_6$, 100 MHz) δ 109.69, 110.24, 116.80, 117.21, 118.60, 118.66, 120.03, 122.32, 122.57, 124.96, 129.10, 129.26, 129.80, 129.90, 129.92, 134.57, 135.43, 156.09, 156.47, 167.58, 167.58, 172.66, 181.88, 183.14 ppm; HRMS (M+Na$^+$) calcd for $C_{24}H_{12}Cl_4N_2NaO_8$ 618.9245. found 618.9258; IR (KBr) 3075, 2956, 2919, 2851, 1707, 1631, 1599, 1446, 1394, 1294, 1228, 1023, 995, 885, 760 cm$^{-1}$. HPLC purity, 98.6% (Flow rate: 1 mL/min; Column: Waters C18, 5 m, 150×4.6 mm; Wavelength: UV 254 nm; Temperature: 25 OC; Mobile phase: MeOH:$H_2O$=65:35; $t_R$=5.1 min).

3-Hydroxy-4-(2,3,7-trichloro-13-oxo-10-(diethylphosphonyl)-1,13-dihydrobenzo[g]dipyrrolo[2,1-b:3',2'-d][1,3]oxazocine-5-carbonyl)diethyl phosphonate (5) and tetraethyl((4,4',5,5'-tetrachloro-1'H-[1,3'-bipyrrole]-2,2'-dicarbonyl)bis(3-hydroxy-4,1-phenylene))bis(phosphonate) (5a)

Under $N_2$, 2 (50 mg, 0.06 mmol), diethyl phosphonate (52 mg, 0.36 mmol), Pd(PPh$_3$)$_4$ (7.6 mg, 0.006 mmol) and i-Pr$_2$NEt (48 mg, 0.36 mmol) were dissolved in anhydrous MeCN (5 mL). The reaction was heated to reflux and stirred for 10 h. The reaction mixture was quenched with water (10 mL) and extracted with EtOAc (15 mL×3). The combined organic layers were dried over anhydrous sodium sulfate, filtered and concentrated in vacuum. The residue was purified by flash column chromatography (50% EtOAc/petroleum ether, $R_f$=0.2) to give 5 (25 mg, 54%) and 5a (20 mg, 43%) as a yellow solid. 5: mp 122.8-124.3° C.; $^1$H NMR (400 MHz, CDCl$_3$) δ 1.36 (t, J=6.8 Hz, 12H), 4.12-4.24 (m, 8H), 5.71 (s, 1H), 7.36 (t, J=8.4 Hz, 1H), 7.47 (d, J=15.2 Hz, 1H), 7.87 (m, 2H), 8.08 (dd, J=7.6, 5.2 Hz, 1H), 8.17 (d, J=13.6 Hz, 1H), 9.85 (br s, 1H), 11.27 (s, 1H) ppm; $^{13}$C NMR (CDCl$_3$, 100 MHz) δ 16.02, 16.02, 16.27, 16.27, 62.64, 62.70, 62.83, 62.83, 101.22, 106.12, 121.00, 121.59, 121.74, 123.06, 124.32, 125.10, 126.46, 130.33, 132.61, 132.77, 132.89, 135.07, 135.93, 136.94, 137.75, 145.48, 156.50, 161.50, 175.82, 187.12 ppm; HRMS (M+H$^+$) calcd for $C_{30}H_{30}Cl_3N_2O_{10}P_2$ 745.0441. found 745.0454; IR (KBr) 3421, 3338, 3123, 3078, 2983, 2925, 2855, 1614, 1579, 1461, 1258, 1232, 1050, 1021, 796 cm$^{-1}$. HPLC purity, 97.2% (Flow rate: 1 mL/min; Column: Agilent ZORBAX 300SB-C8, 5 m, 150×4.6 mm; Wavelength: UV 254 nm; Temperature: 25° C.; Mobile phase: MeOH:$H_2O$=80:20; $t_R$=6.8 min).

5a: mp 100.7-101.5° C.; $^1$H NMR (400 MHz, CDCl$_3$) δ 1.24-1.36 (m, 12H), 3.98-4.22 (m, 8H), 6.15 (s, 1H), 6.91 (dd, J=11.6, 8.0 Hz, 1H), 7.24-7.27 (m, 1H), 7.30 (d, J=14.4 Hz, 1H), 7.40 (d, J=14.8 Hz, 1H), 7.52 (t, J=14.4 Hz, 1H), 7.56 (dd, J=7.6, 2.8 Hz, 1H), 8.00 (br s, 1H), 11.12 (s, 1H), 11.44 (br s, 1H) ppm; $^{13}$C NMR (CDCl$_3$, 100 MHz) δ 16.22, 16.22, 16.28, 16.28, 62.69, 62.69, 62.74, 62.74, 108.90, 111.95, 117.68, 120.73, 121.03, 121.38, 121.47, 121.59, 122.07, 122.65, 122.84, 124.79, 130.95, 133.35, 135.84, 137.67, 160.29, 160.48, 161.32, 161.52, 185.51, 187.50 ppm; HRMS (M+H$^+$) calcd for $C_{30}H_{31}Cl_4N_2O_{10}P_2$ 781.0208. found 781.0220; IR (KBr) 3416, 3214, 2964, 2926, 2867, 1631, 1449, 1406, 1259, 1222, 1022, 938, 800, 671 cm$^{-1}$. HPLC purity, 97.0% (Flow rate, 1 mL/min; Column: Phenomenex C6-phenyl, 5 m, 150×4.6 mm; Wavelength: UV 254 nm; Temperature: 25° C.; Mobile phase: MeOH:$H_2O$=80:20; $t_R$=4.0 min).

3-Hydroxy-4-(2,3,7-trichloro-13-oxo-10-phosphoryl-1,13-dihydrobenzo[g]dipyrrolo[2,1-b:3',2'-d][1,3]oxazocine-5-carbonyl) phosphonic acid (8)

To a solution of 5 (40 mg, 0.054 mmol) in MeCN (3 mL), Me$_3$SiBr (230 mg, 1.50 mmol) was added via a syringe at room temperature under $N_2$. The reaction was heated to reflux and stirred for 24 h. The reaction mixture was concentrated in vacuum. The residue was purified by reverse-phase flash column chromatography (6% AcOH, 47% $H_2O$, 47% MeOH, $R_f$=0.2) to give 8 (27 mg, 79%) as a yellow solid. mp 314.7-316.0° C.; $^1$H NMR (400 MHz, CD$_3$OD) δ 5.95 (s, 1H), 7.26 (dd, J=12.8, 8.4 Hz, 1H), 7.32 (d, J=14.8 Hz, 1H), 7.53 (dd, J=8.0, 4.4 Hz, 1H), 7.85 (dd, J=12.8, 8.0 Hz, 1H), 8.08 (dd, J=8.0, 4.4 Hz, 1H), 8.15 (d, J=13.6 Hz, 1H) ppm; $^{13}$C NMR (CD$_3$OD, 100 MHz) δ 101.57, 101.69, 106.80, 107.56, 120.56, 121.47, 122.50, 124.67, 125.16, 125.52, 125.87, 126.60, 127.10, 130.67, 132.50, 133.46, 136.20, 141.71, 147.04, 162.26, 177.27, 186.48 ppm; HRMS (M+H$^+$) calcd for $C_{22}H_{14}Cl_3N_2O_{10}P_2$ 632.9189. found 632.9193; IR (KBr) 3790, 3407, 2955, 2920, 2850, 1727, 1596, 1458, 1401, 877 cm$^{-1}$. HPLC purity, 99.7% (Flow rate: 1 mL/min; Column: Agilent ZORBAX 300SB-C8, 5 μm, 150×4.6 mm; Wavelength: UV 254 nm; Temperature: 25° C.; Mobile phase: MeOH:$H_2O$=55:45; $t_R$=4.1 min).

((4,4',5,5'-Tetrachloro-1'H-[1,3'-bipyrrole]-2,2'-dicarbonyl)bis(3-hydroxy-4,1-phenylene))diphosphonic acid (8a)

To a solution of 5a (18 mg, 0.023 mmol) in MeCN (3 mL), Me$_3$SiBr (99 mg, 0.65 mmol) was added via a syringe at room temperature under N$_2$. The reaction was heated to reflux and stirred for 24 h. The reaction mixture was concentrated in vacuum. The residue was purified by reverse-phase flash column chromatography (6% AcOH, 30% H$_2$O, 64% MeOH, R$_f$=0.2) to give 8a (13 mg, 84%) as a yellow solid. mp 317.6-318.7° C.; $^1$H NMR (400 MHz, CD$_3$OD) δ 6.29 (s, 1H), 7.05 (s, 1H), 7.26-7.37 (m, 5H) ppm; $^{13}$C NMR (CD$_3$OD, 100 MHz) δ 110.32, 110.38, 112.63, 114.07, 118.96, 120.50, 121.60, 122.41, 123.23, 123.83, 125.59, 125.94, 126.34, 127.43, 129.35, 130.79, 132.80, 136.61, 159.27, 159.82, 185.99, 187.14 ppm; HRMS (M+H$^+$) calcd for C$_{22}$H$_{15}$Cl$_4$N$_2$O$_{10}$P$_2$ 668.8956. found 668.8958; IR (KBr) 2955, 2919, 2850, 1626, 1464, 1020, 799 cm$^{-1}$. HPLC purity, 99.5% (Flow rate: 1 mL/min; Column: Agilent ZORBAX 300SB-C8, 5 μm, 150×4.6 mm; Wavelength: UV 254 nm; Temperature: 25° C.; Mobile phase: MeOH:H$_2$O=55:45; t$_R$=4.0 min).

Enzyme-Linked Immunosorbent Assay (ELISA) and Western Blotting Following Treatment of Intact Human Breast Cancer Cells ELISAs were performed using a modified version of a previously described procedure (Doi K et al. *J. Biol. Chem.* 2012, 287, 10224-10235). Briefly, 40 nM of biotinylated Bim BH3 peptide (Biomatik) in SuperBlock blocking buffer (Pierce) was incubated in high-binding capacity streptavidin-coated plates (Pierce) for 2 h. Compounds were diluted in 120 μl of PBS containing 10 nM of GST-Mcl-1 or GST-Bcl-x$_L$ in 1.5 mL tubes for 15 min. Wells were washed with wash buffer (PBS containing 0.05% Tween-20) and then 100 μL of the compound/GST-protein mixture was transferred to the wells. The plates were incubated for 2 h, and then the wells were washed with wash buffer. HRP-conjugated anti-GST antibody (Bethyl Laboratories) was diluted 1:2000 in SuperBlock and 100 μL was transferred to each well. The plate was incubated for 1 h, and then the wells were washed with wash buffer followed by PBS. 100 μL of SureBlue TMB Microwell Peroxidase Substrate (VWR) was added to each well and plates were developed for 5-10 min. 100 μL of 1 N HCl was added to each well to stop the reaction and absorbance was read at 450 nm using a Quant plate reader (Bio-Tek). Treatment of the human breast cancer (MDA-MB-468) cells and western blotting were performed using a previously described method (Balasis M E et al. *Clin. Cancer Res.* 2011, 17, 2852-2862).

Described herein are general synthetic routes to access cyclic marinopyrrole derivatives and evaluation of their in vitro activity against binding of the pro-survival proteins Mcl-1 and Bcl-x$_L$ to the pro-apoptotic protein Bim. The efforts were focused on improving anti Mcl-1/Bim and Bcl-x$_L$/Bim potency. SAR studies of marinopyrrole derivatives demonstrated: i) replacing the chlorines with bromines within the bispyrrole core improved the potency by two fold (1 vs. 9); ii) symmetrical marinopyrroles with substituents in the para-position to the carbonyl group are more potent against Mcl-1/Bim than Bcl-x$_L$/Bim (FIG. 2); iii) the same trend was observed for cyclic marinopyrroles (FIG. 3); iv) cyclic marinopyrrole 3 is six- and seven-fold more potent than 1 against Mcl-1/Bim and Bcl-x$_L$/Bim, respectively (FIG. 3); v) the cyclic marinopyrroles with certain substituents (OSO$_2$SF$_3$ and CO$_2$Me) in the para-position to the carbonyl group are excellent "leads" for further optimization. The disclosed cyclic marinopyrroles have improved potency against both Mcl-1 and Bcl-x$_L$.

Example 3

A series of marinopyrrole derivatives were designed and synthesized. Their activity to disrupt the binding of the pro-apoptotic protein Bim to the pro-survival proteins Mcl-1 and Bcl-x$_L$ was evaluated using ELISA assays. Structural characterization of marinopyrroles binding to Mcl-1 was performed using NMR chemical shift perturbations assisted with molecular modeling. Analogues where the 4- and 4'-hydrogens of phenyl rings A and B in the synthetic marinopyrrole A (±)-1, a racemic form of the parent natural product marinopyrrole A (−)-1, were replaced by sulfide- or bistriazole-containing moieties such as 1-10 and 1-23 were the most potent [500 nM; up to 32-fold more potent than (±)-1]. The most potent dual Mcl-1 and Bcl-x$_L$ antagonists were sulfide 1-10 and triazole 1-21. Furthermore, bistriazole 1-21 display chemical shift perturbations on G219, G230 and G271 of Mcl-1 suggesting that it binds in to the BH3 binding domain of Mcl-1. Several Marinopyrrole derivatives inhibit human breast cancer cell survival potently suggesting that these compounds exhibit anticancer activity.

Design of Disruptors of Mcl-1/Bim and BclxL/Bim Protein-Protein Interactions

The molecular geometry of marinopyrrole A (1) offers excellent opportunities to decorate this natural product-based bispyrrole system for desired activity and selectivity. Previous reports (Doi K, et al. *J Biol. Chem.* 2012, 287, 10224-10235) have shown, via docking studies based on NMR chemical shift perturbations, that marinopyrrole A binds to Mcl-1 in two major regions. One is centered at the Mcl-1 p2 pocket between helices 4 and 5 and in contact with helix 3. The other is centered at the p4 pocket between helices 5 and 8 and in contact with helix 2. In order to have comprehensive understanding of SARs, potential sites of marinopyrrole A amenable for optimization were identified (Table 2). A series of marinopyrrole derivatives with substitution at the para-position of two phenyl rings to the carbonyl groups was focused on. Di-substitutions with hydrophobic groups on both phenyl rings furnished compounds 1-1 to 1-6, while those with hydrophilic groups yielded derivatives 1-7, 1-8, 1-15 and 1-16. Tri-substitutions of "symmetrical" marinopyrroles on both phenyl rings provided compounds 1-2, 1-8, and 1-17 to 1-19. Design of "non-symmetrical" marinopyrroles included compounds 1-27 to 1-33, 1-36 and 1-37. Extension of functional groups in the para-position of the phenyl rings with sulfide or sulphone spacer furnished compounds 1-9 to 1-16. Marinopyrroles with bistriazole spacer, compounds 1-17 to 1-26, were designed to assess the binding along the entire α-helix from p1 to p4 pockets. N-methyl analogues 1-34 and 1-35 were designed to further assess the role of the free NH group. "Symmetrical" and "non-symmetrical" marinopyrroles have been further discussed in PCT/US2014/012442 and WO 2013/158197, respectively, which are incorporated herein by reference.

Chemistry and Synthesis

Starting from previously reported compound 2 (Cheng C, et al. *Mar. Drugs.* 2013, 11, 2927-2948), mono-ketone 4 was obtained in 73% yield over two steps by introduction of ortho-methoxy-para-methylphenyl group (3 was not isolated) followed by IBX oxidation (Scheme 5). Removal of the TBDMS protecting group with TBAF gave alcohol 5 in 90% yield. Oxidation of 5 by IBX furnished aldehyde 6 in 90% yield. Bisketone 8 was obtained in 54% yield after introduction of a second ortho-methoxy-para-methylphenyl group (without isolation of 7) followed by IBX oxidation. Removal of the para-toluenesulfonyl group with KOH generated 9 in 98% yield, which was converted to 10 in 65% yield by chlorination with NCS (Cheng C, et al. *Mar. Drugs*. 2013, 11, 2927-2948). The symmetrical marinopyrrole derivative 1-2 was obtained in 85% yield after demethylation using BBr$_3$/DCM (Cheng C, et al. *J. Comb. Chem*. 2010, 12, 541-547).

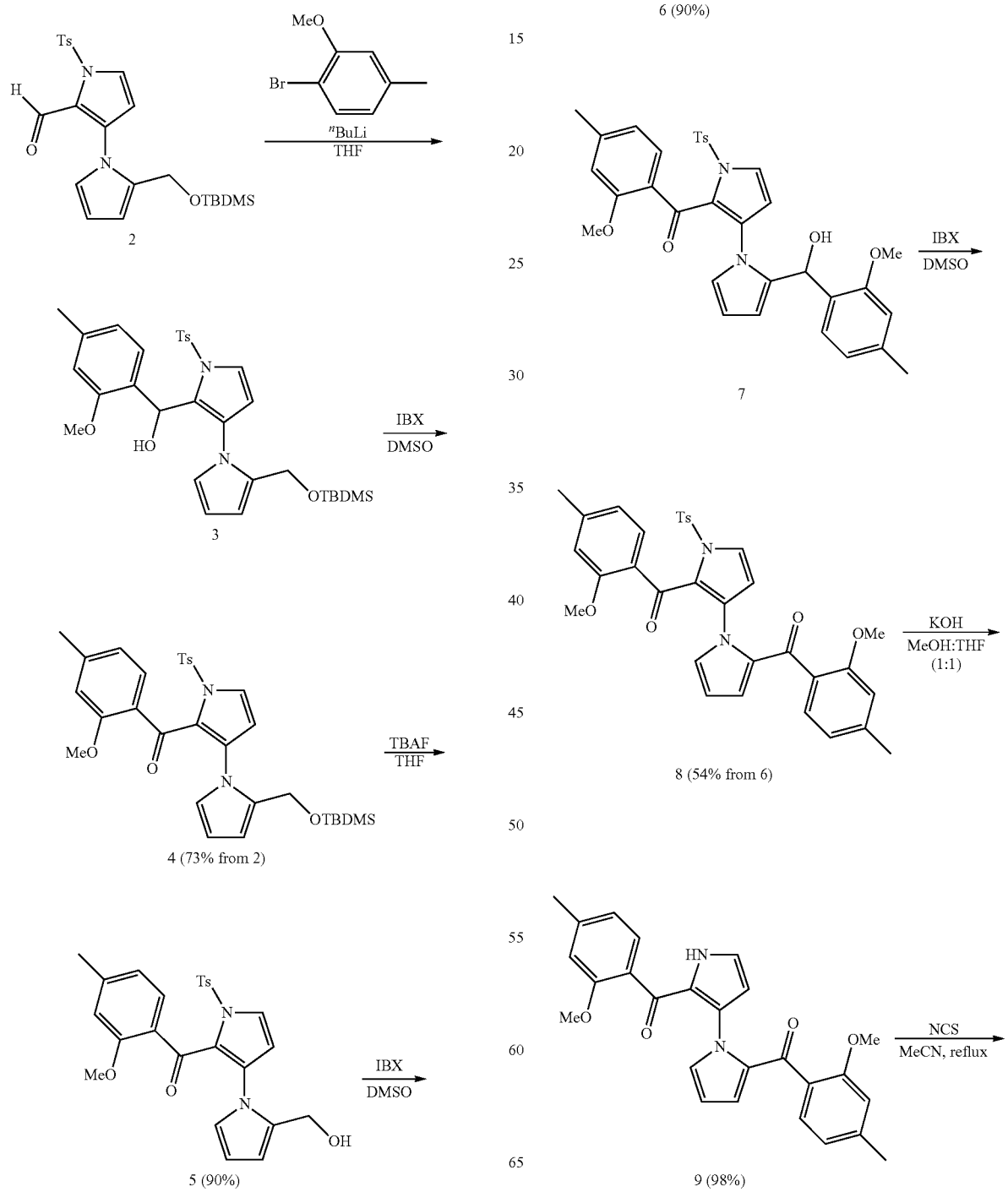

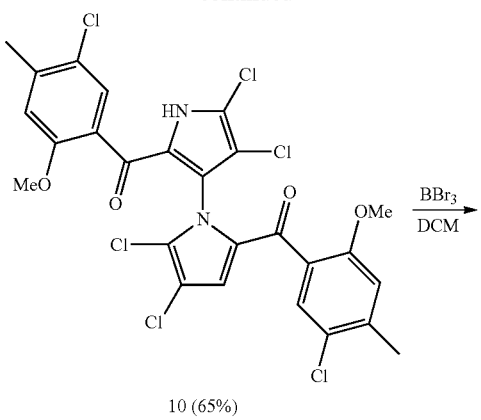

10 (65%)

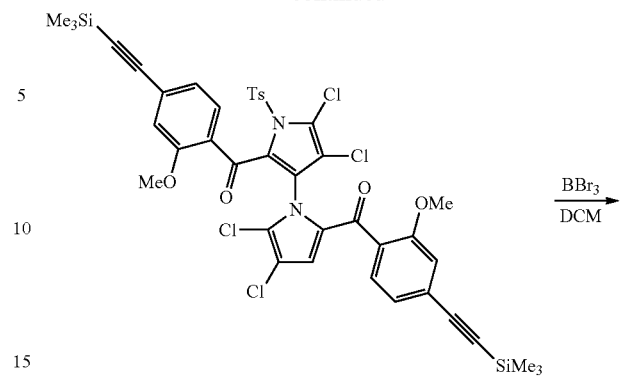

12 (74%)

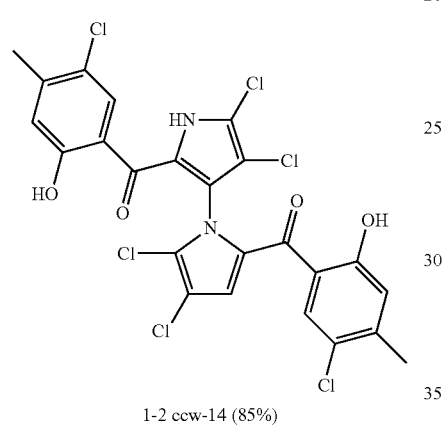

1-2 ccw-14 (85%)

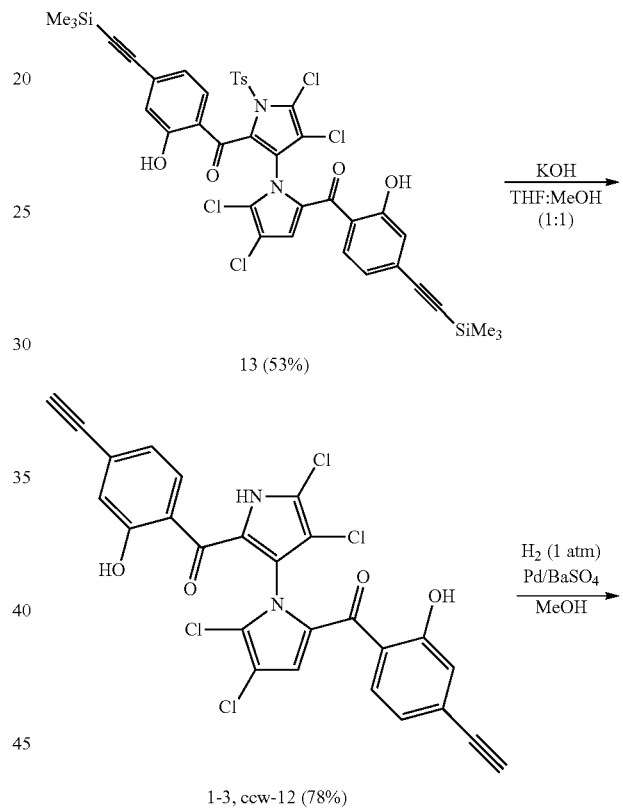

13 (53%)

1-3, ccw-12 (78%)

1-4, ccw-13 (60%)

Using previously reported intermediate 11 (Cheng C, et al. Mar. Drugs. 2013, 11, 2927-2948) as a starting material, palladium-mediated substitution of the triflate 11 with ethynyltrimethylsilane furnished 12 in 74% yield (Scheme 6). Demethylation of 12 using BBr$_3$/DCM gave 13 in 53% yield, which was converted to the symmetrical marinopyrrole 1-3 in 78% yield. Reduction of triple bonds in 1-3 with atmospheric H$_2$/Pd/BaSO$_4$ provided para-vinyl substituted marinopyrrole 1-4 in 60% yield, which was further reduced with atmospheric H$_2$/Pd/BaSO$_4$ to para-ethyl marinopyrrole 1-5 in 96% yield.

Scheme 6. Synthesis of marinopyrroles 1-3-1-5.

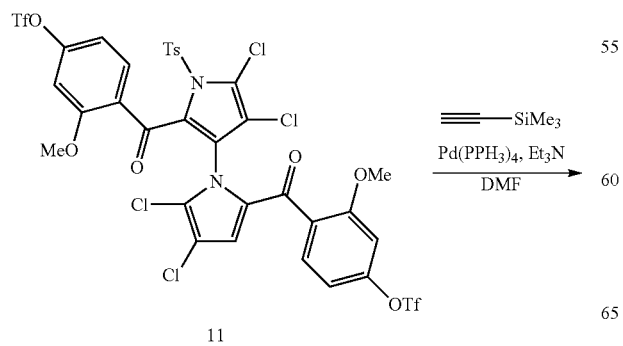

11

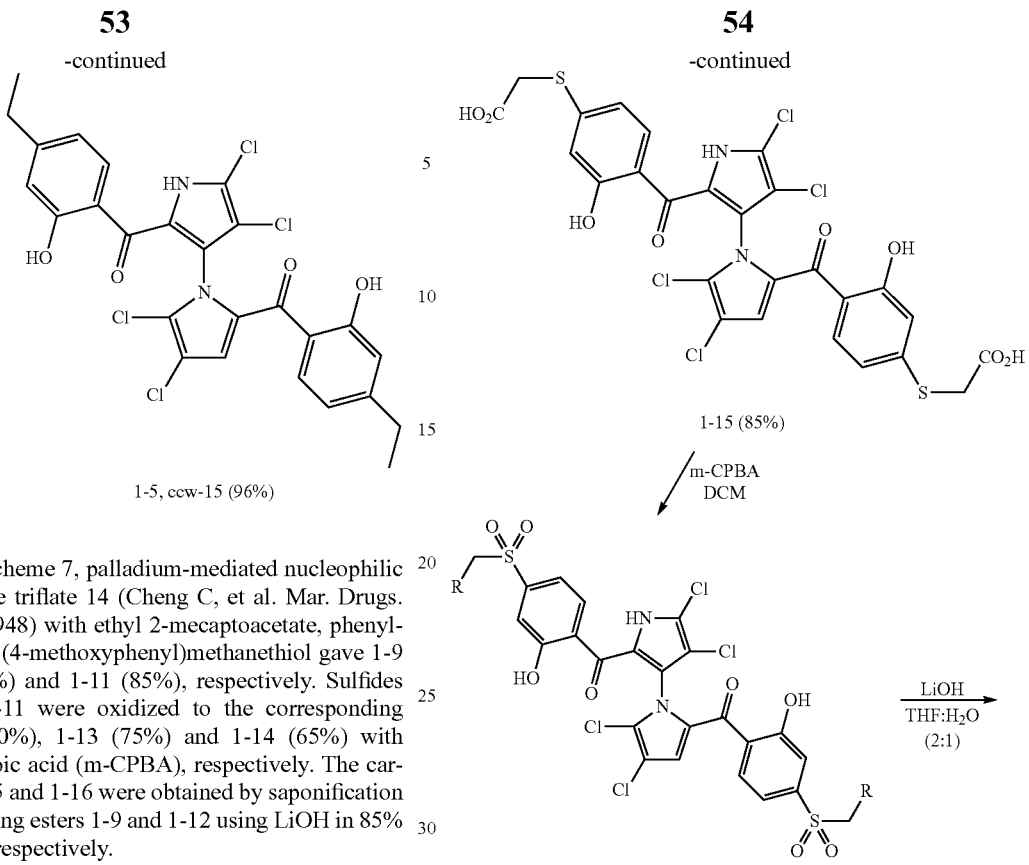

1-5, ccw-15 (96%)

1-15 (85%)

As shown in Scheme 7, palladium-mediated nucleophilic substitution of the triflate 14 (Cheng C, et al. *Mar. Drugs.* 2013, 11, 2927-2948) with ethyl 2-mecaptoacetate, phenylmethanethiol and (4-methoxyphenyl)methanethiol gave 1-9 (61%), 1-10 (96%) and 1-11 (85%), respectively. Sulfides 1-9, 1-10 and 1-11 were oxidized to the corresponding sulfones 1-12 (70%), 1-13 (75%) and 1-14 (65%) with m-chloroperbenzoic acid (m-CPBA), respectively. The carboxylic acids 1-15 and 1-16 were obtained by saponification of the corresponding esters 1-9 and 1-12 using LiOH in 85% and 95% yields, respectively.

Scheme 7. Synthesis of marinopyrroles with sulfide and sulphone spacers.

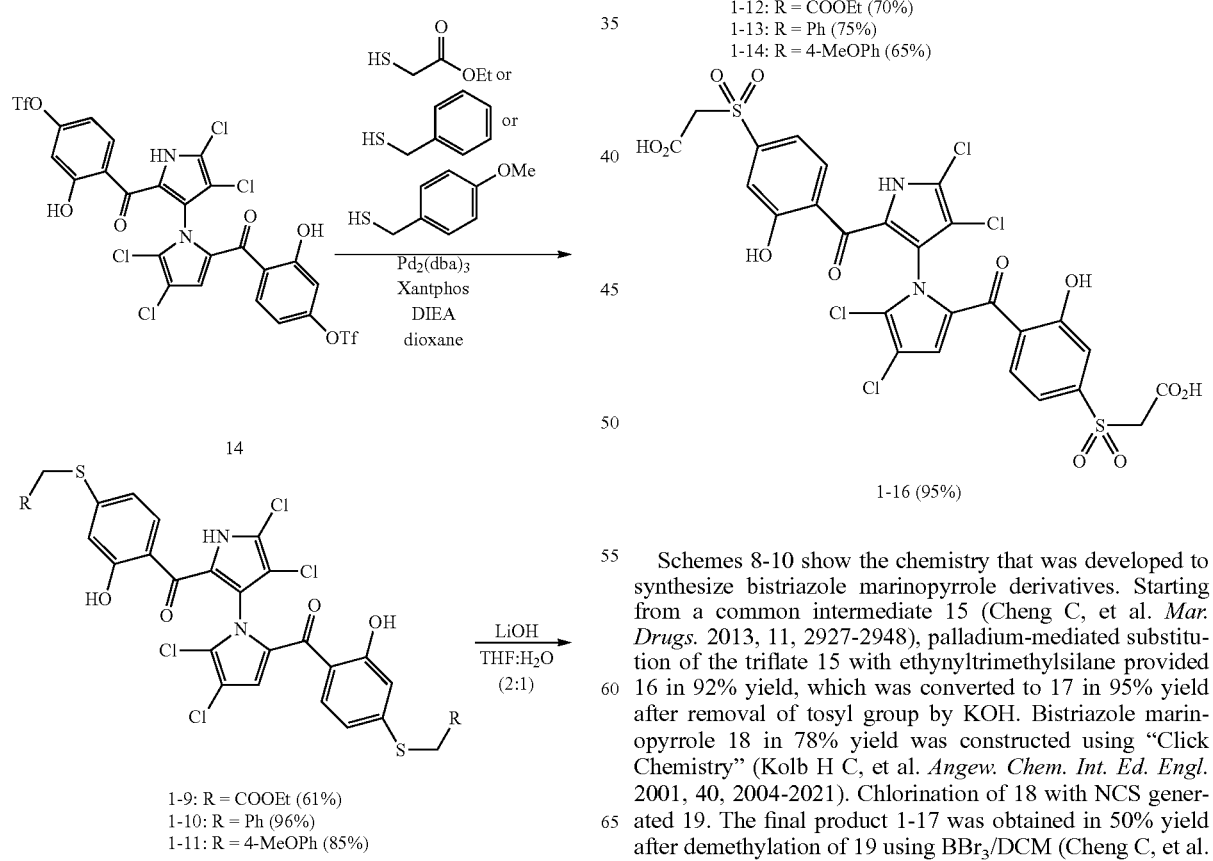

14

1-9: R = COOEt (61%)
1-10: R = Ph (96%)
1-11: R = 4-MeOPh (85%)

1-12: R = COOEt (70%)
1-13: R = Ph (75%)
1-14: R = 4-MeOPh (65%)

1-16 (95%)

Schemes 8-10 show the chemistry that was developed to synthesize bistriazole marinopyrrole derivatives. Starting from a common intermediate 15 (Cheng C, et al. *Mar. Drugs.* 2013, 11, 2927-2948), palladium-mediated substitution of the triflate 15 with ethynyltrimethylsilane provided 16 in 92% yield, which was converted to 17 in 95% yield after removal of tosyl group by KOH. Bistriazole marinopyrrole 18 in 78% yield was constructed using "Click Chemistry" (Kolb H C, et al. *Angew. Chem. Int. Ed. Engl.* 2001, 40, 2004-2021). Chlorination of 18 with NCS generated 19. The final product 1-17 was obtained in 50% yield after demethylation of 19 using BBr$_3$/DCM (Cheng C, et al. *J. Comb. Chem.* 2010, 12, 541-547).

In order to improve overall yield, demethylation of 15 (Cheng C, et al. *Mar. Drugs.* 2013, 11, 2927-2948) using $BBr_3$/DCM was performed first to give 20 in 90% yield, as shown in Scheme 9. Palladium-mediated substitution of the triflate 20 with ethynyltrimethylsilane furnished 21 in 98% yield. Removal of the tosyl group in 21 provided 22 in 95% yield. Intermediate 23 was obtained in 80% yield using "Click Chemistry" (Kolb H C, et al. *Angew. Chem. Int. Ed. Engl.* 2001, 40, 2004-2021), which was subjected to chlorination with NCS to give the final compound 1-18. The free carboxylic acid 1-19 was obtained in 65% yield after removal of butyl group from 1-18.

Compound 1-3 was used as a common starting material by "Click Chemistry" (Kolb H C, et al. *Angew. Chem. Int. Ed. Engl.* 2001, 40, 2004-2021) to produce seven bistriazole marinopyrrole derivatives (1-20-1-26), as shown in Scheme 10. The final compounds 1-20-1-25 were obtained in 55%, 70%, 52%, 48%, 52% and 83% yield, respectively. Removal of $^t$butyl group from 1-25 furnished 1-26 in 94% yield.

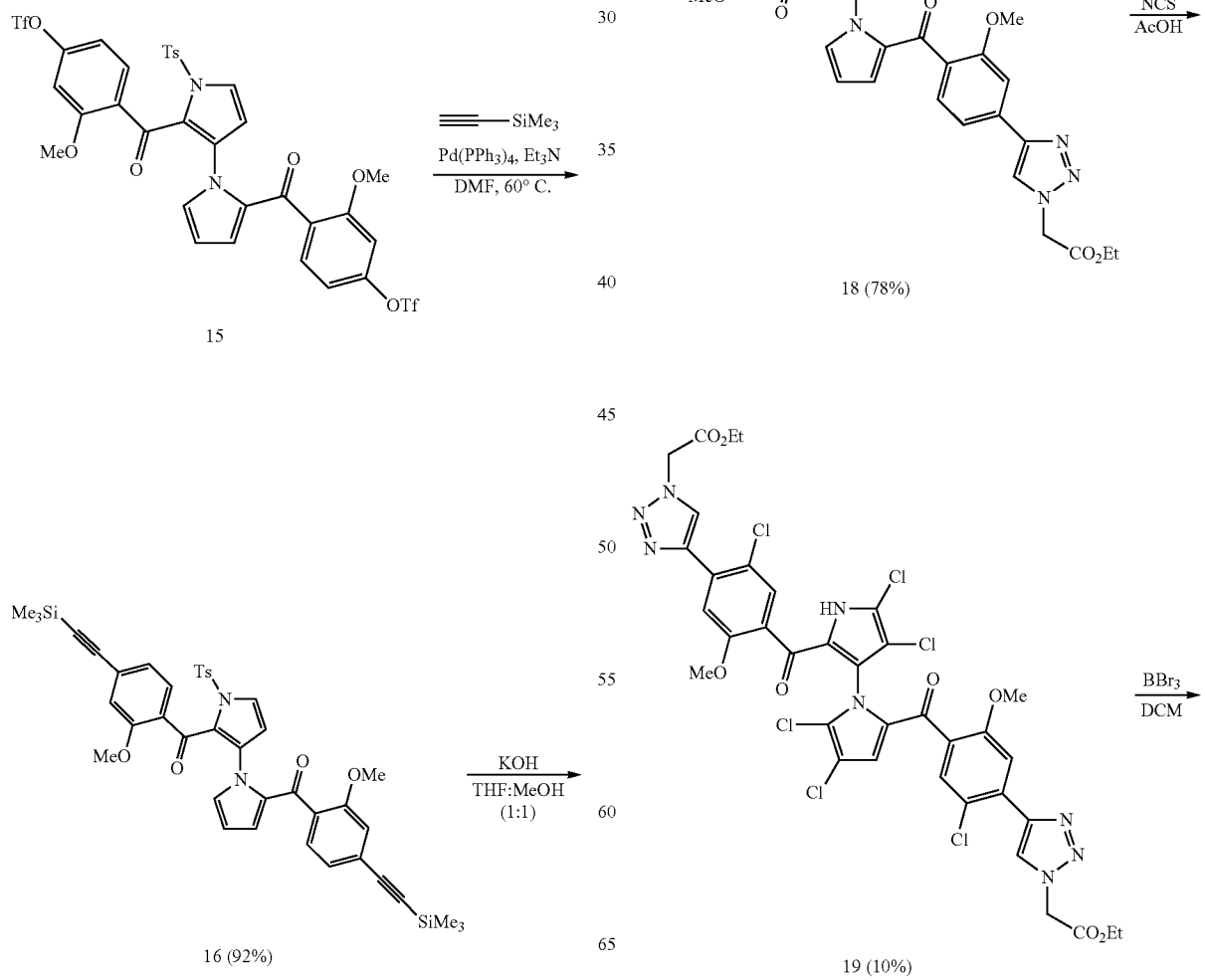

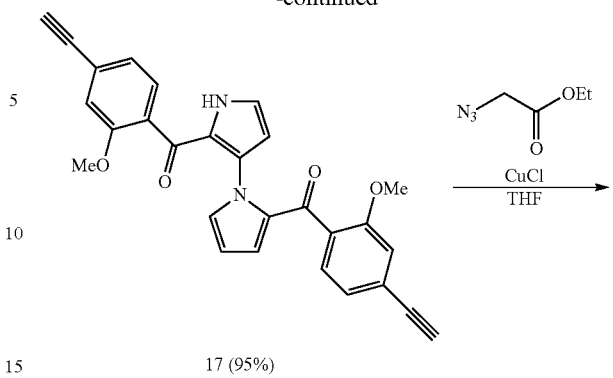

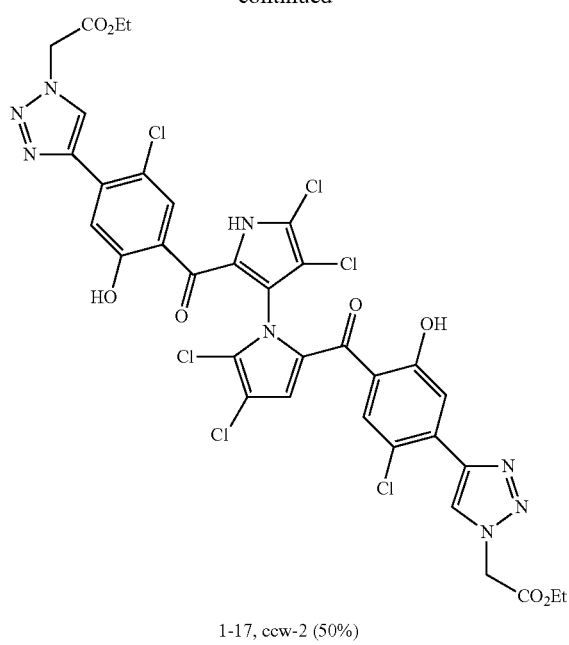
1-17, ccw-2 (50%)
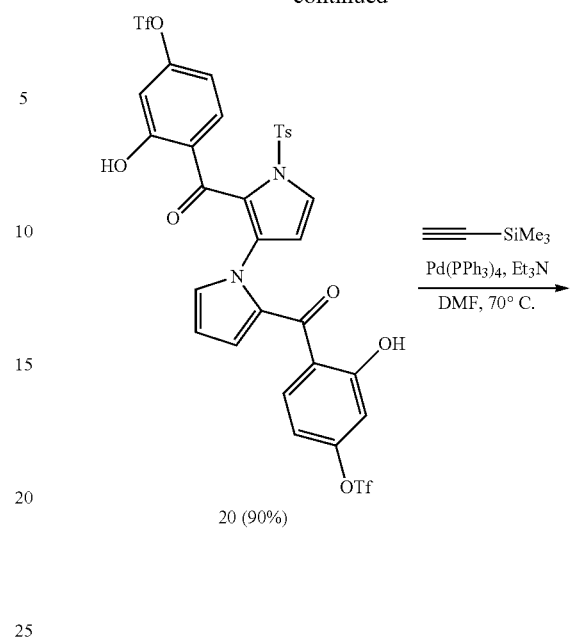
20 (90%)
Scheme 9. Synthesis of triazole-marinopyrroles 1-18 and 1-19
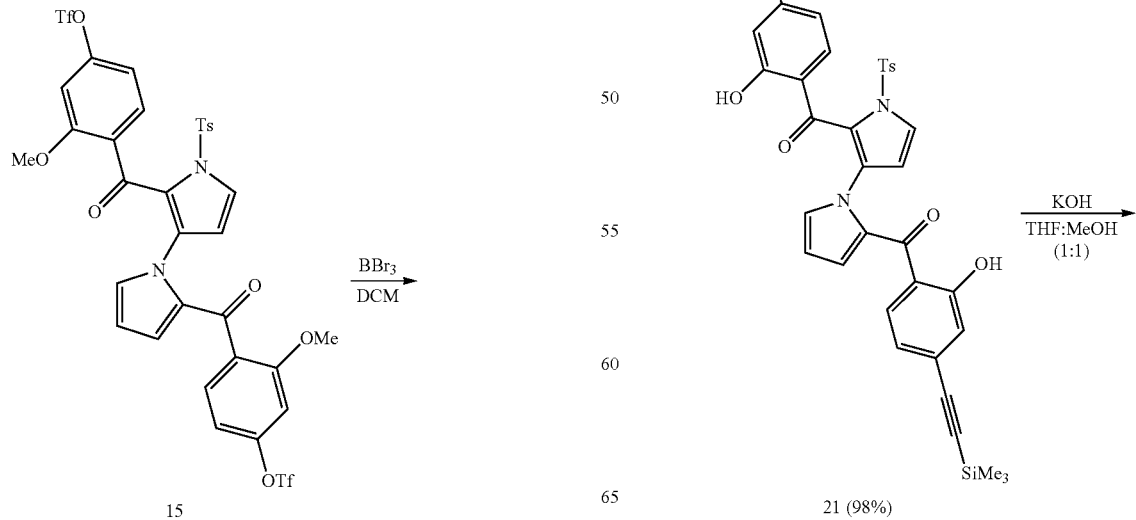
21 (98%)

59
-continued
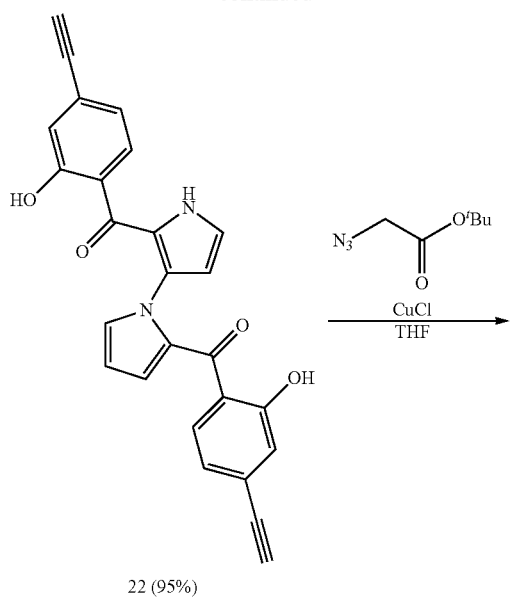
22 (95%)
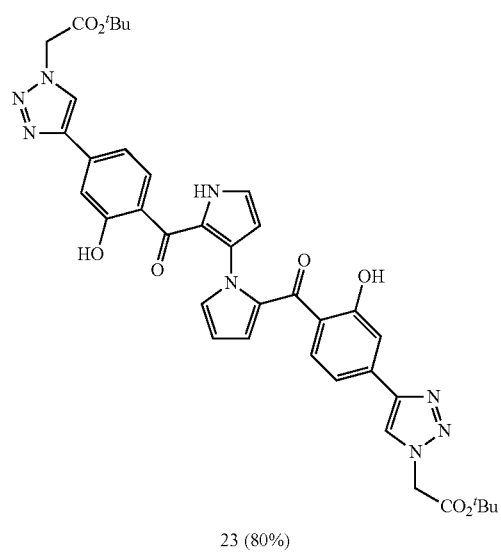
23 (80%)
1-18, ccw3 (14%)
60
-continued
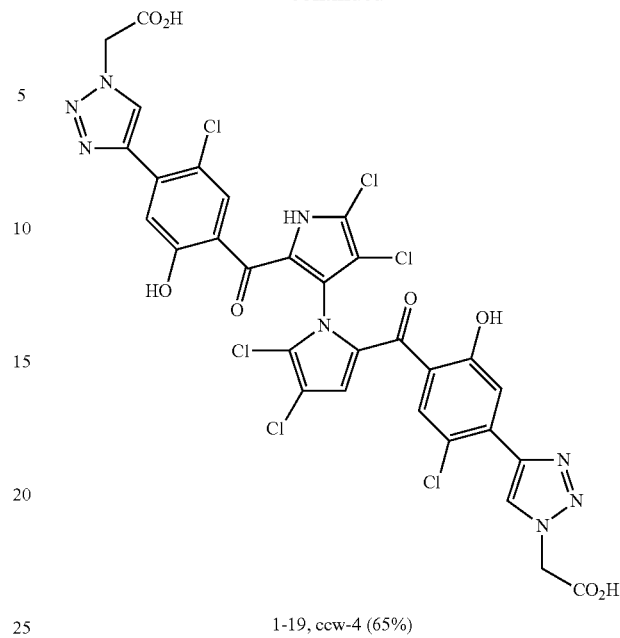
1-19, ccw-4 (65%)
Scheme 10. Synthesis of triazole-marinopyrroles 1-20-1-26.
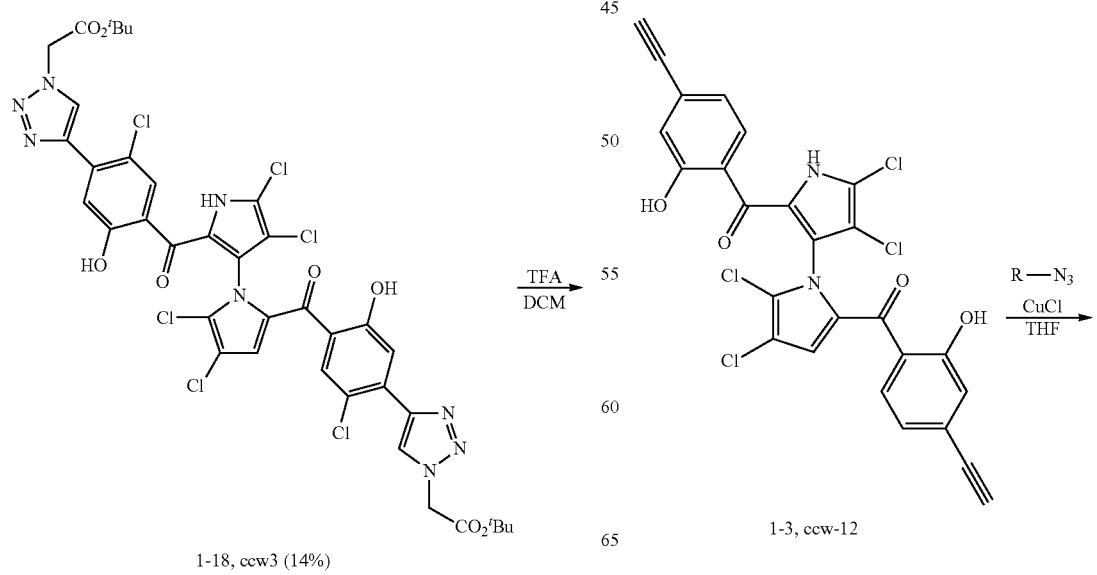
1-3, ccw-12

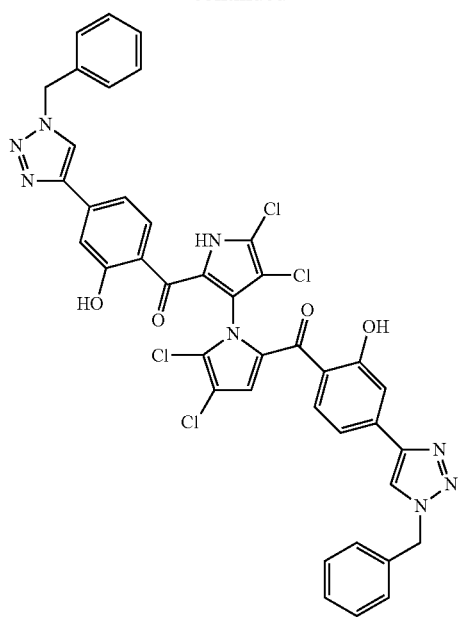
1-20, ccw-8 (55%)
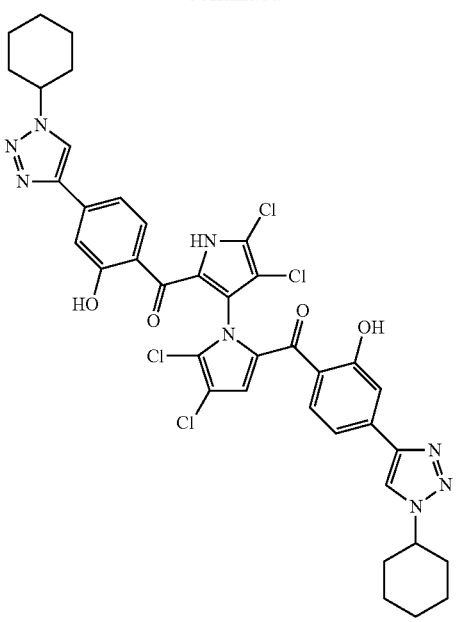
1-22, ccw-10 (52%)
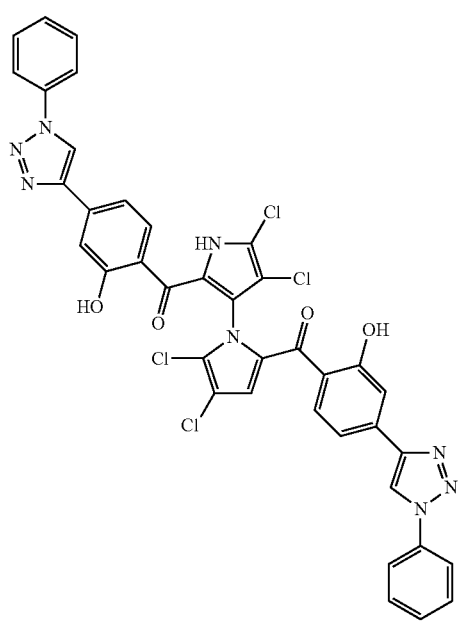
1-21, ccw-9 (70%)
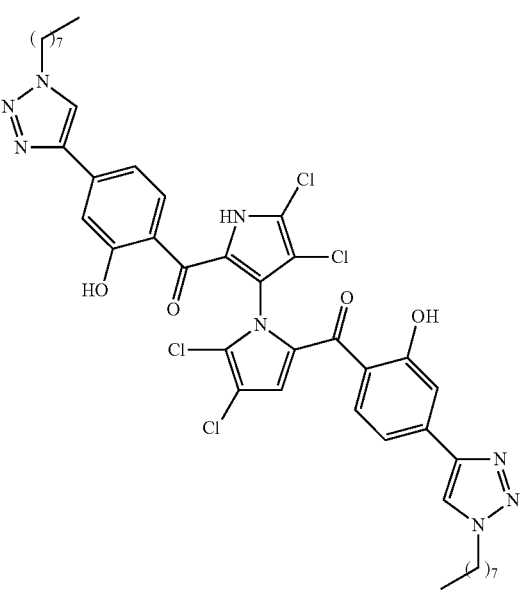
1-23, ccw-11 (48%)

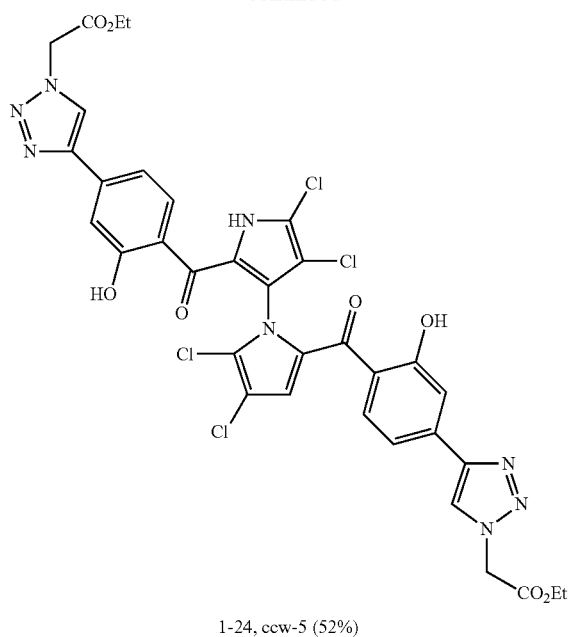

1-24, ccw-5 (52%)

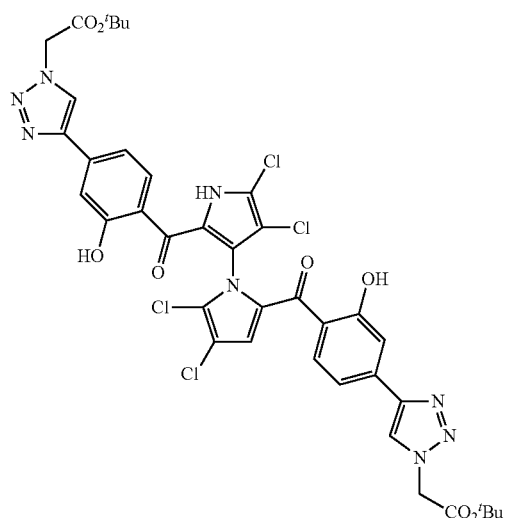

1-25, ccw-6 (83%)

TFA
DCM
→

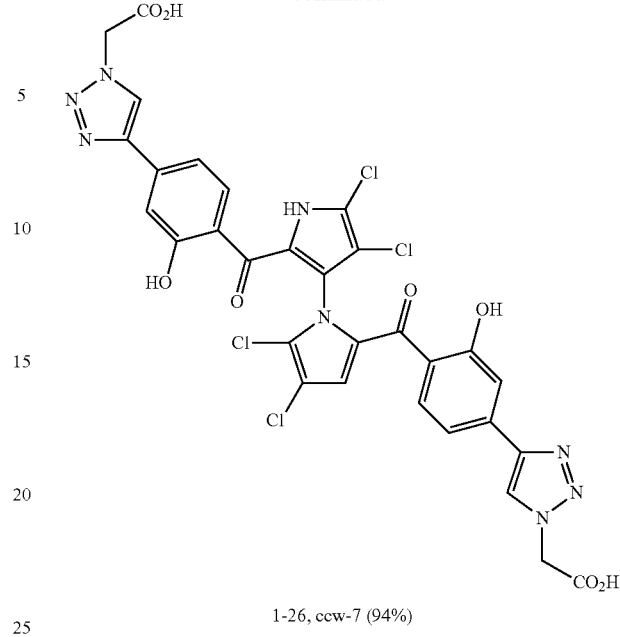

1-26, ccw-7 (94%)

(2-(((tert-Butyldimethylsilyl)oxy)methyl)-1'-tosyl-1'H-1,3'-bipyrrol-2'-yl)(2-methoxy-4-methylphenyl) methanol (3)

To a solution of 1-bromo-2-methoxy-4-methylbenzene (524 mg, 2.62 mmol) in anhydrous THF (5 mL) at −78° C. under $N_2$, n-BuLi (1.15 mL, 2.5 M in n-pentane, 2.88 mmol) was slowly added. After being stirred for 30 min, a solution of 2 (Cheng C, et al. Mar. Drugs. 2013, 11, 2927-2948) (600 mg, 1.31 mmol) in anhydrous THF (1 mL) was added slowly via a syringe. The reaction was stirred for about 8 h and quenched by addition of a saturated aqueous $NH_4Cl$ (15 mL) and extracted with EtOAc (10 mL×3). The combined organic layers were dried over anhydrous sodium sulfate, filtered and concentrated in vacuum. The residue was purified quickly by column chromatography (15% EtOAc/petroleum ether, $R_f$=0.3) to yield 3 (unstable).

(2-(((tert-Butyldimethylsilyl)oxy)methyl)-1'-tosyl-1'H-1,3'-bipyrrol-2'-yl)(2-methoxy-4-methylphenyl) methanone (4)

To a solution of 3 in anhydrous DMSO (20 mL), IBX (618 mg, 2.20 mmol) was added at room temperature. The reaction was allowed to warm up to 30° C. and stirred for about an additional 6 h. The reaction was quenched with water (30 mL) and extracted with EtOAc (15 mL×3). The combined organic layers were dried over anhydrous sodium sulfate, filtered and concentrated in vacuum. The residue was purified by column chromatography (15% EtOAc/petroleum ether, $R_f$=0.2) to yield 4 (550 mg, 73% yield in two steps) as a pale brown solid: melting point 30.7-33.0° C.; $^1$H NMR (400 MHz, $CDCl_3$) δ 0.006 (s, 6H), 0.86 (s, 9H), 2.38 (s, 3H), 2.40 (s, 3H), 3.75 (s, 3H), 4.67 (s, 2H), 6.20 (dd, J=4.0, 2.4 Hz, 1H), 6.32 (d, J=3.2 Hz, 1H), 6.67 (dd, J=4.0, 1.6 Hz, 1H), 6.74 (s, 1H), 6.75 (d, J=7.6 Hz, 1H), 7.06 (dd, J=2.4, 1.6 Hz, 1H), 7.18 (d, J=3.6 Hz, 1H), 7.24-7.28 (m, 3H), 7.84 (d, J=8.8 Hz, 2H) ppm; $^{13}$C NMR ($CDCl_3$, 100 MHz) δ −5.70, −5.70, 18.33, 21.46, 21.71, 25.80, 25.80, 25.80, 53.45, 55.45, 108.90, 111.46, 112.05, 120.34, 121.16, 122.99, 126.70, 126.86, 126.86, 127.20, 129.50, 129.64, 129.64, 129.81, 132.40, 132.62, 136.66, 141.84, 144.60, 157.22, 184.12 ppm; HRMS ESI (M+H$^+$) calculated for $C_{31}H_{39}N_2O_5SSi$ 579.2349. found 579.2358; IR (KBr) 3434, 3443, 2954, 2930, 2856, 1916, 1708, 1936, 1608, 1498, 1409, 1368, 1256, 1179, 1035, 839, 772, 670, 602 cm$^{-1}$.

(2-(Hydroxymethyl)-1'-tosyl-1'H-1,3'-bipyrrol-2'-yl)(2-methoxy-4-methylphenyl)methanone (5)

To a solution of 4 (550 mg, 0.95 mmol) in anhydrous THF (10 mL), TBAF (745 mg, 2.85 mmol) was added at room temperature. The reaction was allowed to stir for about an additional 5 h at room temperature. The reaction was quenched with water (10 mL) and extracted with EtOAc (10 mL×3). The combined organic layers were dried over anhydrous sodium sulfate, filtered and concentrated in vacuum. The residue was purified by column chromatography (20% EtOAc/petroleum ether, $R_f$=0.3) to yield 5 (397 mg, 90% yield) as a brown-red solid: melting point 29.9-31.7° C.; $^1$H NMR (400 MHz, CDCl$_3$) δ 2.38 (s, 3H), 2.40 (s, 3H), 2.97 (t, J=6.8 Hz, 1H), 3.74 (s, 3H), 4.55 (d, J=6.8 Hz, 2H), 6.23 (dd, J=4.0, 2.4 Hz, 1H), 6.34 (d, J=3.6 Hz, 1H), 6.63 (dd, J=4.0, 1.6 Hz, 1H), 6.73 (s, 1H), 6.76 (d, J=7.6 Hz, 1H), 7.00 (dd, J=2.4, 2.0 Hz, 1H), 7.22 (d, J=7.6 Hz, 1H), 7.28 (d, J=3.6 Hz, 1H), 7.32 (d, J=8.0 Hz, 2H), 7.85 (d, J=8.4 Hz, 2H) ppm; $^{13}$C NMR (CDCl$_3$, 100 MHz) δ 21.50, 21.70, 55.02, 55.48, 109.61, 110.85, 112.06, 120.41, 121.03, 123.68, 126.61, 127.08, 127.08, 128.22, 128.72, 129.27, 129.95, 129.95, 132.60, 132.82, 135.73, 141.93, 145.21, 157.09, 185.16 ppm; HRMS ESI (M+Na$^+$) calculated for $C_{25}H_{24}N_2NaO_5S$, 487.1304. found 487.1297; IR (KBr) 3445, 3141, 2956, 2930, 1771, 1702, 1631, 1609, 1498, 1461, 1410, 1366, 1177, 1138, 1034, 1014, 931, 720 cm$^{-1}$.

2'-(2-Methoxy-4-methylbenzoyl)-1'-tosyl-1'H-1,3'-bipyrrole-2-carbaldehyde (6)

To a solution of 5 (413 mg, 0.89 mmol) in DMSO (20 mL), IBX (374 mg, 1.33 mmol) was added at room temperature. The reaction was allowed to warm up to 50° C. and stirred for about 3 h. The reaction was quenched with water (30 mL) and extracted with EtOAc (15 mL×3). The combined organic layers were dried over anhydrous sodium sulfate, filtered and concentrated in vacuum. The residue was purified by column chromatography (15% EtOAc/petroleum ether, $R_f$=0.3) to yield 6 (370 mg, 90% yield) as a white solid: melting point 116.4-118.0° C.; $^1$H NMR (400 MHz, CDCl$_3$) δ 2.38 (s, 3H), 2.42 (s, 3H), 3.73 (s, 3H), 6.27 (s, 1H), 6.45 (d, J=3.2 Hz, 1H), 6.68 (d, J=2.0 Hz, 1H), 6.72 (s, 1H), 6.76 (d, J=7.6 Hz, 1H), 6.99 (s, 1H), 7.30 (d, J=8.0 Hz, 1H), 7.34 (d, J=8.0 Hz, 2H), 7.68 (d, J=3.2 Hz, 1H), 7.89 (d, J=8.0 Hz, 2H), 9.62 (s, 1H) ppm; $^{13}$C NMR (CDCl$_3$, 100 MHz) δ 21.53, 21.69, 55.41, 109.99, 111.43, 112.02, 120.41, 123.04, 125.22, 125.99, 127.50, 127.94, 127.94, 129.80, 129.83, 129.83, 131.70, 133.68, 134.72, 139.12, 142.26, 145.71, 157.32, 176.91, 184.11 ppm; HRMS ESI (M+$^H$) calculated for $C_{25}H_{23}N_2O_5S$, 463.1328. found 463.1336; IR (KBr) 3449, 3150, 3129, 2957, 2924, 2854, 1690, 1671, 1606, 1565, 1408, 1357, 1263, 1170, 1073, 1009, 773 cm$^{-1}$.

(2-(Hydroxy(2-methoxy-4-methylphenyl)methyl)-1'-tosyl-1'H-1,3'-bipyrrol-2'-yl)(2-methoxy-4-methylphenyl)methanone (7)

To a solution of 1-bromo-2-methoxy-4-methylbenzene (378 mg, 1.89 mmol) in anhydrous THF (5 mL) at −78° C. under N$_2$, t-BuLi (1.46 mL, 1.3 M, 1.89 mmol) was slowly added. After being stirred for 30 min, a solution of 6 (350 mg, 0.76 mmol) in anhydrous THF (1 mL) was added slowly via a syringe. The reaction was stirred for about 8 h, quenched by addition of a saturated aqueous NH$_4$Cl (15 mL), and extracted with EtOAc (10 mL×3). The combined organic layers were dried over anhydrous sodium sulfate, filtered and concentrated in vacuum. The residue was purified quickly by column chromatography (12% EtOAc/petroleum ether, $R_f$=0.3) to yield 7 (unstable).

(1'-Tosyl-1'H-1,3'-bipyrrole-2,2'-diyl)bis((2-methoxy-4-methylphenyl)methanone) (8)

To a solution of 7 in anhydrous DMSO (20 mL), IBX (275 mg, 0.98 mmol) was added at room temperature. After being stirred for about 3 h, the reaction was quenched with water (30 mL) and extracted with EtOAc (15 mL×3). The combined organic layers were dried over anhydrous sodium sulfate, filtered and concentrated in vacuum. The residue was purified by column chromatography (12% EtOAc/petroleum ether, $R_f$=0.2) to yield 8 (240 mg, 54% yield two steps) as a pale brown solid: melting point 71.0-72.7° C.; $^1$H NMR (400 MHz, CDCl$_3$) δ 2.27 (s, 3H), 2.37 (s, 3H), 3.43 (s, 3H), 3.65 (s, 3H), 3.75 (s, 3H), 5.85 (t, J=3.2 Hz, 1H), 6.29 (dd, J=4.0, 1.6 Hz, 1H), 6.46-6.48 (m, 2H), 6.53 (d, J=8.0 Hz, 1H), 6.70 (d, J=8.0 Hz, 1H), 6.73 (s, 2H), 6.96 (d, J=7.6 Hz, 1H), 7.28 (d, J=8.0 Hz, 1H), 7.33 (d, J=8.0 Hz, 2H), 7.49 (d, J=3.6 Hz, 1H), 7.94 (d, J=8.0 Hz, 2H) ppm; $^{13}$C NMR (CDCl$_3$, 100 MHz) δ 21.50, 21.62, 21.79, 55.39, 55.39, 108.52, 111.61, 111.99, 112.04, 119.88, 120.37, 122.95, 123.41, 124.79, 126.25, 128.07, 128.07, 128.61, 129.41, 129.41, 129.41, 129.73, 131.48, 132.17, 132.29, 135.78, 141.65, 144.24, 144.81, 157.25, 158.29, 183.15, 184.47 ppm; HRMS ESI (M+H$^+$) calculated for $C_{33}H_{31}N_2O_6S$. found 583.1903. found 583.1890; IR (KBr) 3356, 3006, 2958, 2851, 1631, 1612, 1463, 1408, 1262, 1157, 1088, 1033, 859, 746 cm$^{-1}$.

1'H-1,3'-bipyrrole-2,2'-diylbis((2-methoxy-4-methylphenyl)methanone) (9)

To a solution of 8 (210 mg, 0.36 mmol) in a mixture of MeOH/THF (1:1, 5 mL), KOH (60 mg, 1.08 mmol) was added at room temperature. After being stirred for 15 min, the reaction was adjusted to pH 7.0 with 0.5 N HCl and extracted with EtOAc (10 mL×3). The combined organic layers were dried over anhydrous sodium sulfate, filtered and concentrated in vacuum. The residue was purified by column chromatography (33% EtOAc/petroleum ether, $R_f$=0.3) to yield 9 (151 mg, 98% yield) as a light white solid: melting point 171.1-172.3° C.; $^1$H NMR (400 MHz, CDCl$_3$) δ 2.25 (s, 3H), 2.38 (s, 3H), 3.67 (s, 3H), 3.77 (s, 3H), 5.80-5.82 (m, 1H), 6.30 (t, J=2.8 Hz, 1H), 6.35 (dd, J=4.0, 1.6 Hz, 1H), 6.46-6.48 (m, 2H), 6.62 (t, J=2.8 Hz, 1H), 6.73-6.74 (m, 2H), 7.02 (t, J=2.8 Hz, 1H), 7.08 (dd, J=9.6, 7.6 Hz, 2H), 9.40 (br s, 1H) ppm; $^{13}$C NMR (CDCl$_3$, 100 MHz) δ 21.78, 21.81, 55.33, 55.58, 108.32, 110.60, 111.35, 112.20, 119.99, 120.63, 122.76, 122.98, 125.23, 125.92, 126.77, 129.01, 129.89, 131.13, 132.22, 132.34, 141.51, 141.55, 156.69, 157.43, 183.43, 183.90 ppm; HRMS ESI (M+H$^+$) calculated for $C_{26}H_{25}N_2O_4$ 429.1814. found 429.1811; IR (KBr) 3357, 3006, 2957, 2852, 1631, 1612, 1462, 1408, 1264, 1127, 1033, 859, 747 cm$^{-1}$.

(4,4',5,5'-Tetrachloro-1'H-1,3'-bipyrrole-2,2'-diyl)bis((5-chloro-2-methoxy-4-methylphenyl)methanone) (10)

To a solution of 9 (10 mg, 0.02 mmol) in anhydrous MeCN (1 mL) at room temperature, NCS (18.7 mg, 0.14 mmol) was added slowly. After being stirred for about 20 min at room temperature, the reaction was quenched with water (5 mL) and extracted with EtOAc (5 mL×3). The combined organic layers were dried over anhydrous sodium sulfate, filtered and concentrated in vacuum. The residue was purified by column chromatography (12% EtOAc/petroleum ether, $R_f$=0.2) to yield 10 (9 mg, 65% yield) as a pale brown solid: melting point 78.3-80.0° C.; $^1$H NMR (400 MHz, CDCl$_3$) δ 2.30 (s, 3H), 2.32 (s, 3H), 3.72 (s, 3H), 3.76 (s, 3H), 6.44 (s, 1H), 6.67 (s, 1H), 6.80 (s, 1H), 7.06 (s, 1H), 7.20 (s, 1H), 9.90-10.10 (br s, 1H) ppm; $^{13}$C NMR (CDCl$_3$, 100 MHz) δ 20.54, 20.65, 55.80, 55.89, 110.91, 111.82, 113.10, 114.04, 120.46, 120.80, 124.20, 124.75, 124.87, 125.07, 125.31, 126.30, 128.27, 128.66, 129.86, 130.65, 139.95, 140.16, 155.25, 156.06, 180.59, 180.86 ppm; HRMS ESI (M+H$^+$) calculated for C$_{26}$H$_{19}$Cl$_6$N$_2$O$_4$ 632.9476. found 632.9492; IR (KBr) 3232, 2955, 2918, 2849, 1736, 1644, 1604, 1462, 1428, 1401, 1172, 1039, 871, 678 cm$^{-1}$.

(4,4',5,5'-Tetrachloro-1'H-1,3'-bipyrrole-2,2'-diyl)bis((5-chloro-2-hydroxy-4-methylphenyl)methanone) (1-2)

To a solution of 10 (47 mg, 0.07 mmol) in anhydrous CH$_2$Cl$_2$ (5 mL), a solution of BBr$_3$ (75 mg, 0.30 mmol) in anhydrous CH$_2$Cl$_2$ (1 mL) was slowly added via a syringe under N$_2$ at −78° C. After being stirred for 0.5 h, the reaction was quenched by addition of water (10 mL) and extracted with CH$_2$Cl$_2$ (10 mL×3). The combined organic layers were dried over anhydrous sodium sulfate, filtered and concentrated in vacuum. The residue was purified by column chromatography (12% EtOAc/petroleum ether, $R_f$=0.2) to yield 10 (38 mg, 85% yield) as a pale brown solid: melting point 84.7-86.0° C.; $^1$H NMR (400 MHz, CDCl$_3$) δ 2.32 (s, 3H), 2.39 (s, 3H), 6.76 (s, 1H), 6.80 (s, 1H), 6.90 (s, 1H), 7.39 (s, 2H), 9.89 (br s, 1H), 10.29 (s, 1H), 10.98 (s, 1H) ppm; $^{13}$C NMR (CDCl$_3$, 100 MHz) δ 20.72, 20.80, 113.28, 117.53, 117.77, 119.80, 119.82, 120.40, 120.44, 120.74, 120.76, 123.34, 123.43, 124.38, 124.72, 128.60, 129.65, 130.91, 145.51, 145.71, 159.52, 160.76, 184.34, 185.20 ppm; HRMS ESI (M+H$^+$) calculated for C$_{24}$H$_{15}$C$_{16}$N$_2$O$_4$ 604.9163. found 604.9168; IR (KBr) 3415, 3238, 2955, 2927, 2856, 1628, 1595, 1479, 1430, 1215, 1027, 871, 690 cm$^{-1}$. HPLC purity, 95.6% (Flow rate: 1.0 mL/min; Column: Agilent ZORBAX 300SB-C8, 5 μm, 150×4.6 mm; Wavelength: UV 254 nm; Temperature: 25° C.; Mobile phase: MeOH:H$_2$O=75:25; $t_R$=9.0 min).

(4,4',5,5'-Tetrachloro-1'-tosyl-1'H-1,3'-bipyrrole-2,2'-diyl)bis((2-methoxy-4-((trimethylsilyl)ethynyl)phenyl)methanone) (12)

Under N$_2$, a mixture of 11 (Cheng C, et al. Mar. Drugs. 2013, 11, 2927-2948) (300 mg, 0.30 mmol), ethynyltrimethylsilane (176 mg, 1.80 mmol), Pd(PPh$_3$)$_4$ (70 mg, 0.06 mmol) and Et$_3$N (30 mg, 0.30 mmol) was dissolved in anhydrous DMF (5 mL). The reaction was allowed to stir for about 16 h at room temperature. The reaction was quenched with water (15 mL) and extracted with EtOAc (10 mL×3). The combined organic layers were dried over anhydrous sodium sulfate, filtered and concentrated in vacuum. The residue was purified by column chromatography (10% EtOAc/petroleum ether, $R_f$=0.3) to yield 12 (199 mg, 74% yield) as a light yellow solid: melting point 118.7-120.0° C.; $^1$H NMR (400 MHz, acetone-d$_6$) δ 0.25 (s, 18H), 2.54 (s, 3H), 3.56 (s, 3H), 3.63 (s, 3H), 6.52 (s, 1H), 6.69 (d, J=8.0 Hz, 1H), 6.93 (d, J=2.8 Hz, 2H), 7.04 (dd, J=8.0, 1.2 Hz, 1H), 7.13 (d, J=7.6 Hz, 1H), 7.49 (d, J=8.0 Hz, 1H), 7.60 (d, J=8.0 Hz, 2H), 7.96 (d, J=8.4 Hz, 2H) ppm; $^{13}$C NMR (CDCl$_3$, 100 MHz) δ −0.18, −0.18, −0.18, −0.14, −0.14, −0.14, 21.72, 56.11, 56.11, 96.70, 97.96, 104.84, 105.05, 114.43, 114.66, 115.16, 116.20, 117.25, 118.20, 120.38, 121.80, 123.55, 124.09, 124.78, 127.79, 127.98, 129.23, 129.23, 129.80, 130.33, 131.02, 131.02, 131.10, 131.64, 134.42, 134.99, 147.58, 158.07, 159.35, 181.79, 183.11 ppm; HRMS ESI (M+H$^+$) calculated for C$_{41}$H$_{39}$Cl$_4$N$_2$O$_6$SSi$_2$ 883.0821. found 883.0812; IR (KBr) 3445, 2960, 2857, 2159, 1654, 1600, 1556, 1456, 1400, 1268, 1250, 1192, 1034, 951, 851 cm$^{-1}$.

(4,4',5,5'-Tetrachloro-1'-tosyl-1'H-1,3'-bipyrrole-2,2'-diyl)bis((2-hydroxy-4-((trimethylsilyl)ethynyl)phenyl)methanone) (13)

To a solution of 12 (43 mg, 0.05 mmol) in anhydrous CH$_2$Cl$_2$ (5 mL), a solution of BBr$_3$ (61 mg, 0.24 mmol) in anhydrous CH$_2$Cl$_2$ (1 mL) was slowly added via a syringe under N$_2$ at −78° C. After being stirred for 30 min, the reaction was quenched by addition of water (10 mL) and extracted with CH$_2$Cl$_2$ (10 mL×3). The combined organic layers were dried over anhydrous sodium sulfate, filtered and concentrated in vacuum. The residue was purified by column chromatography (10% EtOAc/petroleum ether, $R_f$=0.2) to yield 13 (22 mg, 53% yield) as a pale brown solid: melting point 97.3-99.7° C.; $^1$H NMR (400 MHz, acetone-d$_6$) δ 0.27 (s, 18H), 2.52 (s, 3H), 6.86 (s, 1H), 6.91-6.93 (m, 2H), 6.96 (d, J=8.8 Hz, 1H), 7.44 (d, J=8.0 Hz, 1H), 7.50 (d, J=8.0 Hz, 1H), 7.56 (d, J=8.0 Hz, 3H), 7.90 (d, J=8.4 Hz, 2H) ppm; $^{13}$C NMR (CDCl$_3$, 100 MHz) δ −0.23, −0.23, −0.23, −0.23, −0.23, −0.23, 21.84, 99.67, 103.39, 103.72, 106.30, 112.25, 113.64, 113.86, 120.07, 120.83, 121.20, 121.25, 121.35, 122.60, 122.62, 122.80, 124.44, 128.25, 128.25, 128.26, 130.14, 130.14, 131.68, 131.94, 131.98, 133.23, 133.80, 146.95, 146.95, 162.00, 162.00, 180.55, 188.94 ppm; HRMS ESI (M+H$^+$) calculated for C$_{39}$H$_{35}$Cl$_4$N$_2$O$_6$SSi$_2$ 855.0508. found 855.0502; IR (KBr) 2957, 2923, 2852, 2159, 1728, 1624, 1547, 1382, 1343, 1245, 1191, 973, 850, 662 cm$^{-1}$.

(4,4',5,5'-Tetrachloro-1'H-1,3'-bipyrrole-2,2'-diyl)bis((4-ethynyl-2-hydroxyphenyl)methanone) (1-3)

To a solution of 13 (22 mg, 0.03 mmol) in a mixture of MeOH/THF (1:1, 3 mL), KOH (7.2 mg, 0.13 mmol) was added at room temperature. After being stirred for 15 min, the reaction was adjusted to pH 7.0 with 0.5 N HCl and extracted with EtOAc (10 mL×3). The combined organic layers were dried over anhydrous sodium sulfate, filtered and concentrated in vacuum. The residue was purified by column chromatography (15% EtOAc/petroleum ether, $R_f$=0.2) to yield 1-3 (13 mg, 91% yield) as a light yellow solid: melting point 83.3-84.1° C.; $^1$H NMR (400 MHz, acetone-d$_6$) δ 3.90 (s, 1H), 4.00 (s, 1H), 6.49 (s, 1H), 6.81 (d, J=8.0 Hz, 1H), 7.02 (d, J=8.4 Hz, 1H), 7.05 (s, 1H), 7.54 (t, J=8.4 Hz, 3H), 10.50 (s, 1H), 10.82 (s, 1H) 12.39 (br s, 1H) ppm; $^{13}$C NMR (CDCl$_3$, 100 MHz) δ 78.81, 82.37, 82.99, 83.19, 109.91, 120.99, 121.00, 121.09, 121.19, 121.81, 122.40, 122.75, 123.54, 124.80, 125.28, 129.32, 130.71, 131.35, 134.03, 137.85, 141.50, 142.85, 161.00, 161.22, 185.62, 186.50 ppm; HRMS ESI (M+H$^+$) calculated for C$_{26}$H$_{13}$Cl$_4$N$_2$O$_4$ 556.9629. found 556.9632; IR (KBr) 3405, 3295, 2969, 2929, 2108, 1701, 1624, 1594, 1551, 1448, 1393, 1332, 1246, 1120, 965, 788, 675 cm$^{-1}$. HPLC purity, 99.1% (Flow rate: 1.0 mL/min; Column: Agilent ZORBAX 300SB-C8, 5 μm, 150×4.6 mm; Wavelength: UV 254 nm; Temperature: 25° C.; Mobile phase: MeOH: $H_2O$=70:30; $t_R$=5.7 min).

(4,4',5,5'-Tetrachloro-1'H-1,3'-bipyrrole-2,2'-diyl)bis ((2-hydroxy-4-vinylphenyl)methanone) (1-4)

Under 1 atm $H_2$, 1-3 (100 mg, 0.18 mmol) and Pd/BaSO$_4$ (5 mg) were dissolved in MeOH (3 mL). The reaction was allowed to cool to 10° C. and stirred for about 30 min. The suspension was filtered and the filtrate was washed with EtOAc (50 mL). The combined organic layers were concentrated in vacuum and the residue was purified by column chromatography (20% EtOAc/petroleum ether, $R_f$=0.2) to yield 1-4 (61 mg, 60% yield) as a yellow solid: melting point 76.4-77.7° C.; $^1$H NMR (400 MHz, acetone-d$_6$) δ 5.41 (d, J=10.8 Hz, 1H), 5.49 (d, J=11.2 Hz, 1H), 5.95 (d, J=17.6 Hz, 1H), 6.04 (d, J=17.6 Hz, 1H), 6.50 (s, 1H), 6.95-6.79 (m, 2H), 6.81 (dd, J=8.0, 1.2 Hz, 1H), 6.98 (d, J=1.2 Hz, 1H), 7.03 (s, 1H), 7.07 (d, J=8.4 Hz, 1H), 7.49 (d, J=7.2 Hz, 1H), 7.57 (d, J=8.4 Hz, 1H), 11.16 (s, 1H) ppm; $^{13}$C NMR (acetone-d$_6$, 100 MHz) δ 90.24, 107.07, 109.66, 111.20, 115.52, 115.60, 117.12, 118.04, 118.27, 119.04, 119.89, 128.70, 130.80, 131.83, 134.74, 136.58, 136.60, 137.88, 145.64, 147.00, 152.18, 162.22, 171.91, 172.95, 185.92, 186.38 ppm; HRMS ESI (M+H$^+$) calculated for $C_{26}H_{17}Cl_4N_2O_4$ 560.9942. found 560.9952; IR (KBr) 3423, 3275, 2961, 2926, 1920, 1847, 1737, 1626, 1575, 1499, 1450, 1390, 1353, 1216, 887, 797, 723 cm$^{-1}$. HPLC purity, 99.2% (Flow rate, 1.0 mL/min; Column, Agilent ZORBAX 300SB-C8, 5 μm, 150×4.6 mm; Wavelength: UV 254 nm; Temperature: 25° C.; Mobile phase: MeOH:$H_2O$=90:10; $t_R$=5.1 min).

(4,4',5,5'-Tetrachloro-1'H-1,3'-bipyrrole-2,2'-diyl)bis ((4-ethyl-2-hydroxyphenyl)methanone) (1-5)

Under 1 atm $H_2$, 1-4 (50 mg, 0.09 mmol) and Pd/BaSO$_4$ (5 mg) were dissolved in MeOH (3 mL). The reaction was allowed to stir for about 3 h at room temperature. The suspension was filtered and the filtrate was washed with EtOAc (50 mL). The combined organic layers were concentrated in vacuum and the residue was purified by column chromatography (12% EtOAc/petroleum ether, $R_f$=0.2) to yield 1-5 (48 mg, 96% yield) as a yellow solid: melting point 90.3-92.0° C.; $^1$H NMR (400 MHz, acetone-d$_6$) δ 1.17-1.24 (m, 6H), 2.59 (dd, J=15.2, 7.6 Hz, 2H), 2.65 (dd, J=15.2, 7.6 Hz, 2H), 6.47 (s, 1H), 6.53 (dd, J=8.4, 2.8 Hz, 1H), 6.77-6.80 (m, 3H), 7.35 (br s, 1H), 7.47 (d, J=8.0 Hz, 1H), 10.80 (br s, 1H), 11.24 (s, 1H), 12.27 (br s, 1H) ppm; $^{13}$C NMR (acetone-d$_6$, 100 MHz) δ 15.01, 15.01, 15.59, 15.59, 109.53, 117.00, 117.16, 118.24, 118.34, 119.10, 120.31, 121.72, 124.79, 126.30, 128.10, 131.56, 131.56, 134.54, 154.47, 154.47, 156.17, 156.17, 163.15, 163.41, 186.65, 188.42 ppm; HRMS ESI (M+H$^+$) calculated for $C_{26}H_{21}Cl_4N_2O_4$ 565.0255. found 565.0261; IR (KBr) 3420, 3251, 2967, 2932, 1628, 1590, 1500, 1450, 1393, 1258, 1124, 944, 792, 531 cm$^{-1}$. HPLC purity, 97.5% (Flow rate: 1.0 mL/min; Column, Agilent ZORBAX 300SB-C8, 5 m, 150×4.6 mm; Wavelength: UV 254 nm; Temperature: 25° C.; Mobile phase: MeOH:$H_2O$=75:25; $t_R$=9.4 min).

(4,4',5,5'-Tetrachloro-1'H-1,3'-bipyrrole-2,2'-diyl)bis (((2-hydroxy-4-(3-ethylacetate)thiophenyl)methanone) (1-9)

Under $N_2$, a mixture of 14 (Cheng C, et al. *Mar. Drugs.* 2013, 11, 2927-2948) (50 mg, 0.06 mmol), ethyl 2-mercaptoacetate (33 mg, 0.24 mmol), Pd$_2$(dba)$_3$ (2 mg, 0.003 mmol), Xantphos (4 mg, 0.006 mmol) and i-Pr$_2$NEt (31 mg, 0.24 mmol) was dissolved in 1,4-dioxane (5 mL). The reaction was heated to reflux and stirred for about 10 h. The reaction was quenched with water (10 mL) and extracted with EtOAc (15 mL×3). The combined organic layers were dried over anhydrous sodium sulfate, filtered and concentrated in vacuum. The residue was purified by flash column chromatography (33% EtOAc/petroleum ether, $R_f$=0.3) to yield 1-9 (28 mg, 61%) as a yellow solid: melting point 51.8-53.3° C.; $^1$H NMR (400 MHz, CDCl$_3$) δ 1.24-1.29 (m, 6H), 3.71 (s, 2H), 3.76 (s, 2H), 4.19-4.25 (m, 4H), 6.11 (s, 1H), 6.46 (d, J=8.4 Hz, 1H), 6.73 (d, J=8.0 Hz, 1H), 6.80 (d, J=9.6 Hz, 2H), 7.20 (br s, 1H), 7.37 (br s, 1H), 10.51 (br s, 1H), 10.93 (s, 1H), 11.58 (s, 1H) ppm; $^{13}$C NMR (CDCl$_3$, 100 MHz) δ 14.01, 14.01, 33.92, 34.17, 62.05, 62.09, 108.68, 111.90, 113.64, 114.13, 116.27, 116.27, 116.47, 116.80, 116.93, 118.74, 121.32, 122.17, 124.17, 124.62, 130.62, 133.37, 147.17, 148.83, 161.82, 162.94, 168.61, 168.70, 185.14, 186.83 ppm; HRMS ESI (M+$^H$) calculated for $C_{30}H_{25}Cl_4N_2O_8S_2$ 744.9806. found 744.9812; IR (KBr) 3671, 3368, 3080, 2960, 2920, 1919, 1735, 1618, 1585, 1439, 1216, 1145, 1030, 745, 703 cm$^{-1}$. HPLC purity, 96.8% (Flow rate: 1.0 mL/min; Column: Agilent ZORBAX 300SB-C8, 5 μm, 150×4.6 mm; Wavelength: UV 254 nm; Temperature: 25° C.; Mobile phase: MeOH:$H_2O$=90:10; $t_R$=20.0 min).

(4,4',5,5'-Tetrachloro-1'H-1,3'-bipyrrole-2,2'-diyl)bis (((2-hydroxy-4-benzylthio)phenyl)methanone) (1-10)

Under $N_2$, a mixture of 14 (Cheng C, et al. *Mar. Drugs.* 2013, 11, 2927-2948) (50 mg, 0.06 mmol), phenylmethanethiol (32 mg, 0.24 mmol), Pd$_2$(dba)$_3$ (2 mg, 0.003 mmol), Xantphos (4 mg, 0.006 mmol) and i-Pr$_2$NEt (31 mg, 0.24 mmol) was dissolved in 1,4-dioxane (5 mL). The reaction was heated to reflux and stirred for about 4 h. The reaction was quenched with water (10 mL) and extracted with EtOAc (15 mL×3). The combined organic layers were dried over anhydrous sodium sulfate, filtered and concentrated in vacuum. The residue was purified by flash column chromatography (15% EtOAc/petroleum ether, $R_f$=0.3) to yield 1-10 (45 mg, 96%) as a yellow solid: melting point 82.4-83.7° C.; $^1$H NMR (400 MHz, CDCl$_3$) δ 4.17 (s, 2H), 4.22 (s, 2H), 6.11 (s, 1H), 6.47 (d, J=8.4 Hz, 1H), 6.61 (br, s, 1H), 6.74 (s, 1H), 6.80 (s, 1H), 7.27-7.41 (m, 12H), 9.90 (br s, 1H), 10.95 (s, 1H), 11.63 (s, 1H) ppm; $^{13}$C NMR (CDCl$_3$, 100 MHz) δ 36.24, 36.43, 108.77, 111.98, 113.35, 113.85, 115.84, 116.15, 116.26, 116.79, 117.01, 121.27, 122.15, 124.21, 124.72, 127.65, 127.65, 127.68, 127.68, 128.68, 128.68, 128.68, 128.78, 128.78, 128.78, 128.78, 130.46, 133.14, 135.34, 135.49, 149.49, 151.08, 161.84, 163.04, 185.08, 186.71 ppm; HRMS ESI (M+H$^+$) calculated for $C_{36}H_{25}Cl_4N_2O_4S_2$ 753.0010. found 753.0005; IR (KBr) 3410, 3236, 3061, 3028, 2923, 1616, 1581, 1483, 1448, 1391, 1327, 1223, 1073, 928, 780 cm$^{-1}$. HPLC purity, 96.9% (Flow rate: 1.0 mL/min; Column: Agilent ZORBAX 300SB-C8, 5 μm, 150×4.6 mm; Wavelength: UV 254 nm; Temperature: 25° C.; Mobile phase: MeOH:$H_2O$=95:5; $t_R$=6.6 min).

(4,4',5,5'-Tetrachloro-1'H-1,3'-bipyrrole-2,2'-diyl)bis (((2-hydroxy-4-(4-methoxybenzylthio)phenyl) methanone) (1-11)

Under $N_2$, a mixture of 14 (Cheng C, et al. *Mar. Drugs.* 2013, 11, 2927-2948) (20 mg, 0.02 mmol), (4-methoxyphenyl) methanethiol (15 mg, 0.10 mmol), Pd$_2$(dba)$_3$ (0.8 mg, 0.001 mmol), Xantphos (1.6 mg, 0.002 mmol) and i-Pr$_2$NEt (12 mg, 0.10 mmol) was dissolved in 1,4-dioxane (3 mL). The reaction was heated to reflux and stirred for about 4 h. The reaction was quenched with water (10 mL) and extracted with EtOAc (10 mL×3). The combined organic layers were dried over anhydrous sodium sulfate, filtered and concentrated in vacuum. The residue was purified by flash column chromatography (20% EtOAc/petroleum ether, R$_f$=0.3) to yield 1-11 (17 mg, 85%) as a yellow solid: melting point 85.4-86.7° C.; $^1$H NMR (400 MHz, CDCl$_3$) δ 3.78 (s, 3H), 3.79 (s, 3H), 4.13 (s, 2H), 4.18 (s, 2H), 6.11 (s, 1H), 6.46 (d, J=8.4 Hz, 1H), 6.62 (s, 1H), 6.74 (s, 1H), 6.80 (s, 1H), 6.86 (dd, J=8.4, 3.2 Hz, 5H), 7.31 (t, J=8.4 Hz, 5H), 9.71 (br s, 1H), 10.99 (s, 1H), 11.64 (s, 1H) ppm; $^{13}$C NMR (CDCl$_3$, 100 MHz) δ 35.72, 35.90, 53.66, 55.25, 108.83, 111.94, 113.30, 113.83, 114.18, 114.18, 114.18, 114.18, 114.18, 115.78, 116.11, 116.24, 116.72, 117.01, 121.23, 121.96, 124.08, 124.77, 127.11, 127.29, 129.85, 129.85, 129.96, 129.96, 130.40, 133.12, 149.68, 151.31, 159.01, 159.06, 161.90, 163.05, 185.02, 186.71 ppm; HRMS ESI (M+H$^+$) calculated for C$_{38}$H$_{29}$Cl$_4$N$_2$O$_6$S$_2$ 813.0221. found 813.0228; IR (KBr) 3421, 3253, 2929, 2836, 1702, 1615, 1511, 1447, 1393, 1329, 1248, 1177, 1075, 1034, 943 cm$^{-1}$. HPLC purity, 96.5% (Flow rate: 1.0 mL/min; Column: Agilent ZORBAX 300SB-C8, 5 μm, 150×4.6 mm; Wavelength: UV 254 nm; Temperature: 25° C.; Mobile phase: MeOH:H$_2$O=95:5; t$_R$=6.4 min).

(4,4',5,5'-Tetrachloro-1'H-1,3'-bipyrrole-2,2'-diyl)bis (((2-hydroxy-4-(3-ethylacetate)sulfonylphenyl) methanone) (1-12)

To a solution of 1-9 (22 mg, 0.03 mmol) in CH$_2$Cl$_2$ (2 mL), a solution of m-CPBA (31 mg, 0.18 mmol) in CH$_2$Cl$_2$ (1 mL) was added at room temperature. After being stirred for about 20 h, the reaction was quenched by addition water (10 mL) and extracted with CH$_2$Cl$_2$ (10 mL×3). The combined organic layers were dried over anhydrous sodium sulfate, filtered and concentrated in vacuum. The residue was purified by flash column chromatography (20% acetone, 27% EtOAc, 53% petroleum ether, R$_f$=0.2) to yield 1-12 (16.7 mg, 70%) as a yellow solid: melting point 90.0-91.7° C.; $^1$H NMR (400 MHz, acetone-d$_6$) δ 1.16-1.18 (m, 6H), 4.09-4.14 (m, 4H), 4.33 (s, 2H), 4.42 (s, 2H), 6.48 (s, 1H), 7.32 (d, J=8.0 Hz, 1H), 7.45-7.52 (m, 3H), 7.61 (d, J=8.0 Hz, 1H), 7.23 (d, J=8.0 Hz, 1H), 10.48 (br s, 2H), 12.33 (br s, 1H) ppm; $^{13}$C NMR (acetone-d$_6$, 100 MHz) δ 14.14, 14.14, 60.98, 61.02, 62.58, 62.58, 110.42, 112.21, 117.11, 117.38, 118.94, 119.29, 119.65, 122.89, 124.02, 126.06, 127.21, 128.65, 128.75, 129.08, 131.08, 132.87, 144.04, 144.64, 157.98, 158.59, 163.00, 163.05, 183.41, 184.48 ppm; HRMS ESI (M+H$^+$) calculated for C$_{30}$H$_{25}$Cl$_4$N$_2$O$_{12}$S$_2$ 808.9603. found 808.9599; IR (KBr) 2918, 2850, 2490, 1741, 1637, 1589, 1441, 1407, 1330, 1269, 1215, 1151, 1029, 751, 703, 637 cm$^{-1}$. HPLC purity, 98.1% (Flow rate: 1.0 mL/min; Column: Waters C18, 5 μm, 150×4.6 mm; Wavelength: UV 254 nm; Temperature: 25° C.; Mobile phase: MeOH:H$_2$O=70:30; t$_R$=30.4 min).

(4,4',5,5'-Tetrachloro-1'H-1,3'-bipyrrole-2,2'-diyl)bis (((2-hydroxy-4-benzylsulfonyl)phenyl)methanone) (1-13)

To a solution of 1-10 (30 mg, 0.04 mmol) in CH$_2$Cl$_2$ (2 mL), a solution of m-CPBA (42 mg, 0.24 mmol) in CH$_2$Cl$_2$ (1 mL) was added at room temperature. After being stirred for about 5 h, the reaction was quenched by addition water (10 mL) and extracted with CH$_2$Cl$_2$ (10 mL×3). The combined organic layers were dried over anhydrous sodium sulfate, filtered and concentrated in vacuum. The residue was purified by flash column chromatography (20% acetone, 27% EtOAc, 53% petroleum ether, R$_f$=0.2) to yield 1-13 (24 mg, 75%) as a yellow solid: melting point 130.9-132.7° C.; $^1$H NMR (400 MHz, CDCl$_3$) δ 4.26 (s, 2H), 4.34 (s, 2H), 6.12 (s, 1H), 6.99 (d, J=8.4 Hz, 1H), 7.05 (d, J=8.4 Hz, 1H), 7.14-7.17 (m, 4H), 7.29-7.37 (m, 8H), 7.58 (d, J=8.4 Hz, 1H), 7.68 (d, J=8.0 Hz, 1H) ppm; $^{13}$C NMR (CDCl$_3$, 100 MHz) δ 62.17, 62.35, 110.30, 110.34, 112.10, 117.23, 117.51, 118.83, 119.18, 119.80, 124.03, 126.02, 127.12, 127.83, 128.40, 128.75, 129.07, 129.15, 129.15, 129.19, 129.19, 129.34, 129.40, 129.45, 131.25, 131.88, 131.88, 131.88, 131.98, 131.98, 132.82, 144.07, 144.21, 158.24, 183.74, 184.70 ppm; HRMS ESI (M+H$^+$) calculated for C$_{36}$H$_{25}$Cl$_4$N$_2$O$_8$S$_2$ 816.9806. found 816.9800; IR (KBr) 3078, 3030, 2959, 2920, 2851, 2583, 1730, 1636, 1591, 1142, 1407, 1319, 1149, 1125, 879, 750, 701, 628 cm$^{-1}$. HPLC purity, 97.1% (Flow rate: 1.0 mL/min; Column: Agilent ZORBAX 300SB-C8, 5 m, 150×4.6 mm; Wavelength: UV 254 nm; Temperature: 25° C.; Mobile phase: MeOH:H$_2$O=60:40; t$_R$=11.9 min).

(4,4',5,5'-Tetrachloro-1'H-1,3'-bipyrrole-2,2'-diyl)bis (((2-hydroxy-4-(4-methoxybenzylsulfonyl)phenyl) methanone) (1-14)

To a solution of 1-11 (60 mg, 0.07 mmol) in CH$_2$Cl$_2$ (5 mL), a solution of m-CPBA (128 mg, 0.74 mmol) in CH$_2$Cl$_2$ (2 mL) was added at room temperature. After being stirred for about 20 h, the reaction was quenched by adding water (10 mL) and extracted with CH$_2$Cl$_2$ (10 mL×3). The combined organic layers were dried over anhydrous sodium sulfate, filtered and concentrated in vacuum. The residue was purified by flash column chromatography (20% acetone, 27% EtOAc, 53% petroleum ether, R$_f$=0.2) to yield 1-14 (42 mg, 65%) as a yellow solid: melting point 104.3-106.3° C.; $^1$H NMR (400 MHz, CDCl$_3$) δ 3.77 (s, 6H), 4.20 (s, 2H), 4.31 (s, 2H), 6.17 (s, 1H), 6.80 (t, J=7.2 Hz, 4H), 6.97 (d, J=8.4 Hz, 1H), 7.05 (d, J=8.4 Hz, 5H), 7.16 (s, 1H), 7.36 (s, 1H), 7.62 (d, J=8.4 Hz, 1H), 7.67 (d, J=8.0 Hz, 1H), 10.44 (br s, 1H), 11.00 (br s, 1H) ppm; $^{13}$C NMR (CDCl$_3$, 100 MHz) δ 55.26, 55.26, 61.84, 61.84, 109.45, 112.63, 114.18, 114.18, 114.18, 114.22, 114.22, 117.59, 118.33, 118.57, 118.57, 118.82, 118.93, 122.16, 122.80, 123.45, 124.62, 125.25, 126.44, 131.09, 132.02, 132.02, 132.02, 132.09, 132.09, 133.78, 143.91, 144.84, 160.15, 160.22, 160.63, 161.77, 184.85, 187.06 ppm; HRMS ESI (M+Na$^+$) calculated for C$_{38}$H$_{28}$Cl$_4$N$_2$NaO$_{10}$S$_2$ 898.9837. found 898.9838; IR (KBr) 2961, 2920, 2850, 1730, 1632, 1592, 1512, 1444, 1257, 1148, 1099, 1030, 798 cm$^{-1}$. HPLC purity, 95.1% (Flow rate: 1.0 mL/min; Column: Agilent ZORBAX 300SB-C8, 5 μm, 150×4.6 mm; Wavelength: UV 254 nm; Temperature: 25° C.; Mobile phase: MeOH:H$_2$O=65:35; t$_R$=6.0 min).

(4,4',5,5'-Tetrachloro-1'H-1,3'-bipyrrole-2,2'-diyl)bis (((2-hydroxy-4-(p-acetic acid)thiophenyl)methanone) (1-15)

To a solution of 1-9 (20 mg, 0.03 mmol) in a mixture of H$_2$O/THF (1:2, 3 mL), LiOH (15 mg, 0.35 mmol) was added at room temperature. The reaction was allowed to warm up to 50° C. and stirred for about 10 h. The reaction was adjusted to pH 5.0 with 0.5 N HCl and extracted with EtOAc (5 mL×3). The combined organic layers were dried over anhydrous sodium sulfate, filtered and concentrated in vacuum. The residue was purified by reverse-phase column chromatography (C18 reverse silica gel, 7% AcOH, 22% $H_2O$, 71% MeOH, $R_f$=0.2) to yield 1-15 (15.7 mg, 85%) as a brown solid: melting point 137.9-139.7° C.; $^1$H NMR (400 MHz, DMSO-$d_6$) δ 3.46 (s, 2H), 3.65 (s, 2H), 6.03 (s, 1H), 6.53-6.60 (m, 3H), 6.64 (s, 1H), 7.38 (d, J=7.6 Hz, 1H), 7.85 (d, J=8.0 Hz, 1H) ppm; $^{13}$C NMR (DMSO-$d_6$, 100 MHz) δ 36.10, 36.80, 108.30, 109.39, 112.71, 112.94, 115.56, 116.02, 116.84, 118.22, 120.95, 122.60, 123.09, 124.39, 128.56, 131.13, 132.65, 133.61, 144.10, 149.87, 159.26, 160.70, 171.50, 172.90, 181.57, 186.55 ppm; HRMS ESI (M+Na$^+$) calculated for $C_{26}H_{16}Cl_4N_2NaO_8S_2$ 710.9000. found 710.9009; IR (KBr) 3392, 2955, 2918, 2849, 1592, 1382, 1223, 1023, 671 cm$^{-1}$. HPLC purity, 98.7% (Flow rate: 1.0 mL/min; Column: Agilent ZORBAX 300SB-C8, 5 m, 150×4.6 mm; Wavelength: UV 254 nm; Temperature: 25° C.; Mobile phase: MeOH:$H_2O$=60:40; $t_R$=8.0 min).

(4,4',5,5'-Tetrachloro-1'H-1,3'-bipyrrole-2,2'-diyl)bis(((2-hydroxy-4-(p-acetic acid)sulfonylphenyl)methanone) (1-16)

To a solution of 1-12 (70 mg, 0.09 mmol) in a mixture of $H_2O$/THF (1:2, 5 mL), LiOH (49 mg, 1.13 mmol) was added at room temperature. The reaction was allowed to warm up to 50° C. and stir for about 3 h. The reaction was adjusted to pH 5.0 with 0.5 N HCl and extracted with EtOAc (10 mL×3). The combined organic layers were dried over anhydrous sodium sulfate, filtered and concentrated in vacuum. The residue was purified by reverse column chromatography (C18 reverse silica gel, 4% AcOH, 38% $H_2O$, 58% MeOH, $R_f$=0.2) to yield 1-16 (62 mg, 95%) as a yellow solid: melting point 143.2-144.7° C.; $^1$H NMR (400 MHz, DMSO-$d_6$) δ 4.12 (s, 2H), 4.18 (s, 2H), 6.22 (s, 1H), 7.15 (d, J=8.0 Hz, 1H), 7.27-7.29 (m, 4H), 7.36-7.40 (m, 1H) ppm; $^{13}$C NMR (acetone-$d_6$, 100 MHz) δ 52.09, 52.09, 100.10, 100.18, 100.98, 105.79, 107.20, 108.26, 108.65, 112.73, 113.40, 115.44, 118.90, 118.91, 120.25, 120.40, 120.53, 121.64, 133.09, 146.18, 146.89, 154.58, 163.09, 163.09, 171.58, 172.34 ppm; HRMS ESI (M+H$^+$) calculated for $C_{26}H_{17}Cl_4N_2O_{12}S_2$ 752.8977. found 752.8981; IR (KBr) 3395, 2957, 2923, 1628, 1445, 1407, 1313, 1147, 1026, 1000, 906, 825, 701 cm$^{-1}$. HPLC purity, 95.2% (Flow rate: 1.0 mL/min; Column: Agilent ZORBAX 300SB-C8, 5 μm, 150×4.6 mm; Wavelength: UV 254 nm; Temperature: 25° C.; Mobile phase: MeOH:$H_2O$=60:40; $t_R$=4.0 min).

(1'-Tosyl-1'H-1,3'-bipyrrole-2,2'-diyl)bis((2-methoxy-4-((trimethylsilyl)ethynyl)phenyl)methanone) (16)

Under $N_2$, a mixture of 15 (Cheng C, et al. Mar. Drugs. 2013, 11, 2927-2948) (50 mg, 0.06 mmol), ethynyltrimethylsilane (34 mg, 0.35 mmol), Pd(PPh$_3$)$_4$ (15 mg, 0.01 mmol) and Et$_3$N (18 mg, 0.18 mmol) was dissolved in anhydrous DMF (5 mL). The reaction was heated to 60° C. and stirred for 10 h. The reaction was quenched with water (10 mL) and extracted with EtOAc (15 mL×3). The combined organic layers were dried over anhydrous sodium sulfate, filtered and concentrated in vacuum. The residue was purified by column chromatography (10% EtOAc/petroleum, $R_f$=0.3) to yield 16 (40 mg, 92% yield) as a brown solid: melting point 105.3-106.7° C.; $^1$H NMR (400 MHz, CDCl$_3$) δ 0.07 (s, 6H), 0.26 (s, 6H), 0.27 (s, 6H), 2.44 (s, 3H), 3.65 (s, 3H), 3.77 (s, 3H), 5.90 (t, J=2.8 Hz, 1H), 6.29 (dd, J=4.0, 1.2 Hz, 1H), 6.44 (d, J=3.2 Hz, 1H), 6.71 (br s, 2H), 6.79 (d, J=7.6 Hz, 1H), 6.96 (d, J=8.0 Hz, 1H), 6.99 (s, 1H), 7.04 (d, J=7.6 Hz, 1H), 7.21 (d, J=7.6 Hz, 1H), 7.35 (d, J=8.0 Hz, 2H), 7.56 (d, J=3.2 Hz, 1H), 7.94 (d, J=8.4 Hz, 2H) ppm; $^{13}$C NMR (CDCl$_3$, 100 MHz) δ −0.13, −0.13, −0.13, −0.13, −0.13, −0.13, −21.71, 55.67, 55.67, 95.75, 96.80, 104.23, 104.31, 109.13, 111.89, 114.16, 114.39, 123.46, 123.55, 123.55, 124.47, 125.81, 127.61, 127.65, 128.31, 128.31, 128.52, 129.06, 129.63, 129.63, 129.90, 130.86, 131.92, 132.76, 133.02, 135.74, 145.16, 156.89, 157.58, 182.54, 184.05 ppm; HRMS ESI (M+H$^+$) calculated for $C_{41}H_{43}N_2O_6SSi_2$ 747.2380. found 747.2382; IR (KBr) 3443, 3145, 2959, 2857, 2158, 1649, 1600, 1556, 1405, 1377, 1272, 1253, 1175, 1135, 1034, 952, 852, 667 cm$^{-1}$.

1'H-1,3'-Bipyrrole-2,2'-diylbis((4-ethynyl-2-methoxyphenyl)methanone) (17)

To a solution of 16 (300 mg, 0.40 mmol) in a mixture of MeOH/THF (1:1, 10 mL), KOH (113 mg, 2.0 mmol) was added at room temperature. After being stirred for 2 h, the reaction was adjusted to pH 7.0 with 0.5 N HCl and extracted with EtOAc (10 mL×3). The combined organic layers were dried over anhydrous sodium sulfate, filtered and concentrated in vacuum. The residue was purified by column chromatography (33% EtOAc/petroleum ether, $R_f$=0.3) to yield 17 (171 mg, 95% yield) as a brown solid: melting point 178.7-180.0° C.; $^1$H NMR (400 MHz, CDCl$_3$) δ 3.10 (s, 1H), 3.15 (s, 1H), 3.69 (s, 3H), 3.79 (s, 3H), 5.88 (dd, J=4.0, 2.4 Hz, 1H), 6.31 (t, J=2.4 Hz, 1H), 6.36 (dd, J=4.0, 1.6 Hz, 1H), 6.64 (t, J=2.0 Hz, 1H), 6.78 (s, 1H), 6.79 (d, J=7.6 Hz, 1H), 7.04 (s, 1H), 7.08 (t, J=2.8 Hz, 1H), 7.10-7.12 (m, 3H), 9.43 (br s, 1H) ppm; $^{13}$C NMR (DMSO-$d_6$+acetone-$d_6$, 100 MHz) δ 55.39, 55.65, 80.75, 80.98, 83.21, 83.38, 108.79, 109.96, 114.08, 114.94, 122.74, 123.51, 123.68, 123.76, 124.20, 124.45, 126.25, 128.65, 129.17, 129.75, 130.70, 131.13, 132.10, 133.06, 156.16, 156.69, 181.92, 182.70 ppm; HRMS ESI (M+H$^+$) calculated for $C_{28}H_{21}N_2O_4$ 449.1501. found 449.1494; IR (KBr) 3339, 3281, 3259, 3130, 2942, 2855, 1645, 1612, 1559, 1494, 1409, 1263, 1121, 938, 749 cm$^{-1}$.

Diethyl 2,2'-(4,4'-((1'H-1,3'-bipyrrole-2,2'-dicarbonyl)bis(3-methoxy-4,1-phenylene))bis(1H-1,2,3-triazole-4,1-diyl))diacetate (18)

Under $N_2$, a mixture of 17 (50 mg, 0.11 mmol), ethyl 2-azidoacetate (58 mg, 0.44 mmol), and CuCl (10 mg, 0.11 mmol) was dissolved in THF (5 mL). The reaction was allowed to warm up to reflux and stirred for about 10 h. The suspension was filtered and the filtrate was concentrated in vacuum. The residue was purified by column chromatography (33% EtOAc/petroleum ether, $R_f$=0.3) to yield 18 (61 mg, 78% yield) as a light yellow solid: melting point 136.3-137.7° C.; $^1$H NMR (400 MHz, CDCl$_3$) δ 1.31-1.41 (m, 6H), 3.78 (s, 3H), 3.87 (s, 3H), 4.27-4.33 (m, 4H), 5.22 (s, 4H), 5.87 (dd, J=4.0, 2.8 Hz, 1H), 6.33 (t, J=2.4 Hz, 1H), 6.36 (dd, J=4.0, 1.6 Hz, 1H), 6.71 (t, J=2.4 Hz, 1H), 7.01 (d, J=7.6 Hz, 1H), 7.07 (t, J=3.2 Hz, 1H), 7.17 (d, J=7.6 Hz, 1H), 7.22-7.24 (m, 2H), 7.36 (s, 1H), 7.55 (s, 1H), 7.89 (s, 1H), 8.00 (s, 1H), 9.45 (br s, 1H) ppm; $^{13}$C NMR (DMSO-$d_6$+CD$_3$OD, 100 MHz) δ 14.51, 14.59, 51.80, 51.80, 56.04, 56.28, 63.15, 63.15, 108.73, 109.47, 110.08, 111.05, 117.76, 118.22, 124.40, 124.50, 124.55, 124.59, 127.38, 129.49, 130.13, 130.54, 131.28, 132.62, 133.40, 134.38, 134.48, 134.55, 147.93, 158.25, 158.82, 168.38, 168.43, 184.34, 184.86 ppm; HRMS ESI (M+H$^+$) calculated for $C_{36}H_{35}N_8O_8$ 707.2578. found 707.2588; IR (KBr) 3420, 3265, 3139, 2986, 2942, 2852, 1745, 1634, 1614, 1562, 1412, 1247, 1226, 1132, 1028, 932, 783 cm$^{-1}$.

Diethyl 2,2'-(4,4'-((4,4',5,5'-tetrachloro-1'H-1,3'-bipyrrole-2,2'-dicarbonyl)bis(2-chloro-5-methoxy-4,1-phenylene))bis(1H-1,2,3-triazole-4,1-diyl))diacetate (19)

To a solution of 18 (40 mg, 0.06 mmol) in AcOH (3 mL) at room temperature, NCS (54 mg, 0.40 mmol) was added slowly. The reaction was allowed to stir for about 8 h at room temperature. The reaction was quenched with water (15 mL) and extracted with EtOAc (10 mL×3). The combined organic layers were dried over anhydrous sodium sulfate, filtered and concentrated in vacuum. The residue was purified by column chromatography (25% EtOAc/petroleum ether, $R_f$=0.2) to yield 19 (5 mg, 10% yield) as a brown solid: melting point 118.7-120.3° C.; $^1$H NMR (400 MHz, CDCl$_3$) δ 1.28-1.36 (m, 6H), 3.84 (s, 3H), 3.87 (s, 3H), 4.25-4.33 (m, 4H), 5.23 (s, 2H), 5.27 (s, 2H), 6.49 (s, 1H), 7.23 (s, 1H), 7.36 (s, 1H), 7.79 (s, 1H), 7.90 (s, 1H), 8.36 (s, 1H), 8.45 (s, 1H), 10.86 (br s, 1H) ppm; $^{13}$C NMR (CDCl$_3$, 100 MHz) δ 29.59, 29.63, 50.94, 51.00, 56.11, 56.14, 62.52, 62.58, 111.11, 111.44, 112.20, 112.31, 120.78, 121.14, 121.59, 121.82, 124.20, 125.09, 125.19, 125.24, 125.28, 126.76, 128.03, 129.63, 130.51, 131.09, 131.71, 131.93, 143.50, 143.66, 155.59, 156.17, 166.04, 166.10, 180.07, 180.49 ppm; HRMS ESI (M+H$^+$) calculated for $C_{36}H_{29}Cl_6N_8O$, 911.0240. found 911.0265; IR (KBr) 3419, 3162, 2925, 2852, 1750, 1645, 1607, 1463, 1396, 1254, 1218, 1022, 915 cm$^{-1}$.

Diethyl 2,2'-(4,4'-((4,4',5,5'-tetrachloro-1'H-1,3'-bipyrrole-2,2'-dicarbonyl)bis(2-chloro-5-hydroxy-4,1-phenylene))bis(1H-1,2,3-triazole-4,1-diyl))diacetate (1-17)

To a solution of 19 (40 mg, 0.04 mmol) in anhydrous CH$_2$Cl$_2$ (5 mL), a solution of BBr$_3$ (44 mg, 0.16 mmol) in anhydrous CH$_2$Cl$_2$ (1 mL) was slowly added via a syringe under N$_2$ at −78° C. After being stirred for 2 h, the reaction was quenched by addition of water (10 mL) and extracted with CH$_2$Cl$_2$ (10 mL×3). The combined organic layers were dried over anhydrous sodium sulfate, filtered and concentrated in vacuum. The residue was purified by column chromatography (30% EtOAc/petroleum ether, $R_f$=0.2) to yield 1-17 (19 mg, 50% yield) as a brown solid: melting point 157.3-169.7° C.; $^1$H NMR (400 MHz, CDCl$_3$) δ 1.29-1.35 (m, 6H), 4.25-4.34 (m, 4H), 5.21 (s, 2H), 5.25 (s, 2H), 6.81 (s, 1H), 7.65 (br s, 2H), 7.92 (s, 1H), 7.98 (s, 1H), 8.37 (s, 1H), 8.46 (s, 1H), 10.91 (br s, 1H) ppm; $^{13}$C NMR (acetone-d$_6$, 100 MHz) δ 14.31, 14.31, 51.39, 51.49, 62.40, 62.46, 109.10, 111.18, 118.09, 118.25, 118.87, 118.95, 119.75, 120.46, 120.93, 121.53, 123.79, 126.17, 126.71, 126.92, 127.51, 131.06, 134.03, 134.39, 134.61, 136.25, 143.15, 143.78, 158.99, 160.48, 167.59, 167.67, 181.63, 186.11 ppm; HRMS ESI (M+H$^+$) calculated for $C_{34}H_{25}Cl_6N_8O_8$ 882.9927. found 882.9933; IR (KBr) 3446, 2955, 2923, 2850, 1749, 1627, 1458, 1377, 1218, 1020, 919, 775 cm$^{-1}$. HPLC purity, 95.2% (Flow rate: 1.0 mL/min; Column: Phenomenex C6-phenyl, 5 μm, 150×4.6 mm; Wavelength: UV 254 nm; Temperature: 25° C.; Mobile phase: MeOH:H$_2$O=80:20; $t_R$=10.8 min).

(1'-Tosyl-1'H-1,3'-bipyrrole-2,2'-dicarbonyl)bis(3-hydroxy-4,1-phenylene)bis(trifluoromethanesulfonate) (20)

To a solution of 15 (Cheng C, et al. Mar. Drugs. 2013, 11, 2927-2948) (2.5 g, 2.94 mmol) in anhydrous CH$_2$Cl$_2$ (100 mL), a solution of BBr$_3$ (3.68 g, 14.70 mmol) in anhydrous CH$_2$Cl$_2$ (5 mL) was slowly added via a syringe under N$_2$ at −78° C. After being stirred for 0.5 h, the reaction was quenched by addition of water (100 mL) and extracted with CH$_2$Cl$_2$ (50 mL×3). The combined organic layers were dried over anhydrous sodium sulfate, filtered and concentrated in vacuum. The residue was purified by column chromatography (12% EtOAc/petroleum ether, $R_f$=0.3) to yield 20 (2.17 g, 90% yield) as a yellow oil: $^1$H NMR (400 MHz, CDCl$_3$) δ 2.48 (s, 3H), 6.15 (t, J=2.8 Hz, 1H), 6.40 (d, J=3.6 Hz, 1H), 6.45 (dd, J=8.8, 2.4 Hz, 1H), 6.70 (d, J=3.6 Hz, 1H), 6.75 (d, J=2.4 Hz, 1H), 6.78 (dd, J=8.8, 2.4 Hz, 1H), 6.84 (s, 1H), 6.91 (d, J=2.0 Hz, 1H), 7.39 (d, J=8.0 Hz, 2H), 7.56 (s, 1H), 7.57 (d, J=5.2 Hz, 1H), 7.68 (d, J=8.8 Hz, 1H), 7.89 (d, J=8.4 Hz, 2H), 11.48 (s, 1H), 11.83 (s, 1H) ppm; $^{13}$C NMR (CDCl$_3$, 100 MHz) δ 21.70, 110.72, 110.72, 111.03, 111.09, 111.72, 112.06, 119.24, 119.59, 123.57, 123.57, 125.45, 128.16, 128.16, 128.40, 129.93, 129.93, 130.00, 131.77, 131.85, 133.88, 133.88, 134.48, 135.00, 146.15, 153.58, 153.98, 163.57, 164.06, 186.46, 189.44 ppm. HRMS ESI (M+H$^+$) calculated for $C_{31}H_{21}F_6N_2O_{12}S_3$ 823.0161. found 823.0173. IR (KBr) 3159, 2943, 1685, 1671, 1550, 1454, 1368, 1272, 1137, 1027, 899 cm$^{-1}$.

(1'-Tosyl-1'H-1,3'-bipyrrole-2,2'-diyl)bis((2-hydroxy-4-((trimethylsilyl)ethynyl)phenyl)methanone) (21)

Under N$_2$, a mixture of 20 (100 mg, 0.12 mmol), ethynyltrimethylsilane (72 mg, 0.73 mmol), Pd(PPh$_3$)$_4$ (30 mg, 0.02 mmol) and Et$_3$N (37 mg, 0.36 mmol) was dissolved in anhydrous DMF (5 mL). The reaction was allowed to warm up 15 to 70° C. and stirred for about 10 h. The reaction was quenched with water (10 mL) and extracted with EtOAc (10 mL×3). The combined organic layers were dried over anhydrous sodium sulfate, filtered and concentrated in vacuum. The residue was purified by column chromatography (10% EtOAc/petroleum ether, $R_f$=0.3) to yield 21 (85 mg, 98% yield) as a pale yellow oil: $^1$H NMR (400 MHz, CDCl$_3$) δ 0.23 (s, 9H), 0.26 (s, 9H), 2.45 (s, 3H), 6.09 (t, J=2.8 Hz, 1H), 6.39 (d, J=3.2 Hz, 1H), 6.56 (d, J=8.0 Hz, 1H), 6.65 (d, J=3.2 Hz, 1H), 6.77 (s, 1H), 6.90 (s, 1H), 6.92 (d, J=8.8 Hz, 1H), 7.06 (s, 1H), 7.34-7.38 (m, 3H), 7.48 (d, J=3.6 Hz, 1H), 7.53 (d, J=8.4 Hz, 1H), 7.86 (d, J=8.0 Hz, 2H), 11.34 (s, 1H), 11.55 (s, 1H) ppm; $^{13}$C NMR (CDCl$_3$, 100 MHz) δ −0.26, −0.26, −0.26, −0.21, −0.21, −0.21, 21.76, 98.47, 99.46, 103.56, 103.78, 110.47, 110.95, 119.48, 119.66, 120.61, 121.14, 122.07, 122.55, 123.15, 123.92, 124.19, 128.14, 128.14, 129.86, 129.86, 130.08, 130.35, 131.10, 131.40, 131.48, 131.98, 132.49, 135.18, 145.91, 161.91, 162.05, 187.11, 190.31 ppm; HRMS ESI (M+H$^+$) calculated for $C_{39}H_{39}N_2O_6SSi_2$ 719.2067. found 719.2062. IR (KBr) 3159, 2997, 2973, 1795, 1681, 1580, 1417, 1272, 1167, 1097, 878 cm$^{-1}$.

1'H-1,3'-Bipyrrole-2,2'-diylbis((4-ethynyl-2-hydroxyphenyl)methanone) (22)

To a solution of 21 (85 mg, 0.12 mmol) in a mixture of MeOH/THF (1:1, 5 mL), KOH (33 mg, 0.59 mmol) was added at room temperature. After being stirred for 1.5 h, the reaction was adjusted to pH 7.0 with 0.5 N HCl and extracted with EtOAc (10 mL×3). The combined organic layers were dried over anhydrous sodium sulfate, filtered and concentrated in vacuum. The residue was purified by column chromatography (33% EtOAc/petroleum ether, $R_f$=0.3) to yield 22 (47 mg, 95% yield) as a yellow oil: $^1$H NMR (400 MHz, CDCl$_3$) δ 3.20 (s, 1H), 3.24 (s, 1H), 6.23 (t, J=3.2 Hz, 1H), 6.36 (s, 1H), 6.55 (d, J=8.0 Hz, 1H), 6.72 (d, J=3.2 Hz, 1H), 6.90 (d, J=6.8 Hz, 1H), 6.93 (d, J=4.0 Hz, 2H), 7.07 (s, 1H), 7.14 (t, J=2.8 Hz, 1H), 7.22 (d, J=8.0 Hz, 1H), 7.32 (d, J=8.0 Hz, 1H), 9.48 (br s, 1H), 10.97 (s, 1H), 11.48 (s, 1H) ppm; $^{13}$C NMR (acetone-d$_6$, 100 MHz) δ 82.18, 82.40, 83.10, 109.73, 109.79, 110.96, 120.91, 121.00, 121.06, 121.15, 121.24, 122.49, 122.57, 123.83, 124.92, 125.09, 128.81, 129.37, 131.01, 131.37, 133.14, 161.25, 162.14, 162.42, 187.26, 187.82 ppm; HRMS ESI (M+Na$^+$) calculated for C$_{26}$H$_{16}$N$_2$NaO$_4$ 443.1008. found 443.1003. IR (KBr) 3435, 3239, 2980, 1785, 1691, 1590, 1424, 1127, 1017, 886 cm$^{-1}$.

Di-tert-butyl 2,2'-(4,4'-((1'H-1,3'-bipyrrole-2,2'-dicarbonyl)bis(3-hydroxy-4,1-phenylene))bis(1H-1,2,3-triazole-4,1-diyl))diacetate (23)

Under N$_2$, a mixture of 22 (200 mg, 0.48 mmol), tert-butyl 2-azidoacetate (300 mg, 1.90 mmol), and CuCl (47 mg, 0.48 mmol) was dissolved in THF (5 mL). The reaction was allowed to warm up to reflux and stirred for about 8 h. The suspension was filtered and the filtrate was concentrated in vacuum. The residue was purified by column chromatography (40% EtOAc/petroleum ether, R$_f$=0.3) to yield 23 (280 mg, 80% yield) as a yellow solid: melting point 96.0-97.0° C.; $^1$H NMR (400 MHz, acetone-d$_6$) δ 1.48 (s, 9H), 1.49 (s, 9H), 5.31 (s, 2H), 5.33 (s, 2H), 6.28 (dd, J=3.6, 2.8 Hz, 1H), 6.44 (t, J=2.4 Hz, 1H), 6.77 (dd, J=4.0, 1.6 Hz, 1H), 7.10 (dd, J=8.4, 1.6 Hz, 1H), 7.26-7.32 (m, 4H), 7.44 (d, J=1.6 Hz, 1H), 7.48-7.51 (m, 2H), 8.49 (s, 1H), 8.52 (s, 1H), 11.29 (br s, 1H), 11.36 (s, 1H), 11.83 (s, 1H) ppm; $^{13}$C NMR (acetone-d$_6$, 100 MHz) δ 28.03, 28.03, 28.03, 28.03, 28.03, 28.03, 52.10, 52.10, 83.40, 83.40, 109.66, 110.87, 114.19, 114.38, 116.28, 116.29, 119.66, 119.89, 123.34, 123.35, 124.09, 124.44, 124.48, 124.67, 130.89, 131.29, 132.42, 132.74, 134.03, 138.29, 138.58, 146.62, 162.93, 163.74, 166.68, 166.71, 188.03, 188.48 ppm; HRMS ESI (M+H$^+$) calculated for C$_{38}$H$_{39}$N$_8$O$_8$ 735.2891. found 735.2894; IR (KBr) 3405, 3139, 2977, 2933, 1745, 1631, 1590, 1414, 1368, 1242, 1157, 1047, 898, 793 cm$^{-1}$.

Di-tert-butyl 2,2'-(4,4'-((4,4',5,5'-tetrachloro-1'H-1,3'-bipyrrole-2,2'-dicarbonyl)bis(2-chloro-5-hydroxy-4,1-phenylene))bis(1H-1,2,3-triazole-4,1-diyl))diacetate (1-18)

To a solution of 23 (10 mg, 0.01 mmol) in MeCN (1 mL) at room temperature, NCS (10 mg, 0.07 mmol) was added slowly. The reaction was allowed to stir for about 2 h at room temperature. The reaction was quenched with water (5 mL) and extracted with EtOAc (5 mL×3). The combined organic layers were dried over anhydrous sodium sulfate, filtered and concentrated in vacuum. The residue was purified by column chromatography (40% EtOAc/petroleum ether, R$_f$=0.2) to yield 1-18 (2 mg, 14% yield) as a pale brown solid: melting point 103.7-105.0° C.; $^1$H NMR (400 MHz, acetone-d$_6$) δ 1.46 (s, 18H), 5.31 (s, 2H), 5.35 (s, 2H), 7.05 (s, 1H), 7.73 (s, 1H), 7.80 (s, 1H), 8.01 (s, 1H), 8.35 (s, 1H), 8.60 (s, 1H), 8.74 (s, 1H), 10.94 (s, 1H) ppm; $^{13}$C NMR (DMSO-d$_6$, 100 MHz) δ 28.00, 28.00, 28.00, 28.00, 28.04, 28.04, 51.50, 56.12, 69.00, 83.00, 108.20, 110.04, 113.40, 115.40, 116.83, 117.40, 119.00, 119.20, 119.58, 119.95, 121.80, 123.34, 124.04, 125.83, 126.50, 129.56, 131.14, 131.62, 132.43, 133.16, 142.33, 142.41, 155.48, 157.51, 166.53, 166.53, 179.98, 181.85 ppm; HRMS ESI (M+Na$^+$) calculated for C$_{38}$H$_{32}$Cl$_6$N$_8$NaO$_8$ 961.0372. found 961.0388; IR (KBr) 3442, 2979, 2920, 2851, 1744, 1629, 1460, 1427, 1383, 1243, 1155, 1025, 752, 666 cm$^{-1}$. HPLC purity, 96.2% (Flow rate: 1.0 mL/min; Column: Agilent ZORBAX 300SB-C8, 5 μm, 150×4.6 mm; Wavelength: UV 254 nm; Temperature: 25° C.; Mobile phase: MeOH:H$_2$O=75:25; t$_R$=5.9 min).

2,2'-(4,4'-((4,4',5,5'-Tetrachloro-1'H-1,3'-bipyrrole-2,2'-dicarbonyl)bis(2-chloro-5-hydroxy-4,1-phenylene))bis(1H-1,2,3-triazole-4,1-diyl))diacetic acid (1-19)

To a solution of 1-18 (30 mg, 0.03 mmol) in anhydrous CH$_2$Cl$_2$ (2 mL), CF$_3$COOH (2 mL) was slowly added via a syringe at 0° C. The reaction was allowed to warm up to room temperature and stirred for about 4 h. The reaction was concentrated in vacuum. The residue was purified by reverse-phase column chromatography (C18 reverse silica gel, 6% AcOH, 30% H$_2$O, 64% MeOH, R$_f$=0.2) to yield 1-19 (17 mg, 65% yield) as a pale brown solid: melting point 261.4-262.7° C.; $^1$H NMR (400 MHz, CD$_3$OD) δ 5.18 (s, 2H), 5.21 (s, 2H), 6.73 (s, 1H), 7.23 (s, 1H), 7.35 (s, 1H), 7.48 (s, 1H), 8.59 (s, 1H), 8.87 (s, 1H), 8.48 (s, 1H), 8.57 (s, 1H) ppm; $^{13}$C NMR (DMSO-d$_6$, 100 MHz) δ 52.98, 53.62, 108.07, 109.84, 116.57, 118.82, 119.32, 119.62, 121.71, 123.24, 123.81, 125.44, 125.90, 126.23, 129.42, 131.17, 131.66, 131.68, 132.88, 133.50, 141.85, 141.97, 155.58, 157.52, 161.00, 162.77, 169.56, 172.54, 179.98, 182.01 ppm; HRMS ESI (M+H$^+$) calculated for C$_{30}$H$_{17}$Cl$_6$N$_8$O$_8$ 826.9301. found 826.9308; IR (KBr) 3392, 2956, 2921, 2851, 1753, 1626, 1462, 1432, 1380, 1246, 1188, 1081, 1025, 770 cm$^{-1}$. HPLC purity, 98.8% (Flow rate: 1.0 mL/min; Column: Waters C18, 5 μm, 150×4.6 mm; Wavelength: UV 254 nm; Temperature: 25° C.; Mobile phase: MeOH:H$_2$O=65:35; t$_R$=4.2 min).

(4,4',5,5'-Tetrachloro-1'H-1,3'-bipyrrole-2,2'-diyl)bis ((4-(1-benzyl-1H-1,2,3-triazol-5-yl)-2-hydroxyphenyl)methanone) (1-20)

Under N$_2$, a mixture of 1-3 (20 mg, 0.04 mmol), (azidomethyl)benzene (29 mg, 0.22 mmol), and CuCl (4 mg, 0.04 mmol) was dissolved in THF (5 mL). The reaction was allowed to warm up to reflux and stirred for about 8 h. The suspension was filtered and the filtrate was concentrated in vacuum. The residue was purified by column chromatography (5% acetone, 31% EtOAc, 64% petroleum ether, R$_f$=0.3) to yield 1-20 (17 mg, 55% yield) as a yellow solid: melting point 116.5-118.0° C.; $^1$H NMR (400 MHz, CDCl$_3$) δ 5.56 (s, 2H), 5.57 (s, 2H), 6.16 (s, 1H), 7.01 (d, J=8.4 Hz, 1H), 7.28-7.31 (m, 7H), 7.32-7.40 (m, 7H), 7.51 (br s, 1H), 7.69 (s, 1H), 7.75 (s, 1H), 10.35 (br s, 1H), 10.83 (s, 1H), 11.39 (s, 1H) ppm; $^{13}$C NMR (CDCl$_3$, 100 MHz) δ 54.36, 54.36, 112.01, 114.28, 114.28, 115.89, 116.54, 117.18, 118.47, 118.65, 121.17, 121.32, 121.74, 121.94, 124.33, 124.84, 128.12, 128.12, 128.12, 128.19, 128.19, 128.19, 128.95, 128.95, 128.95, 129.22, 129.22, 129.22, 129.22, 131.25, 134.16, 134.16, 134.16, 137.75, 138.85, 146.47, 162.06, 163.05, 185.56, 187.37 ppm; HRMS ESI (M+H$^+$) calculated for C$_{40}$H$_{27}$Cl$_4$N$_8$O$_4$ 823.0909. found 823.0903; IR (KBr) 2955, 2919, 2850, 1717, 1628, 1592, 1457, 1228, 1047, 935, 912, 790, 699 cm$^{-1}$. HPLC purity, 98.5% (Flow rate: 1.0 mL/min; Column, Agilent ZORBAX 300SB-C8, 5 μm, 150×4.6 mm; Wavelength: UV 254 nm; Temperature: 25° C.; Mobile phase: MeOH:H$_2$O=85:15; t$_R$=12.5 min).

(4,4',5,5'-Tetrachloro-1'H-1,3'-bipyrrole-2,2'-diyl)bis((2-hydroxy-4-(1-phenyl-1H-1,2,3-triazol-5-yl)phenyl)methanone) (1-21)

Under $N_2$, a mixture of 1-3 (20 mg, 0.04 mmol), azidobenzene (26 mg, 0.22 mmol), and CuCl (4 mg, 0.04 mmol) was dissolved in THF (5 mL). The reaction was allowed to warm up to reflux and stirred for about 8 h. The suspension was filtered and the filtrate was concentrated in vacuum. The residue was purified by column chromatography (5% acetone, 31% EtOAc, 64% petroleum ether, $R_f$=0.3) to yield 1-21 (20 mg, 70% yield) as a yellow solid: melting point 128.7-130.3° C.; $^1$H NMR (400 MHz, CDCl$_3$) δ 6.24 (s, 1H), 7.16 (d, J=8.0 Hz, 1H), 7.41-7.48 (m, 6H), 7.52-7.56 (m, 5H), 7.77 (d, J=8.0 Hz, 4H), 8.24 (s, 1H), 8.30 (s, 1H), 10.35 (br s, 1H), 10.91 (s, 1H), 11.47 (s, 1H) ppm; $^{13}$C NMR (CDCl$_3$, 100 MHz) δ 109.13, 112.09, 114.48, 114.52, 116.00, 116.69, 117.17, 118.68, 118.83, 119.23, 119.40, 120.51, 120.51, 120.51, 120.51, 120.51, 120.51, 121.76, 122.02, 124.43, 124.86, 129.05, 129.09, 129.83, 129.83, 129.83, 129.83, 129.83, 131.29, 134.25, 136.64, 137.44, 138.55, 146.68, 162.15, 163.12, 185.54, 187.50 ppm; HRMS ESI (M+H$^+$) calculated for $C_{38}H_{23}Cl_4N_8O_4$ 795.0596. found 795.0590; IR (KBr) 2955, 2918, 2849, 1701, 1630, 1594, 1503, 1459, 1238, 1036, 935, 912, 757, 686 cm$^{-1}$. HPLC purity, 97.4% (Flow rate: 1.0 mL/min; Column: Agilent ZORBAX 300SB-C8, 5 μm, 150×4.6 mm; Wavelength: UV 254 nm; Temperature: 25° C.; Mobile phase: MeOH:H$_2$O=85:15; $t_R$=10.8 min).

(4,4',5,5'-Tetrachloro-1'H-1,3'-bipyrrole-2,2'-diyl)bis((4-(1-cyclohexyl-1H-1,2,3-triazol-5-yl)-2-hydroxyphenyl)methanone) (1-22)

Under $N_2$, a mixture of 1-3 (20 mg, 0.04 mmol), azidocyclohexane (27 mg, 0.22 mmol), and CuCl (4 mg, 0.04 mmol) was dissolved in THF (5 mL). The reaction was allowed to warm up to reflux and stirred for about 8 h. The suspension was filtered and the filtrate was concentrated in vacuum. The residue was purified by column chromatography (5% acetone, 31% EtOAc, 64% petroleum ether, $R_f$=0.3) to yield 1-22 (15 mg, 52% yield) as a yellow solid: melting point 143.8-145.0° C.; $^1$H NMR (400 MHz, CDCl$_3$) δ 1.25-1.39 (m, 2H), 1.44-1.59 (m, 4H), 1.78-1.87 (m, 6H), 1.94-1.97 (m, 4H), 2.25-2.27 (m, 4H), 4.49 (t, J=10.0 Hz, 2H), 6.21 (s, 1H), 7.06 (d, J=8.4 Hz, 1H), 7.31-7.37 (m, 4H), 7.51 (br s, 1H), 7.82 (s, 1H), 7.87 (s, 1H), 10.47 (br s, 1H), 10.91 (s, 1H), 11.44 (s, 1H) ppm; $^{13}$C NMR (CDCl$_3$, 100 MHz) δ 25.04, 25.04, 25.11, 25.11, 29.20, 29.65, 33.52, 33.52, 33.52, 33.52, 60.36, 60.36, 109.00, 112.00, 114.12, 114.22, 115.88, 116.54, 117.09, 118.32, 118.54, 119.10, 119.20, 121.64, 121.86, 124.26, 124.86, 131.25, 134.18, 134.18, 138.22, 139.29, 145.60, 145.60, 162.23, 163.12, 185.59, 187.39 ppm; HRMS ESI (M+H$^+$) calculated for $C_{38}H_{35}Cl_4N_8O_4$ 807.1535. found 807.1532; IR (KBr) 3129, 2923, 2853, 1718, 1628, 1593, 1448, 1413, 1392, 1334, 1297, 1228, 1052, 914, 790 cm$^{-1}$. HPLC purity, 95.0% (Flow rate: 1.0 mL/min; Column: Agilent ZORBAX 300SB-C8, 5 μm, 150×4.6 mm; Wavelength: UV 254 nm; Temperature: 25° C.; Mobile phase: MeOH:H$_2$O=85:15; $t_R$=20.9 min).

(4,4',5,5'-Tetrachloro-1'H-1,3'-bipyrrole-2,2'-diyl)bis((2-hydroxy-4-(1-octyl-1H-1,2,3-triazol-5-yl)phenyl)methanone) (1-23)

Under $N_2$, a mixture of 1-3 (20 mg, 0.04 mmol), 1-azidooctane (27 mg, 0.22 mmol), and CuCl (4 mg, 0.04 mmol) was dissolved in THF (5 mL). The reaction was allowed to warm up to reflux and stirred for about 8 h. The suspension was filtered and the filtrate was concentrated in vacuum. The residue was purified by column chromatography (5% acetone, 31% EtOAc, 64% petroleum ether, $R_f$=0.3) to yield 1-23 (15 mg, 48% yield) as a yellow solid: melting point 85.2-86.7° C.; $^1$H NMR (400 MHz, CDCl$_3$) δ 0.84-0.91 (m, 6H), 1.14-1.35 (m, 20H), 1.93-1.95 (m, 4H), 4.40 (t, J=6.4 Hz, 4H), 6.20 (s, 1H), 7.06 (d, J=8.4 Hz, 1H), 7.27-7.37 (m, 4H), 7.52 (br s, 1H), 7.80 (s, 1H), 7.85 (s, 1H), 10.48 (br s, 1H), 10.87 (s, 1H), 11.44 (s, 1H) ppm; $^{13}$C NMR (CDCl$_3$, 100 MHz) δ 22.55, 22.55, 26.44, 26.44, 28.91, 28.91, 28.91, 29.00, 29.00, 29.00, 30.23, 30.26, 31.65, 31.65, 50.60, 50.60, 109.00, 112.02, 114.22, 114.26, 115.89, 116.56, 117.13, 118.41, 118.61, 121.12, 121.25, 121.70, 122.00, 124.34, 124.87, 126.85, 131.27, 134.20, 137.99, 139.09, 146.00, 162.13, 163.10, 163.10, 185.59, 187.40 ppm; HRMS ESI (M+H$^+$) calculated for $C_{42}H_{47}Cl_4N_8O_4$ 867.2474. found 867.2482; IR (KBr) 3392, 3080, 2955, 2922, 2852, 1629, 1587, 1458, 1439, 1336, 1217, 1031, 914, 753, 703 cm$^{-1}$. HPLC purity, 99.7% (Flow rate: 1.0 mL/min; Column: Agilent ZORBAX 300SB-C8, 5 μm, 150×4.6 mm; Wavelength: UV 254 nm; Temperature: 25° C.; Mobile phase: MeOH:H$_2$O=90:10; $t_R$=10.1 min).

Diethyl 2,2'-(4,4'-((4,4',5,5'-tetrachloro-1'H-1,3'-bipyrrole-2,2'-dicarbonyl)bis(3-hydroxy-4,1-phenylene))bis(1H-1,2,3-triazole-4,1-diyl))diacetate (1-24)

Under $N_2$, a mixture of 1-3 (20 mg, 0.04 mmol), ethyl 2-azidoacetate (28 mg, 0.22 mmol), and CuCl (4 mg, 0.04 mmol) was dissolved in THF (5 mL). The reaction was allowed to warm up to reflux and stirred for about 4 h. The suspension was filtered and the filtrate was concentrated in vacuum. The residue was purified by column chromatography (5% acetone, 31% EtOAc, 64% petroleum ether, $R_f$=0.3) to yield 1-24 (15 mg, 52% yield) as a yellow solid: melting point 101.9-103.7° C.; $^1$H NMR (400 MHz, acetone-d$_6$) δ 1.21-1.29 (m, 6H), 4.19-1.26 (m, 4H), 5.39 (s, 4H), 6.16 (s, 1H), 7.23 (dd, J=8.4, 2.0 Hz, 1H), 7.33 (d, J=1.6 Hz, 1H), 7.39 (d, J=8.0 Hz, 1H), 7.42 (d, J=1.6 Hz, 1H), 7.92 (d, J=8.4 Hz, 1H), 8.20 (d, J=8.0 Hz, 1H), 8.39 (s, 1H), 8.49 (s, 1H) ppm; $^{13}$C NMR (CDCl$_3$, 100 MHz) δ 14.04, 14.04, 50.97, 50.97, 62.62, 62.62, 109.05, 112.01, 114.38, 114.38, 114.38, 115.96, 116.62, 117.08, 118.61, 118.73, 121.67, 121.90, 122.73, 122.87, 124.37, 124.83, 131.25, 134.22, 137.46, 138.60, 146.48, 162.05, 163.03, 166.12, 166.18, 185.58, 187.49, 187.49 ppm; HRMS ESI (M+H$^+$) calculated for $C_{34}H_{27}Cl_4N_8O_8$ 815.0706. found 815.0707; IR (KBr) 3670, 3389, 3080, 2959, 2920, 2850, 1752, 1631, 1584, 1481, 1439, 1216, 1030, 753 cm$^{-1}$. HPLC purity, 98.4% (Flow rate: 1.0 mL/min; Column: Agilent ZORBAX 300SB-C8, 5 m, 150×4.6 mm; Wavelength: UV 254 nm; Temperature: 25° C.; Mobile phase: MeOH:H$_2$O=75:25; $t_R$=7.7 min).

Di-tert-butyl 2,2'-(4,4'-((4,4',5,5'-tetrachloro-1'H-1,3'-bipyrrole-2,2'-dicarbonyl)bis(3-hydroxy-4,1-phenylene))bis(1H-1,2,3-triazole-4,1-diyl))diacetate (1-25)

Under $N_2$, a mixture of 1-3 (10 mg, 0.02 mmol), tert-butyl 2-azidoacetate (14 mg, 0.11 mmol), and CuCl (2 mg, 0.02 mmol) was dissolved in THF (5 mL). The reaction was allowed to warm up to reflux and stirred for about 8 h. The suspension was filtered and the filtrate was concentrated in vacuum. The residue was purified by column chromatography (5% acetone, 31% EtOAc, 64% petroleum ether, $R_f$=0.3) to yield 1-25 (13 mg, 83% yield) as a yellow solid: melting point 138.3-140.0° C.; $^1$H NMR (400 MHz, acetone-$d_6$) δ 1.46 (s, 9H), 1.47 (s, 9H), 5.28 (s, 4H), 6.17 (s, 1H), 7.23 (dd, J=8.4, 1.6 Hz, 1H), 7.34 (d, J=1.6 Hz, 1H), 7.40 (dd, J=8.4, 1.6 Hz, 1H), 7.43 (d, J=0.8 Hz, 1H), 7.91 (d, J=8.4 Hz, 1H), 8.18 (d, J=8.0 Hz, 1H), 8.38 (s, 1H), 8.48 (s, 1H) ppm; $^{13}$C NMR (CDCl$_3$, 100 MHz) δ 27.89, 27.89, 27.89, 27.89, 27.89, 27.89, 51.57, 51.57, 84.09, 84.09, 108.98, 111.88, 114.23, 114.30, 115.90, 116.59, 116.98, 118.59, 118.69, 121.66, 121.92, 122.74, 122.90, 122.90, 124.39, 124.82, 126.85, 131.32, 134.19, 137.45, 138.65, 146.32, 161.95, 162.98, 165.10, 165.16, 185.65, 187.45 ppm; HRMS ESI (M+H$^+$) calculated for $C_{38}H_{35}Cl_4N_8O_8$ 871.1332. found 871.1325; IR (KBr) 3425, 3141, 2980, 2931, 1745, 1630, 1599, 1454, 1369, 1239, 1156, 1048, 937, 852, 192 cm$^{-1}$. HPLC purity, 99.5% (Flow rate: 1.0 mL/min; Column: Agilent ZORBAX 300SB-C8, 5 m, 150×4.6 mm; Wavelength: UV 254 nm; Temperature: 25° C.; Mobile phase: MeOH:H$_2$O=80:20; $t_R$=7.3 min).

2,2'-(4,4'-((4,4',5,5'-Tetrachloro-1'H-1,3'-bipyrrole-2, 2'-dicarbonyl)bis(3-hydroxy-4,1-phenylene))bis(1H-1,2,3-triazole-4,1-diyl))diacetic acid (1-26)

To a solution of 1-25 (17 mg, 0.02 mmol) in anhydrous CH$_2$Cl$_2$ (2 mL) was slowly added CF$_3$COOH (2 mL) via a syringe at 0° C. The reaction was allowed to warm up to room temperature and stirred for about 4 h and concentrated in vacuum. The residue was purified by reverse-phase column chromatography (C18 reverse silica gel, 6% AcOH, 30% H$_2$O, 64% MeOH, $R_f$=0.2) to yield 1-26 (14 mg, 94% yield) as a yellow solid: melting point 100.3-102.0° C.; $^1$H NMR (400 MHz, DMSO-$d_6$) δ 4.80 (s, 2H), 4.83 (s, 2H), 6.09 (s, 1H), 7.15 (d, J=8.4 Hz, 1H), 7.22 (s, 2H), 7.32 (s, 1H), 7.53 (d, J=8.4 Hz, 1H), 7.97 (d, J=8.4 Hz, 1H), 8.38 (s, 1H), 8.41 (s, 1H) ppm; $^{13}$C NMR (DMSO-$d_6$, 100 MHz) δ 53.17, 53.22, 109.12, 109.58, 112.93, 114.34, 114.99, 116.28, 121.49, 122.71, 123.87, 124.51, 124.67, 129.03, 130.14, 132.35, 133.28, 135.63, 137.40, 145.28, 145.79, 158.86, 159.46, 169.77, 169.80, 172.88, 177.84, 182.18, 185.38, 190.74 ppm; HRMS ESI (M+$^H$) calculated for $C_{30}H_{19}Cl_4N_8O_8$ 759.0080. found 759.0054; IR (KBr) 3417, 3268, 3136, 1627, 1457, 1431, 1393, 1307, 1234, 1025, 1002, 936, 799, 688 cm$^{-1}$. HPLC purity, 99.7% (Flow rate: 1.0 mL/min; Column: Waters C18, 5 μm, 150×4.6 mm; Wavelength: UV 254 nm; Temperature: 25° C.; Mobile phase: MeOH:H$_2$O=65:35; $t_R$=4.1 min).

Enzyme-Linked Immunosorbent Assay (ELISA).

ELISAs were performed using a similar procedure as previously described (Doi K, et al. *J. Biol. Chem.* 2012, 287, 10224-10235). Briefly, 40 nM of biotinylated Bim BH3 peptide (Biomatik) in SuperBlock blocking buffer (Pierce) was incubated in high-binding capacity streptavidin-coated plates (Pierce) for 2 h. Compounds were diluted in 120 μl of PBS containing 10 nM of GST-Mcl-1 or GST-Bcl-x$_L$ in 1.5 mL tubes for 15 min. Wells were washed with wash buffer (PBS containing 0.05% Tween-20) and then 100 μL of the compound/GST-protein mixture was transferred to the wells. The plates were incubated for 2 h, and then wells were washed with wash buffer. HRP-conjugated anti-GST antibody (Bethyl Laboratories) was diluted 1:2000 in SuperBlock and 100 μL was transferred to each well. The plate was incubated for 1 h, and then wells were washed with wash buffer followed by PBS. 100 μL of SureBlue TMB Microwell Peroxidase Substrate (VWR) was added to each well and plates were developed for 5-10 min. 100 μL of 1 N HCl was added to each well to stop the reaction and absorbance was read at 450 nm using a Quant plate reader (Bio-Tek).

Protein Expression and Purification.

Mcl-1 (residues 172-327) was expressed as maltose binding protein (MBP) fusions from the pSV282 vector (Fire E, et al. *Protein Science.* 2010, 19, 507-519). Mcl-1 protein was expressed in BL21(DE3) Codon+ at 18° C. for 17 h. Cells were lysed using a high pressure homogenizer in 100 mM Tris-HCl pH 8, 250 mM NaCl, 5 mM 2-mercaptoethanol, 25 mM imidazole, and Complete EDTA-free protease inhibitor cocktail, and purified by Ni-affinity chromatography. Purified Mcl-1-MBP fusion protein was cleaved with TEV protease in 100 mM Tris-HCl pH 8, 60 mM Citrate, 5 mM BME at 4° C. for 17 h. Cleaved Mcl-1 was separated from MBP by subtractive Ni-affinity chromatography followed by gel filtration of the flow through using a Superdex75 10/300 gel filtration column. The uniformly $^{15}$N-labelled protein samples were prepared by growing the bacteria in minimal medium containing $^{15}$N-labeled NH$_4$Cl followed by the same purification procedure.

NMR Spectroscopy.

$^{15}$N-HSQC spectra were recorded on $^{15}$N-labelled Mcl-1 at 0.1 mM prepared in 50 mM potassium phosphate solution at pH 6.5, 50 mM NaCl and 1 mM DTT. Titrations up to 100 μM of 1-21 and 1-18 compounds were performed. NMR spectra were acquired at 25° C. on an Inova 600 MHz spectrometer equipped with a cryoprobe and analyzed in CCPNMR (Vranken W F, et al. *Proteins.* 2005, 59, 687-696).

Docking Studies.

NMR-guided docking of 1-21 into the X-ray crystal structure of Mcl-1 (PDB ID: 3KJ0) was performed using Glide (Maestro, Schrodinger) (Friesner R A et al. *J. Med. Chem.* 2004, 47, 1739-1749; Friesner R A, et al. *J. Med. Chem.* 2006, 49, 6177-6196; Halgren T A, et al. *J. Med. Chem.* 2004, 47, 1750-1759; Gavathiotis E, et al. *Nat. Chem. Biol.* 2012, 8, 639-645). The lowest-energy docking pose is consistent with the observed NMR-chemical shift perturbation data. Pymol is used for preparing the highlighted poses.

Results and Discussion

Optimization of marinopyrroles as either Mcl-1-selective, Bcl-x$_L$-selective or dual Mcl-1 and Bcl-x$_L$ antagonists will lead to valuable chemical probes and eventually to natural product-based anti-cancer agents. As shown in Table 2, marinopyrroles have at least eight sites amenable for optimization to accomplish the desired activity and selectivity. As discussed in disruptor design (vide supra), optimization includes substitutions on the pyrrole nitrogen, two phenyl rings, two carbonyl groups, replacing rings A and B, substitution at C-5' position, intramolecular cyclization between 2-OH and chloro on C-5', and substitution on the second pyrrole ring.

Mcl-1/Bim Disruption SAR.

The potency of the parent natural product Marinopyrrole A [(−)-1] to inhibit the binding of Mcl-1 to Bim was moderate (IC$_{50}$=12.5 μM) while the atropisomer (+)-1 exhibited similar potency (IC$_{50}$=12.7 μM), and the synthetic marinopyrrole A [(±)-1] displayed an IC$_{50}$ value of 8.9 μM. From the structure-activity relationship (SAR) studies of the symmetrical derivatives of (±)-1, the following overall conclusions can be drawn. Whereas, analogues of (±)-1 where the 4 and 4' hydrogens of phenyl rings A and B, respectively, were replaced by alkyls, alkenes and alkynes such as 1-2 to 1-5 gained some potency (up to 4-fold), those analogues where the 4- and 4'-hydrogens were replaced by sulfide- or bistriazole-containing moieties such as 1-10 and 1-26 gained substantial potency (up to 15-fold) (Table 2). Finally, analogues with hydroxyl- and carboxylate-containing groups at the 4 and 4' positions such as 1-7 and 1-16 lost potency, but neutralizing the negative charge of the carboxylate by alkylation improves inhibitory activity (compare 1-16 to 1-12, 1-15 to 1-9, 1-26 to 1-25, 1-19 to 1-18).

In the sulfide-containing series, derivatives with S-benzyl (1-10) or SCH$_2$(p-MeOPh) (1-11) were the most potent with IC$_{50}$ values of 700 nM (Table 2). In this series, replacing the phenyl in 1-10 (IC$_{50}$=700 nM) by the negatively-charged carboxylate as in 1-15 (6100 nM) lead to an 8.7-fold loss in potency to disrupt Mcl-1/Bim binding. However, neutralization of the 1-15 negative charge as in the ethylester derivative 1-9 improved the potency by 3.4-fold from 6100 nM to 1800 nM. This suggests that substituents at the 4- and 4'-positions of the sulfide-containing marinopyrroles bind to the Mcl-1 BH3 binding pocket in the vicinity of a negatively charged environment. Furthermore, replacing the sulfide by the corresponding sulphone consistently resulted in substantial (up 25-fold) loss of potency [compare 1-10 to 1-13 (16-fold loss), 1-11 to 1-14 (25-fold loss), 1-15 to 1-16 (10-fold loss) and 1-9 to 1-12 (21-fold loss)](Table 2). This loss of potency suggests that the BH3 binding pocket prefers the molecular geometry of the —S— over that of the —SO$_2$— groups.

In the bistriazole series, the octyl-triazole-containing analogue 1-23 was the most potent with an IC$_{50}$ value of 600 nM (Table 2). Replacing the octyl in 1-23 with cyclohexyl (1-22), phenyl (1-21) or benzyl (1-20) resulted in 2.3-, 2.5- and 5.5-fold loss of potency, respectively, suggesting that the extended aliphatic octyl is better accommodated than the cyclohexyl or phenyl in the BH3 binding domain in Mcl-1. Similarly, replacing the octyl with a methylene carboxylate (1-26), its corresponding ethyl (1-24) or t-butyl (1-25) esters also resulted in loss of potency. However, addition of chloro group to the 5- and 5'-positions to 1-26, 1-24 and 1-25 improves their potencies [compare 1-26 (16.5 µM) to 1-19 (5.2 µM); 1-24 (18.4 µM) to 1-17 (7.8 µM); 1-25 (5.1 µM) to 1-18 (1.6 µM)]. Interestingly, the same chloro modifications on the 5- and 5'-positions also enhanced the potency of marinopyrroles analogues that do not contain a triazole such as 1-7 (39.5 µM) to 1-8 (10.7 µM), suggesting that the chloro groups in those positions occupy a region in the BH3 binding domain of Mcl-1 that increases the affinity.

Another potent analogue of (±)-1 (IC$_{50}$=8.9 µM) is 1-6 (IC$_{50}$=1 µM) where the hydrogens at 4- and 4'-positions were replaced by trifluoromethanesulfonate groups (Table 2). However, replacing these hydrogens with trifluoromethyl groups as in 1-1 had little effect on potency (IC$_{50}$=8.1 µM). Substituting the 4- and 4'-hydrogens of (±)-1 with ethyl as in 1-5 (2.1 µM), CH═CH$_2$ as in 1-4 (3.7 µM) or ethyne as in 1-3 (3.7 µM) enhanced potency by 2- to 4-fold suggesting that this area of the marinopyrroles binds a hydrophobic pocket in BH3 binding domain of Mcl-1.

In the non-symmetrical marinopyrroles, replacing the 3'-, 4'- or 5'-hydrogens in (±)-1 with chloro groups as in 1-28, 1-30 or 1-29 resulted in a slight increase in potency (3.9 to 6.5 M). Similar substitutions with fluoro groups as in 1-31 to 1-33 did not enhance potency. N-methylation of (±)-1 as in 1-35 was not tolerated (IC$_{50}$>100 µM). Similarly, the N-methyl analogue of (±)-1 where the 2- and 2'-hydroxyl groups were replaced by 2- and 2'-methoxy groups also lost potency but only by 2-fold (IC$_{50}$=15.5 µM). This suggested that the NH group of marinopyrroles is involved in H-bonding interactions at the BH3 binding domain. Replacing phenol A but not phenol B of (±)-1 with an ethoxy carbonyl group as in 1-37 and 1-36, respectively, resulted in a 3-fold loss of activity (Table 2).

Bcl-x$_L$/Bim Disruption SAR.

While the (±)-1 was less potent at inhibiting Bcl-x$_L$/Bim (IC$_{50}$=16.4 µM) than Mcl-1/Bim binding (IC$_{50}$=8.9 µM), the SAR generated was similar, except for several important differences. As with Mcl-1/Bim SAR, some of the symmetrical derivatives of (∓)-1 where the 4- and 4'-hydrogens were replaced by sulfide-containing moieties gained a significant amount of potency (up to 23 fold). For example, derivatives with S-benzyl (1-10) or SCH$_2$(p-MeOPh) (1-11) were the most potent with IC$_{50}$ values of 600 nM (Table 2). Replacing the phenyl in 1-10 or the para-methoxy-phenyl in 1-11 by the negatively-charged carboxylate as in 1-15 was not tolerated (IC$_{50}$>100 µM). However, neutralization of the 1-15 negative charge as in the ethylester derivative 1-9 (IC$_{50}$=1200 nM) greatly enhanced the potency by over 83-fold. Another substitution that was not tolerated is the replacement of the sulfide by sulphone spacer (compare 1-10 to 1-13, 1-11 to 1-14, 1-15 to 1-16 and 1-9 to 1-12). As was the case for Mcl-1/Bim, among the bistriazole-containing analogues, the octyl-triazole-containing analogue 1-23 was the most potent to inhibit Bcl-x$_L$/Bim binding [IC$_{50}$=500 nM; 32.8-fold more potent than (±)-1 (Table 2)]. However, unlike in Mcl-1/Bim, replacing the octyl in 1-23 with phenyl 1-21 (IC$_{50}$=800 nM) or benzyl 1-20 (IC=1600 nM) were better than with cyclohexyl 1-22 (IC$_{50}$=3100 nM) (Table 2). Replacing the octyl with a methylene carboxylate (1-26) and its corresponding ethyl ester (1-24) were not tolerated. In contrast to Mcl-1/Bim, addition of chloro groups to the 5- and 5'-positions to 1-26, 1-24 and 1-25 as in 1-19, 1-17 and 1-18, respectively, did not improve their potencies, neither did it enhance the potency of marinopyrroles analogues that do not contain a triazole (compare 1-7 to 1-8). Hydrophobic substitutions at the 4- and 4'-positions of (±)-1 with trifluoromethanesulfonate groups as in 1-6, ethyl as in 1-5, ethyl alkene as in 1-4, ethyne as in 1-3 and CF$_3$ as in 1-1 all moderately improved potency with 1-6 being the most potent (Table 2).

In the non-symmetrical marinopyrroles, replacing the 3'- and 4'-but not the 5'-hydrogens in (±)-1 with chloro groups as in 1-28, 1-30 and 1-29, respectively, resulted in a slight increase in potency. Similar substitutions with fluoro groups as in 1-31 to 1-33 decreased potency. Unlike in Mcl-1/Bim where it was not tolerated, N-methylation of (±)-1 as in 1-35 (IC$_{50}$=7.1 M) increase potency of (±)-1 (IC$_{50}$=16.4 µM) to inhibit Bcl-x$_L$/Bim binding. In contrast, the N-methyl analogue of (±)-1 where the 2- and 2'-hydroxyl groups were replaced by 2- and 2'-methoxy groups lost 4-fold potency (IC$_{50}$=64.9 µM). Finally, replacing phenol A but not phenol B of (±)-1 with an ethoxy carbonyl group as in 1-37 and 1-36, respectively, resulted in a 6-fold loss of activity (Table 2).

Mcl-1-Selective, Bcl-x$_L$-Selective and Dual Mcl-1/Bcl-x$_L$ Marinopyrrole Antagonists From the SAR results several selective Mcl-1/Bim and Bcl-x$_L$/Bim disruptors emerged. The most selective Mcl-1 antagonist was 1-15 with over 16-fold more selectivity for disrupting Mcl-1/Bim over Bcl-x$_L$/Bim binding. However, neutralizing the carboxylate negative charge with an ethyl ester as in 1-9 or replacing the carboxylate with either a phenyl (1-10) or a methoxyphenyl (1-11) not only greatly increased the potency as discussed above, but also reversed the selectivity resulting in some of the most potent Mcl-1 and Bcl-x$_L$ dual inhibitors, with 1-9 being slightly more potent against Bcl-x$_L$ (Table 2). In the triazole series, 1-20 with a benzyl and 1-21 with a phenyl were 2-fold more selective for Bcl-$x_L$ over Mcl-1. This selectivity was reversed towards Mcl-1 when the benzyl or phenyl were replaced with ethyl carboxylate as in 1-24 (5.4 fold), carboxylate as in 1-26 (3.0 fold), cyclohexyl as in 1-22 (2.8 fold) or t-butyl carboxylate as in 1-25 (1.6 fold). Replacement with an octyl group as in 1-23 resulted in one of the most potent dual Mcl-1 and Bcl-$x_L$ antagonists. In the triazole series adding chloro groups to the 5- and 5'-positions increases selectivity for Mcl-1 over Bcl-$x_L$ [compare 1-17 (12.9 fold) to 1-24 (5.4 fold), 1-19 (9.6 fold) to 1-26 (3 fold) and 1-18 (8.3 fold) to 1-25 (1.6 fold)].

Substituting the 4- and 4'-hydrogens in (±)-1 with hydrophobic groups such as ethyl alkene (1-4), methyl (1-2), ethyne (1-3), ethyl (1-5) and $CF_3$ (1-1) all lead to dual Mcl-1 and Bcl-$x_L$ antagonists (Table 2). A number of non-symmetrical analogues were also dual Mcl-1 and BclxL antagonists. These include 1-27, 1-30, 1-31, and others (Table 2). The most selective Bcl-$x_L$ antagonist is 1-35 with 12.7-fold selectivity for Bcl-$x_L$ over Mcl-1. Replacing the 2- and 2'-hydroxyl groups in 1-35 with 2- and 2'-methoxy groups as in 1-34 leads to full reversal to a Mcl-1 selective antagonist (4.2 fold), suggesting the key roles that the hydroxyl groups play in the binding of 1-35 to the BH3 domain of Bcl-$x_L$. Furthermore, replacing the N-methyl in 1-35 with a hydrogen as in (±)-1 also leads to reversal of selectivity for Mcl-1 (1.8 fold) suggesting the importance of the N-hydrogen in binding to Mcl-1 but not Bcl-$x_L$.

Scheme 11. Potential sites amenable for optimization.

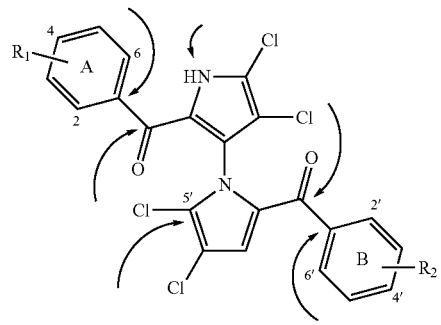

TABLE 2-A

| | ELISA results and physicochemical property of marinopyrroles. | | | | |
|---|---|---|---|---|---|
| ID | $R^1$ | $R^2$ | Mcl-1/Bim[a] | Bcl-$x_L$/Bim[a] | Clog p[b] |
| (±)-1[c] | 2-OH | 2'-OH | 8.9 ± 1.0 | 16.4 ± 3.3 | 5.6 |
| (−)-1[c] | 2-OH | 2'-OH | 12.5 ± 1.4 | 12.0 ± 2.8 | 5.6 |
| (+)-1[c] | 2-OH | 2'-OH | 12.7 ± 1.0 | 19.7 ± 3.6 | 5.6 |
| 1-17 | 2-OH-5-Cl-4-(triazole-$CH_2CO_2Et$) | 2'-OH-5'-Cl-4'-(triazole-$CH_2CO_2Et$) | 7.8 ± 1.5 | >100 | 5.9 |
| 1-18 | 2-OH-5-Cl-4-(triazole-$CH_2CO_2^tBu$) | 2'-OH-5'-Cl-4'-(triazole-$CH_2CO_2^tBu$) | 1.6 ± 0.6 | 14.0 ± 4.7 | 6.9 |
| 1-19 | 2-OH-5-Cl-4-(triazole-$CH_2CO_2H$) | 2'-OH-5'-Cl-4'-(triazole-$CH_2CO_2H$) | 5.2 ± 0.8 | >50 | 5.1 |
| 1-20 | 2-OH-4-(triazole-$CH_2$-phenyl) | 2'-OH-4'-(triazole-$CH_2$-phenyl) | 3.3 ± 0.9 | 1.6 ± 0.3 | 8.6 |
| 1-21 | 2-OH-4-(triazole-phenyl) | 2'-OH-4'-(triazole-phenyl) | 1.5 ± 0.2 | 0.8 ± 0.2 | 8.4 |
| 1-22 | 2-OH-4-(triazole-phenyl) | 2'-OH-4'-(triazole-cyclohexyl) | 1.4 ± 0.5 | 3.8 ± 1.3 | 8.2 |

TABLE 2-A-continued

ELISA results and physicochemical property of marinopyrroles.

| ID | R[1] | R[2] | Mcl-1/Bim[a] | Bcl-x$_L$/Bim[a] | Clog p[b] |
|---|---|---|---|---|---|
| 1-23 | 2-OH-4-[triazole-N-C7H15] 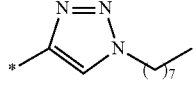 | 2'-OH-4'-[triazole-N-C7H15] 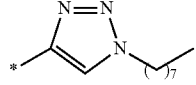 | 0.6 ± 0.3 | 0.5 ± 0.1 | 10.6 |
| 1-24 | 2-OH-4-[triazole-N-CH2CO2Et] 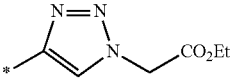 | 2'-OH-4'-[triazole-N-CH2CO2Et] 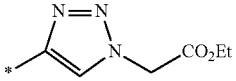 | 18.4 ± 0.3 | >100 | 4.9 |
| 1-25 | 2-OH-4-[triazole-N-CH2CO2tBu] 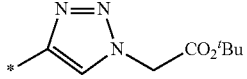 | 2'-OH-4'-[triazole-N-CH2CO2tBu] 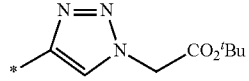 | 5.1 ± 0.4 | 8.1 ± 2.9 | 5.8 |
| 1-26 | 2-OH-4-[triazole-N-CH2CO2H] 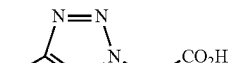 | 2'-OH-4'-[triazole-N-CH2CO2H] 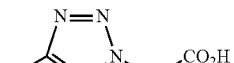 | 16.5 ± 1.9 | >50 | 4.1 |

[a]IC$_{50}$ in μM (average ± SEM, n ≥ 3) unless specified;
[b]Calculated using ChemAxon;
[c]Activity as disruptors of Mcl-1 and Bcl-x$_L$, reported previously and here for SAR discussion (Cheng C, et al. Submitted to *Mar. Drugs*);

TABLE 2-B

ELISA results and physicochemical property of marinopyrroles.

| ID | R[1] | R[2] | Mcl-1/Bim[a] | Bcl-x$_L$/Bim[a] | Clog p[b] |
|---|---|---|---|---|---|
| (±)-1[c] | 2-OH | 2'-OH | 8.9 ± 1.0 | 16.4 ± 3.3 | 5.6 |
| (−)-1[c] | 2-OH | 2'-OH | 12.5 ± 1.4 | 12.0 ± 2.8 | 5.6 |
| (+)-1[c] | 2-OH | 2'-OH | 12.7 ± 1.0 | 19.7 ± 3.6 | 5.6 |
| 1-1[d] | 2-OH-4-CF$_3$ | 2'-OH-4'-CF$_3$ | 8.1 ± 0.9 | 9.7 ± 1.3 | 7.3 |
| 1-2 | 2-OH-5-Cl-4-Me | 2'-OH-5'-Cl-4'-Me | 2.6 ± 0.6 | 2.5 ± 0.4 | 7.5 |
| 1-3 | 2-OH-4-C≡CH | 2'-OH-4'-C≡CH | 3.9 ± 0.2 | 5.6 ± 0.5 | 5.9 |
| 1-4 | 2-OH-4-CH=CH$_2$ | 2'-OH-4'-CH=CH$_2$ | 3.7 ± 0.5 | 3.5 ± 0.7 | 7.4 |
| 1-5 | 2-OH-4-Et | 2'-OH-4'-Et | 2.1 ± 0.5 | 3.9 ± 1.2 | 7.3 |
| 1-6[d] | 2-OH-4-OSO$_2$CF$_3$ | 2'-OH-4'-OSO$_2$CF$_3$ | 1.0 ± 0.3 | 2.5 ± 0.7 | 8.1 |
| 1-7[d] | 2-OH-4-OH | 2'-OH-4'-OH | 39.5 ± 6.2 | >50 | 5.0 |
| 1-8[d] | 2-OH-5-Cl-4-OH | 2'-OH-5'-Cl-4'-OH | 10.7 ± 0.2 | >50 | 6.0 |
| 1-9 | 2-OH-4-SCH$_2$CO$_2$Et | 2'-OH-4'-SCH$_2$CO$_2$Et | 1.8 ± 0.3 | 1.2 ± 0.2 | 6.1 |
| 1-10 | 2-OH-4-SCH$_2$Ph | 2'-OH-4'-SCH$_2$Ph | 0.7 ± 0.2 | 0.6 ± 0.2 | 10.2 |
| 1-11 | 2-OH-4-SCH$_2$(p-MeOPh) | 2'-OH-4'-SCH$_2$(p-MeOPh) | 0.7 ± 0.1 | 0.6 ± 0.1 | 9.7 |
| 1-12 | 2-OH-4-SO$_2$CH$_2$CO$_2$Et | 2'-OH-4'-SO$_2$CH$_2$CO$_2$Et | 37.3 ± 3.1 | >50 | 3.7 |
| 1-13 | 2-OH-4-SO$_2$CH$_2$Ph | 2'-OH-4'-SO$_2$CH$_2$Ph | 11.2 ± 4.0 | 69.3 ± 15.8 | 6.9 |
| 1-14 | 2-OH-4-SO$_2$CH$_2$(p-MeOPh) | 2'-OH-4'-SO$_2$CH$_2$(p-MeOPh) | 17.4 ± 3.1 | >100 | 6.4 |
| 1-15 | 2-OH-4-SCH$_2$CO$_2$H | 2'-OH-4'-SCH$_2$CO$_2$H | 6.1 ± 1.3 | >100 | 5.3 |
| 1-16 | 2-OH-4-SO$_2$CH$_2$CO$_2$H | 2'-OH-4'-SO$_2$CH$_2$CO$_2$H | 63.0 ± 5.4 | >100 | 2.9 |
| 1-27[e] | 2-OMe | 2'-OMe-4'-Cl | 8.0 ± 1.6 | 9.5 ± 2.2 | 4.9 |
| 1-28[e] | 2-OH | 2'-OH-3'-Cl | 4.1 ± 1.4 | 10.1 ± 2.2 | 6.1 |
| 1-29[e] | 2-OH | 2'-OH-5'-Cl | 3.9 ± 1.1 | 18.3 ± 3.0 | 6.1 |
| 1-30[e] | 2-OH | 2'-OH-4'-Cl | 6.5 ± 1.3 | 9.2 ± 2.3 | 6.1 |
| 1-31[f] | 2-OH | 2'-OH-5'-F | 8.9 ± 0.9 | 13.3 ± 3.3 | 5.7 |
| 1-32[f] | 2-OH | 2'-OH-4'-F | 9.6 ± 0.4 | 21.3 ± 5.6 | 5.7 |
| 1-33[f] | 2-OH | 2'-OH-6'-F | 13.1 ± 0.3 | 45.7 ± 10.0 | 5.7 |
| 1-34[g] | 2-OMe | 2'-OMe | 15.5 ± 3.3 | 64.9 ± 15.5 | 4.6 |
| 1-35[g] | 2-OH | 2'-OH | >100 | 7.1 ± 2.1 | 5.8 |
| 1-36[h] | CO$_2$Et replacing COAr | 2'-OH | 11.5 ± 1.9 | 17.6 ± 4.5 | 4.5 |

TABLE 2-B-continued

ELISA results and physicochemical property of marinopyrroles.

| ID | R[1] | R[2] | Mcl-1/Bim[a] | Bcl-$x_L$/Bim[a] | Clog p[b] |
|---|---|---|---|---|---|
| 1-37[h] | 2-OH | CO$_2$Et replacing COAr | 25.1 ± 4.7 | 96.6 | 4.5 |
| ABT-263 | | | | 4.3 ± 0.4 nM | |

[a]IC$_{50}$ in μM (average ± SEM, n ≥ 3) unless specified;
[b]Calculated using ChemAxon;
[c]Activity as disruptors of Mcl-1 and Bcl-$x_L$ reported previously and here for SAR discussion (Cheng C, et al. Submitted to Mar. Drugs);
[d]Chemistry, anti-MRSA activity and Clog p were reported previously (Cheng C, et al. Mar. Drugs. 2013, 11, 2927-2948);
[e]Chemistry and anti-MRSA activity were reported previously (Liu Y, et al. Mar. Drugs. 2012, 10, 953-962);
[f]Chemistry and anti-MRSA activity were reported previously (Liu Y, et al. Submitted to Mar. Drugs);
[g]N—Me analogue;
[h]Compounds reported previously (Nicolaou K C, et al. Tetrahedron Lett. 2011, 52, 2041-2043).

CONCLUSIONS

Described herein is the design, synthesis and SAR studies of marinopyrrole derivatives. Structural characterization of marinopyrrole binding to Mcl-1 suggests that bistriazole marinopyrrole 1-21 occupies the p1-p4 pockets along α-helical Bim peptide by NMR chemical shift perturbations assisted with molecular modeling. Comprehensive SAR studies demonstrated: i) symmetrical marinopyrroles with hydrophobic substituents in the para-position to the carbonyl group are desired for activity against Mcl-1/Bim and Bcl-$x_L$/Bim but hydrophilic substituents are not tolerated; ii) substituents with sulfide spacers lead to some of the most potent disruptors of Mcl-1/Bim and Bcl-$x_L$/Bim binding, but those with sulfone spacers are tolerated; iii) substituents with triazole spacer containing octyl, cyclohexyl and phenyl are most potent against both Mcl-1 and Bcl-$x_L$, but those containing carboxylates such as in 1-17, 1-19, 1-24 and 1-26 are not active against Bcl-$x_L$/Bim; iv) substituents with chlorine or fluorine in B ring of non-symmetrical marinopyrroles are tolerated in most cases; v) N-methylation of marinopyrrole A (1-36) leads to high selectivity for Bcl-$x_L$/Bim over Mcl-/Bim whereas the sulfide 1-15 was much more selective for Mcl-1 over Bcl-$x_L$; vi) replacing A ring with CO$_2$Et is also allowed.

Example 4

Previous reports have discussed the ability of marinopyrrole A to inhibit the binding of Mcl-1 to Bim. However, marinopyrrole A only moderately inhibits the binding to Mcl-1 to Bim (8.9 μM), its selectivity for Mcl-1 over Bcl-$x_L$ is only two fold, and it suffers from poor solubility. Herein, marinopyrrole A analogues were synthesized which can: improve solubility and potency, identify chemical probes selective for Mcl-1, Bcl-$x_L$ or Bcl-2, and be developed as anti-cancer drugs. The molecular geometry of marinopyrrole A offers excellent opportunities to reach these goals by decorating this natural product based bispyrrole system with a large number of diverse functional groups. Marinopyrrole has at least eight sites amenable to optimization to accomplish the desired activity and selectivity.

Results and Discussion

Structure activity relationship studies using Mcl-1/Bim and Bcl-$x_L$/Bim ELISA assays were used to identify marinopyrrole A analogues that are Mcl-1-selective and Bcl-$x_L$-selective antagonists as well as dual inhibitors of Bim binding to both Mcl-1 and Bcl-$x_L$. The parent marinopyrrole A [1=(±)–(1)] inhibits the binding of Mcl-1 to Bim with only moderate potency (IC$_{50}$=8.9 μM) (Table 3). All data reported in this example were performed with both Mcl-1 and Bcl-xL at 10 nM. Table 3 shows that substitutions of the para-hydrogens relative to the carbonyl group on both rings A and B in 1 with sulfide- or bistriazole-containing moieties such as I-13 and II-11 resulted in the most potent analogues (500 nM; up to 32-fold more potent than 1). Derivatives with alkyls, alkenes, alkynes and trifluoromethanesulphonate at the para positions such as I-2 to I-6, respectively, gained moderate potency (up to nine-fold). The most selective Mcl-1 antagonist was sulfide-containing 1-10 with over 16-fold more selectivity for disrupting Mcl-1/Bim over Bcl-xL/Bim binding, whereas the most selective Bcl-xL antagonist was VI-12 (N-methyl-1) with 12.7-fold selectivity for Bcl-xL over Mcl-1. The most potent dual Mcl-1 and Bcl-xL antagonists were sulfide 1-13 and triazole II-9 (Table 3).

Scheme 12. Marinopyrrole derivatives.

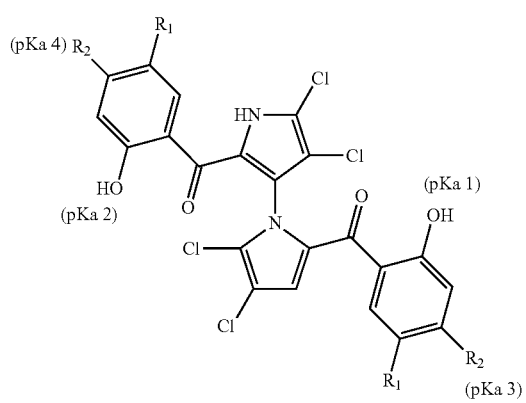

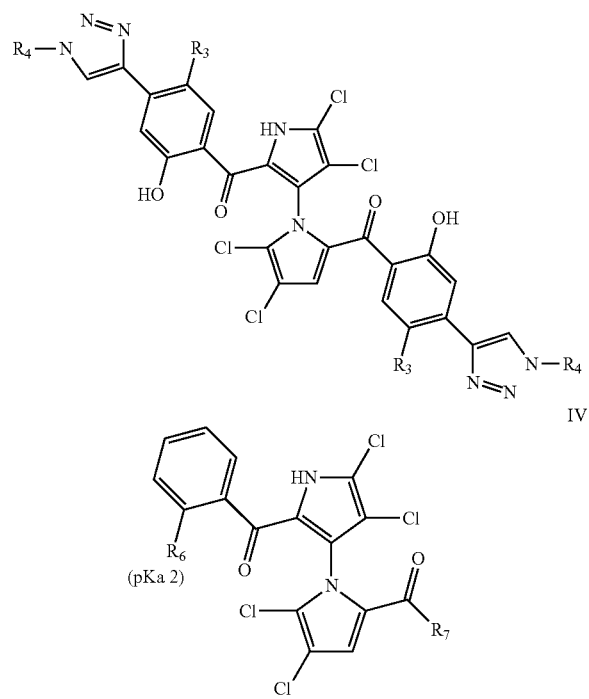

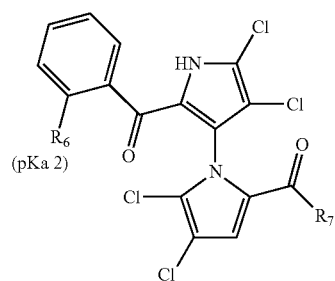

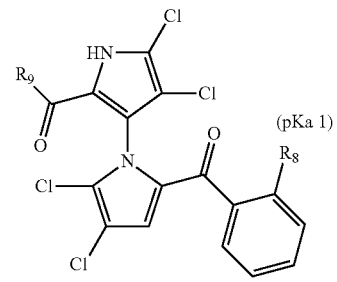

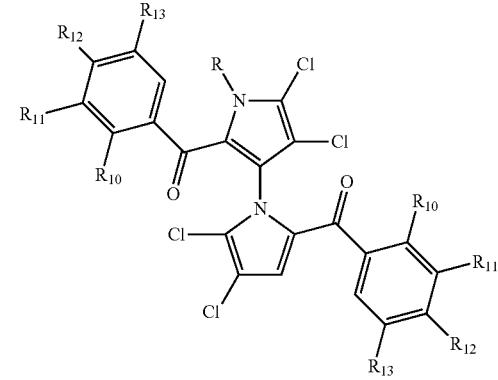

TABLE 3-A

ELISA results of selected marinopyrroles of structure I

| ID | R[1] | R[2] | Mcl-1-Bim[a] | Bcl-xL-Bim[a] | pK$_a$ 1[d] | pK$_a$ 2[d] | pK$_a$ 3[d,e] | pK$_a$ 4[d,e] | Clog p[d] |
|---|---|---|---|---|---|---|---|---|---|
| (±)-1 | H | H | 8.9 ± 1.0 | 16.4 ± 3.3 | 7.8 | 8.4 | — | — | 5.6 |
| (+)-1 | H | H | 12.7 ± 1.0 | 19.7 ± 3.6 | — | — | — | — | — |
| (−)-1 | H | H | 12.5 ± 1.4 | 12.0 ± 2.8 | — | — | — | — | — |
| I-1 | H | CF$_3$ | 8.1 ± 0.9 | 9.7 ± 1.3 | — | — | — | — | — |
| I-2 | H | CH$_2$C≡CH | 3.9 ± 0.2 | 5.6 ± 0.5 | — | — | — | — | — |
| I-3 | H | CH$_2$CH=CH$_2$ | 3.7 ± 0.5 | 3.5 ± 0.7 | — | — | — | — | — |
| I-4 | Cl | CH$_3$ | 2.6 ± 0.6 | 2.5 ± 0.4 | — | — | — | — | — |
| I-5 | H | CH$_2$CH$_3$ | 2.1 ± 0.5 | 3.9 ± 1.3 | — | — | — | — | — |
| I-6 | H | OSO$_2$CF$_3$ | 1.0 ± 0.3 | 2.1 ± 0.7 | — | — | — | — | — |
| I-7 | H | OH | 39.5 ± 6.2 | >50 | — | — | — | — | — |
| I-8 | Cl | OH | 10.7 ± 0.2 | >50 | — | — | — | — | — |
| I-9 | H | SCH$_2$CO$_2$CH$_2$CH$_3$ | 1.8 ± 0.3 | 1.2 ± 0.2 | 7.8 | 8.4 | — | — | 6.1 |
| I-10 | H | SCH$_2$CO$_2$H | 6.1 ± 1.3 | >100 | 7.8 | 8.4 | 2.9 | 3.5 | 5.3 |
| I-11 | H | SO$_2$CH$_2$CO$_2$H | 63.0 ± 5.4 | >100 | 6.7 | 7.3 | 2.2 | 2.9 | 2.9 |
| I-12 | H | SO$_2$CH$_2$CO$_2$CH$_2$CH$_3$ | 37.3 ± 3.1 | >100 | 6.7 | 7.3 | — | — | 3.7 |
| I-13[b] | H | SCH$_2$Ph | 0.7 ± 0.2 | 0.6 ± 0.2 | 7.8 | 8.4 | — | — | 10.2 |
| I-14[b] | H | SO$_2$CH$_2$Ph | 7.3 ± 1.4 | 69.3 ± 5.8 | 6.7 | 7.3 | — | — | 6.9 |
| I-15[b] | H | SCH$_2$-para-CH$_3$OPh | 0.7 ± 0.1 | 0.6 ± 0.1 | 7.8 | 8.4 | — | — | 9.7 |
| I-16 | H | SO$_2$CH$_2$-para-CH$_3$OPh | 17.4 ± 3.1 | >100 | 6.7 | 7.3 | — | — | 6.4 |
| I-17 | H | CO$_2$CH$_3$ | 16.9 ± 2.3 | >100 | — | — | — | — | — |
| I-18 | H | CO$_2$H | 61.4 ± 7.6 | >100 | — | — | — | — | — |
| I-19 | H | PO(OCH$_2$CH$_3$)$_2$ | 7.7 ± 2.2 | >100 | — | — | — | — | — |
| I-20 | H | PO(OH)$_2$ | 10.9 ± 3.1 | 27.3 ± 7.2 | — | — | — | — | — |
| I-21[c] | H | H | 4.5 ± 0.9 | 7.3 ± 0.9 | — | — | — | — | — |

[a]IC$_{50}$ (average ± SEM) in μM, n ≥ 3
[b]Ph = phenyl
[c]tetra-Br replacing tetra-Cl in 1
[d]calculated using ChemAxon Software Version 5.12.3
[e]pK$_a$ values frm carboxylic acid group

TABLE 3-B

ELISA results of selected marinopyrroles of structure II

| ID | $R^3$ | $R^4$ | Mcl-1-Bim$^a$ | Bcl-xL-Bim$^a$ |
|---|---|---|---|---|
| II-2 | Cl | CH$_2$CO$_2$CH$_2$CH$_3$ | 7.8 ± 1.5 | >100 |
| II-3$^d$ | Cl | CH$_2$CO$_2$CO$_2$Bu | 1.6 ± 0.6 | 13.2 ± 3.9 |
| II-4 | Cl | CH$_2$CO$_2$H | 5.2 ± 0.8 | >50 |
| II-5 | H | CH$_2$CO$_2$CH$_2$CH$_3$ | 18.4 ± 0.3 | >100 |
| II-6$^d$ | H | CH$_2$CO$_2$Bu | 5.1 ± 0.4 | 8.1 ± 2.5 |
| II-7 | H | CH$_2$CO$_2$H | 16.5 ± 1.9 | >50 |
| II-8$^b$ | H | CH$_2$Ph | 3.3 ± 0.9 | 1.6 ± 0.3 |
| II-9$^b$ | H | Ph | 1.5 ± 0.2 | 0.8 ± 0.2 |
| II-10 | H | cyclohexane | 1.4 ± 0.5 | 3.8 ± 1.3 |
| II-11 | H | n-octane | 0.6 ± 0.3 | 0.5 ± 0.1 |

$^a$IC$_{50}$ (average ± SEM) in μM, n ≥ 3
$^b$Ph = phenyl
$^d$Bu = butyl

TABLE 3-C

ELISA results of selected marinopyrroles of structure IV

| ID | $R^6$ | $R^7$ | Mcl-1-Bim$^a$ | Bcl-xL-Bim$^a$ | pK$_a$ 1$^c$ | pK$_a$ 2$^c$ | pK$_a$ 3$^{c,d}$ | pK$_a$ 4$^{c,d}$ | Clog p$^c$ |
|---|---|---|---|---|---|---|---|---|---|
| IV-1 | OH | OCH$_2$CH$_3$ | 25.1 ± 4.7 | 96.6 (n = 2) | — | 8.1 | — | — | 4.5 |
| IV-2$^b$ | OCH$_3$ | 4-Cl-2-OCH$_3$—Ph | 8.0 ± 1.6 | 9.5 ± 2.2 | — | — | — | — | — |
| IV-3$^b$ | OH | 3-Cl-2-OH—Ph | 4.1 ± 1.4 | 10.1 ± 2.2 | — | — | — | — | — |
| IV-4$^b$ | OH | 5-Cl-2-OH—Ph | 3.9 ± 1.1 | 18.3 ± 3.0 | — | — | — | — | — |
| IV-5$^b$ | OH | 4-Cl-2-OH—Ph | 6.5 ± 1.3 | 9.2 ± 2.3 | — | — | — | — | — |
| IV-6$^b$ | OH | 5-F-2-OH—Ph | 8.9 ± 0.9 | 13.3 ± 3.3 | — | — | — | — | — |
| IV-7$^b$ | OH | 4-F-2-OH—Ph | 9.6 ± 0.4 | 21.3 ± 5.6 | — | — | — | — | — |
| IV-8$^b$ | OH | 6-F-2-OH—Ph | 13.1 ± 0.3 | 43.7 ± 10.0 | — | — | — | — | — |

$^a$IC$_{50}$ (average ± SEM) in 1 μM, n ≥ 3
$^b$Ph = phenyl
$^c$calculated using ChemAxon Software Version 5.12.3
$^d$pK$_a$ values frm carboxylic acid group

TABLE 3-D

ELISA results of selected marinopyrroles of structure V

| ID | $R^8$ | $R^9$ | Mcl-1-Bim$^a$ | Bcl-xL-Bim$^a$ | pK$_a$ 1$^b$ | pK$_a$ 2$^b$ | pK$_a$ 3$^{b,c}$ | pK$_a$ 4$^{b,c}$ | Clog p$^b$ |
|---|---|---|---|---|---|---|---|---|---|
| V-1 | OH | OCH$_2$CH$_3$ | 11.5 ± 1.9 | 17.6 ± 4.5 | 8.1 | — | — | — | 4.5 |

$^a$IC$_{50}$ (average ± SEM) in μM, n ≥ 3
$^b$calculated using ChemAxon Software Version 5.12.3
$^c$pK$_a$ values frm carboxylic acid group

TABLE 3-E

ELISA results of selected marinopyrroles of structure VI

| ID | $R^{10}$ | $R^{11}$ | $R^{12}$ | $R^{13}$ | R | Mcl-1-Bim$^a$ | Bcl-xL-Bim$^a$ |
|---|---|---|---|---|---|---|---|
| VI-1 | OCH | H | H | H | H | — | — |
| VI-2 | H | OCH$_3$ | H | H | H | — | — |
| VI-3 | H | H | OCH$_3$ | H | H | — | — |
| VI-4 | F | H | H | H | H | — | — |
| VI-5 | H | F | H | H | H | — | — |
| VI-6 | H | H | F | H | H | — | — |
| VI-7 | CF$_3$ | H | H | H | H | — | — |
| VI-8 | H | H | CF$_3$ | H | H | — | — |
| VI-9 | OH | H | OCH$_3$ | Cl | H | — | — |
| VI-10 | OCH$_3$ | H | OCH$_3$ | Cl | H | — | — |
| VI-11 | OCH$_3$ | H | H | H | CH$_3$ | 15.5 ± 3.3 | 64.9 ± 15.5 |
| VI-12 | OH | H | H | H | CH$_3$ | >100 | 7.9 ± 1.8 |

$^a$IC$_{50}$ (average ± SEM) in μM, n ≥ 3

Fluorescence Quenching Demonstrates Direct Binding.

Figure 5:
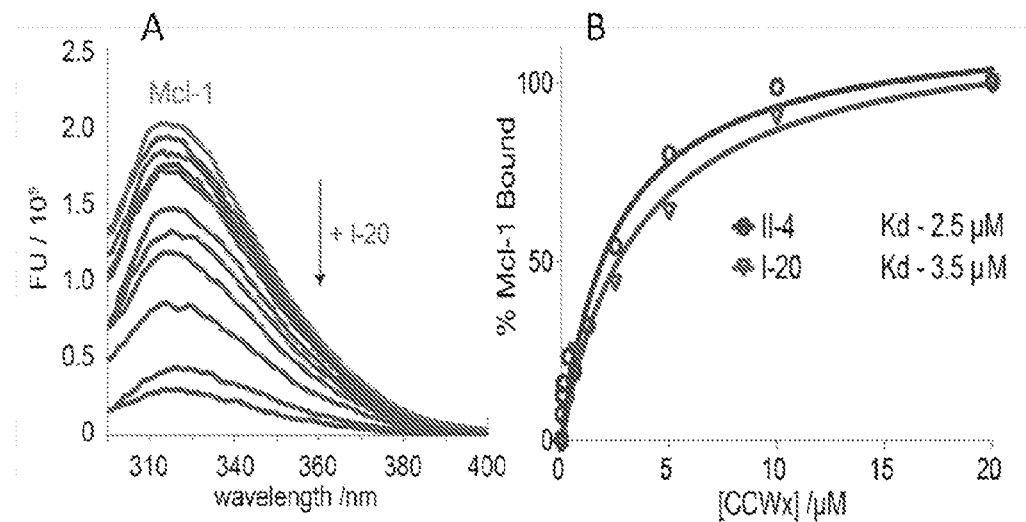
FIG. 5 displays that compounds II-4 and I-20 directly bind to Mcl-1 as measured by fluorescence quenching.

To investigate direct binding of compounds to Mcl-1, a fluorescence-quenching (FQ) assay based on the intrinsic Trp fluorescence of Mcl-1 was established. Using this assay, direct binding of several marinopyrrole analogues to Mcl-1 was confirmed by generating binding isotherms and calculating the binding constants for II-4 and I-20 (K$_d$: 2.5 and 3.5 μM, respectively, FIG. 5).

Structural Studies Confirm Binding of Marinopyrrole Compounds to the BH3-Binding Site of Mcl-1.

Figure 6:
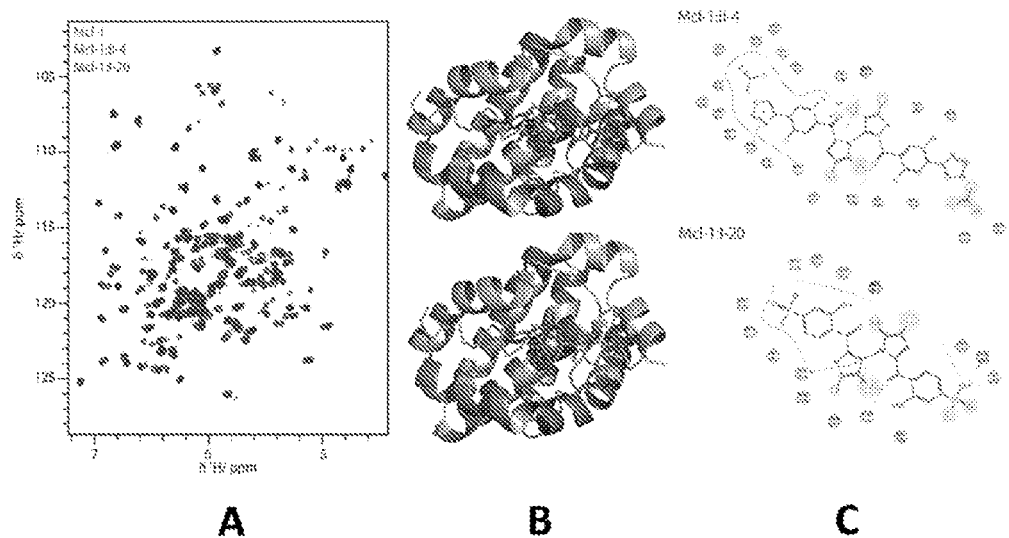
FIG. 6 (A) displays the overlaid $^1$H-$^{15}$N HSQC spectra of Mcl-1, $^{15}$N-Mcl-1:II-4 and of $^{15}$N-Mcl-1:I-20 at 1:1 stoichiometric ratio.

Structural characterization of 1-20 and II-4 was performed using NMR. HSQC spectra were collected at different ratios of compound:Mcl-1. NMR studies confirmed binding to Mcl-1 of 1-20 and 11-4, which show fast to intermediate exchange regime in agreement with the low M binding affinity as determined by FQ. In FIG. 6, comparison of the Mcl-1 HSQC spectra with and without compound demonstrates significant chemical shift changes particularly in residues of the BH3-binding site of Mcl-1 structure. The residues that undergo chemical shift changes upon compounds' binding onto the structure of Mcl-1 and the compounds' binding location were mapped (FIG. 6). An induced fit molecular docking approach guided by the NMR chemical shifts was used to determine the structural models of the compounds bound to Mcl-1 using Glide software (Schrodinger; FIG. 6). Structural details of the lowest energy structures suggest that compounds II-4 and 1-20 complement the BH3-binding site using an extended conformation and making several hydrophobic contacts with the hydrophobic groove of Mcl-1 site. Moreover, the marinopyrrole C=O group consistently interacts through hydrogen bonding with Arg263 and Thr266; two critical residues for the binding of the BH3 domain to Mcl-1.

Further Studies Assessing 1-2.

Figure 7:
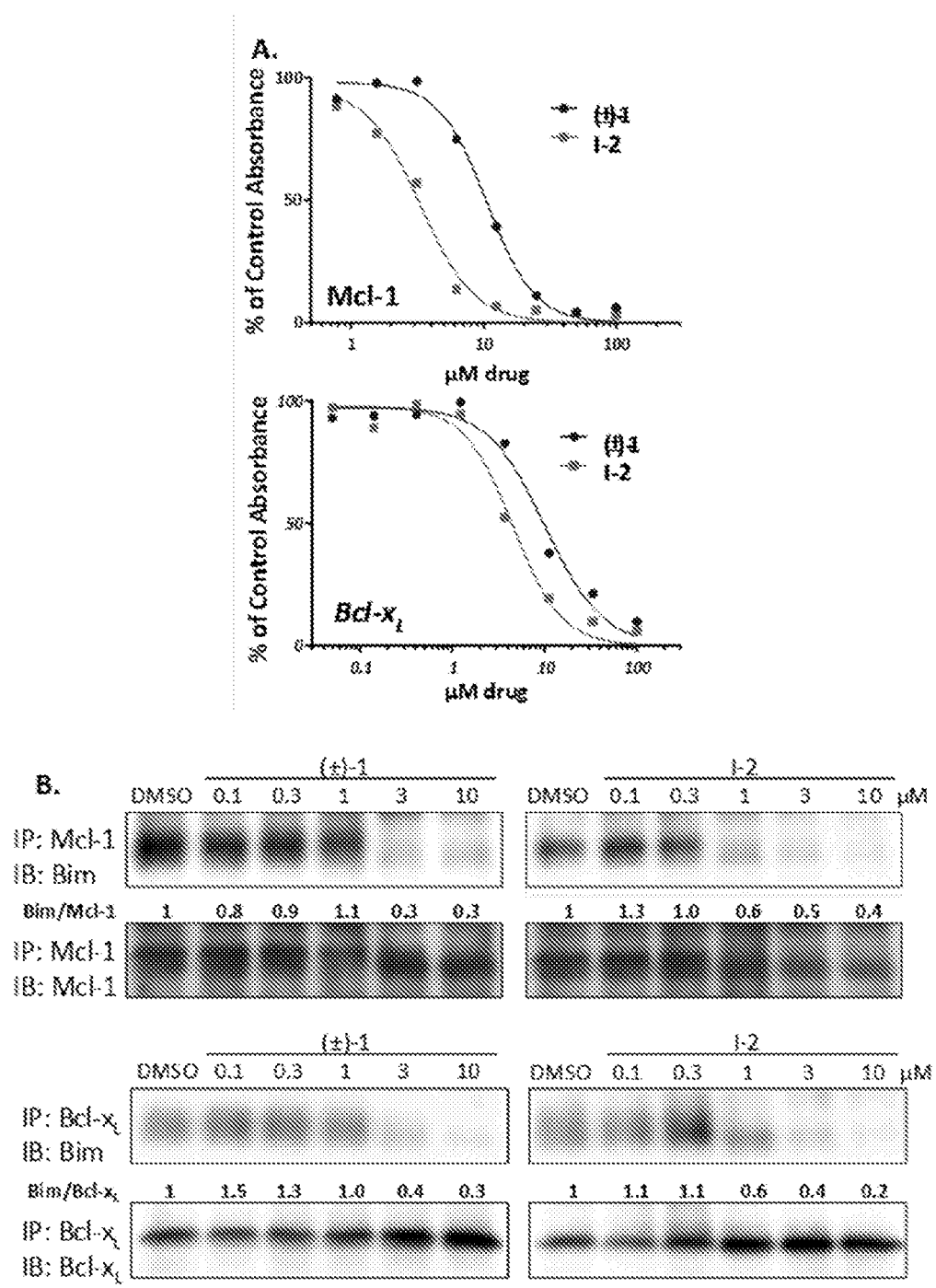
FIG. 7 displays Mcl-1/Bim and Bcl-xL/Bim ELISA assays (A). (B) shows results from coimmunoprecipitation and densiometry quantitation of of Bim/Mcl-1 and Mim/Bcl-xL in MDA-MB-468 cells treated with 1 and I-2 and the lysates.
Figure 8:
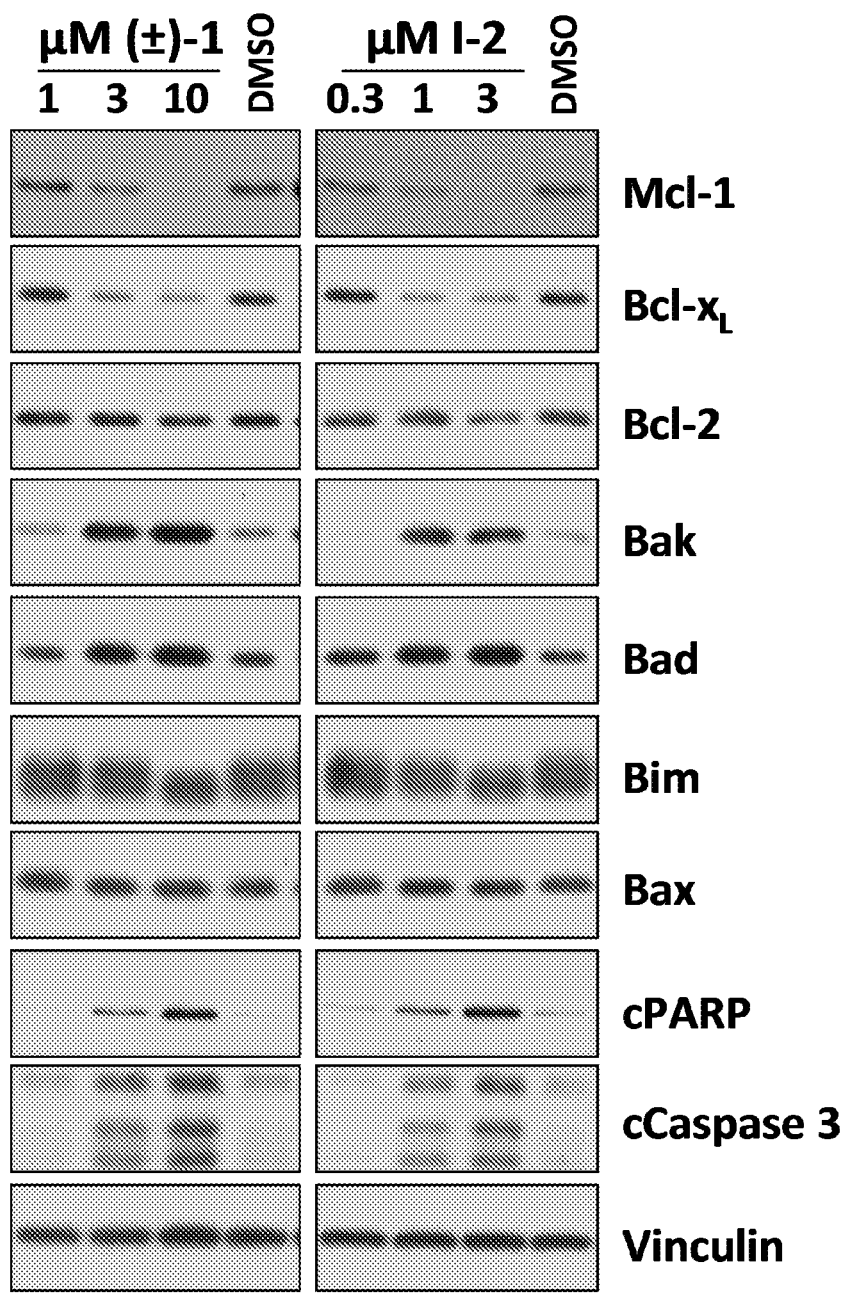
FIG. 8 displays the western blots after MDA-MB-468 cells were treated with 1 and I-2 and processed.

The above ELISA, GST-pull down, FQ and NMR in vitro studies demonstrated physical binding and rich SAR of the marinopyrrole derivatives. Subsequent intact cell studies demonstrated that some analogues such as I-2, I-3, I-5, IV-5, IV-6, IV-7, IV-8, V-4, VI-11 and VI-12 induced apoptosis in cultured human cancer cells. Among the most potent of these was I-2. I-2 is more potent than 1 at inhibiting the binding of Mcl-1 and Bcl-xL to Bim not only in vitro as demonstrated by ELISA (FIG. 7A) but also in MDA-MB-468 cancer cells by co-immunoprecipitation and densitometry quantitation of Bim/Mcl-1 and Bim/Bcl-xL levels (FIG. 7B). Previously, it has been shown that 1 decreases Mcl-1 levels, and here it was shown that I-2 was also more potent than 1 at decreasing the levels of Mcl-1 and Bcl-xL and at increasing the levels of the pro-apoptotic proteins Bak and Bad (FIG. 8). I-2 slightly decreased Bim but had little effects on Bcl-2 and Bax (FIG. 8). Consistent with these effects on the Bcl-2 family of proteins, I-2 was also more potent than 1 at inducing apoptosis (Caspase 3 and PARP cleavage) (FIG. 8) and at inhibiting anchorage-dependent (MTT assay) and -independent (soft agar assay) proliferation in both MDA-MB-468 and A-549 human lung cancer cells (FIGS. 9A and 9B).

Next, it was determined if I-2 is effective at inhibiting the growth of A-549 xenografts in nude mice (A-549 cells grew much better in nude mice than MDA-MB-468 cells. FIG. 10A shows that the tumor volumes from day 1 to day 14 in the vehicle-treated mice increased by an average of 160±10% whereas those from I-2-treated mice increased by only 45±30%. Treatment with vehicle and I-2 had little effect on the body weights of the mice (FIG. 10B).

Previously, it has been shown that the K562 leukemia cells that over-express Mcl-1 are more sensitive than the parental cells as well as to those that overexpress Bcl-xL and Bcl-2. However, more recently, it has also been shown that marinopyrrole A is not Mcl-1 selective. Herein, it was shown that parental MDA-MB-468 cells and the corresponding isogenic cell lines that over express Bim along with either Mcl-1, Bcl-xL or Bcl-2 are equally sensitive to I-2 ($IC_{50}$ values 0.3 to 0.4 µM) or 1 ($IC_{50}$ values 1.7 to 2.4 µM). The reason for this inconsistency is not known, but could be due to the different cell lines used.

Figure 11:
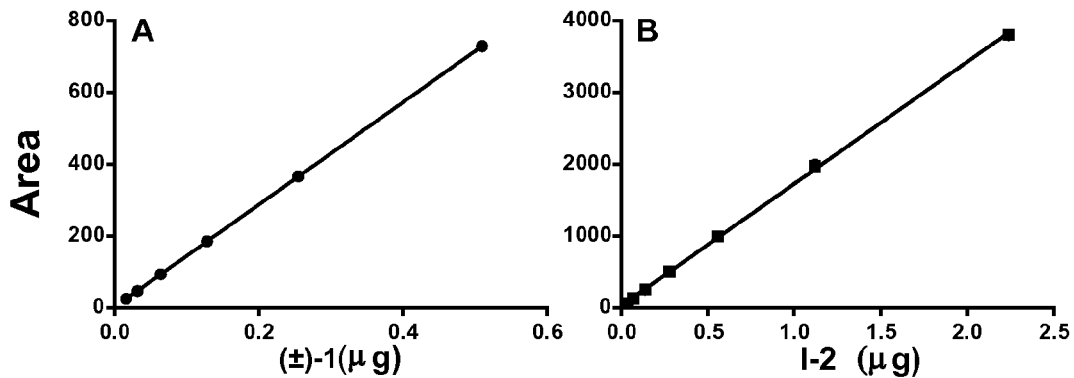
FIG. 11 displays standard curves for (A) (±)-1 and (B) I-2 as increasing amounts of (±)-1 and I-2 were mixed with mouse blood, extracted with methanol, and injected into LC-MS using Agilent 1220 Infinity LC/6120 Quadrupole LC/MS with Agilent Zorbax, SBC18 column.

In addition, a liquid chromatography mass spectrometry (LC-MS) method was developed. The optimized method consists of mixing of 1 and I-2 with mouse blood, extracting the drugs with methanol, and injecting the extracted 1 and I-2 into LC-MS using Agilent 1220 Infinity LC/6120 Quadrupole LC/MS with Agilent Zorbax, SBC18 column. FIG. 11 shows the resulting standard curves for 1 and I-2.

Figure 12:
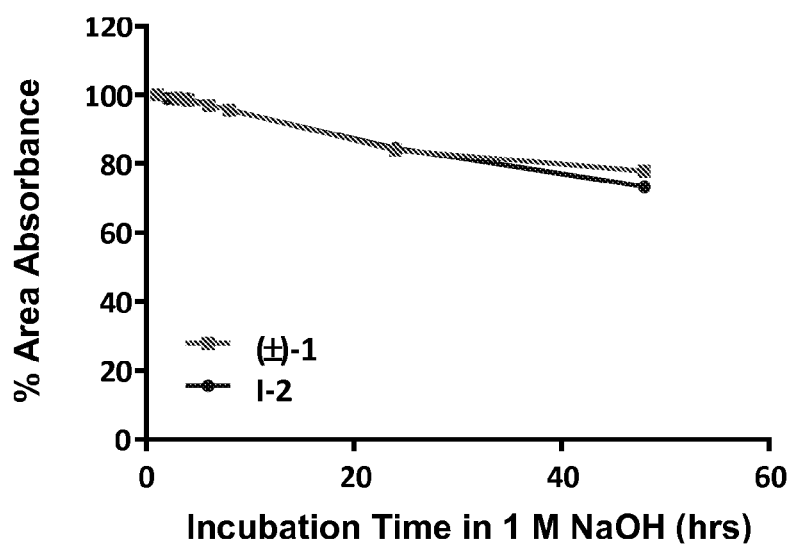
FIG. 12 displays the % area absorbance as (±)-1 and I-2 were incubated in 1 M NaOH for 1, 2, 4, 8, 24, and 48 hours at room temperature.

Furthermore, incubation of 1 and I-2 in 1 M NaOH for 1, 2, 4, 8, 24 and 48 hours at room temperature followed by HPLC analysis as described above demonstrated that 1 and I-2 were highly stable. Indeed, up to 8 hour incubation resulted in less than 2% loss, and even after 48 hours of exposure to 1 M NaOH, 76% and 81% of 1 and I-2, respectively, remained intact (FIG. 12).

The compounds and methods of the appended claims are not limited in scope by the specific compounds and methods described herein, which are intended as illustrations of a few aspects of the claims and any compounds and methods that are functionally equivalent are within the scope of this disclosure. Various modifications of the compounds and methods in addition to those shown and described herein are intended to fall within the scope of the appended claims. Further, while only certain representative compounds, methods, and aspects of these compounds and methods are specifically described, other compounds and methods and combinations of various features of the compounds and methods are intended to fall within the scope of the appended claims, even if not specifically recited. Thus a combination of steps, elements, components, or constituents can be explicitly mentioned herein; however, all other combinations of steps, elements, components, and constituents are included, even though not explicitly stated.

What is claimed is:

1. A compound of the following structure:

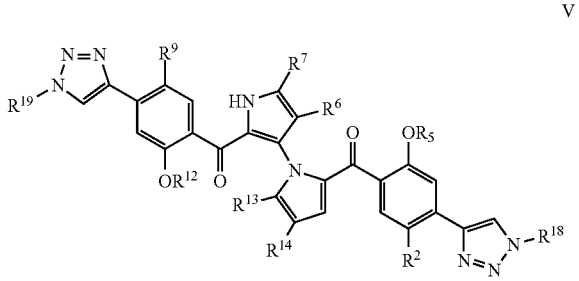

V wherein each $R^6$, $R^7$, $R^{13}$, and $R^{14}$ are independently chosen from hydrogen, halogen, and hydroxyl;
$R^5$ and $R^{12}$ are independently chosen from hydrogen, halogen, and substituted or unsubstituted alkyl;
$R^2$, $R^9$, $R^{18}$ and $R^{19}$ are independently chosen from hydrogen, halogen, hydroxyl, cyano, nitro, substituted or unsubstituted sulfonate, substituted or unsubstituted phosphonate, substituted or unsubstituted amino, substituted or unsubstituted alkyl, substituted or unsubstituted cycloalkyl, substituted or unsubstituted heteroalkyl, substituted or unsubstituted heterocycloalkyl, substituted or unsubstituted alkenyl, substituted or unsubstituted cycloalkenyl, substituted or unsubstituted heteroalkenyl, substituted or unsubstituted heterocycloalkenyl, substituted or unsubstituted alkynyl, substituted or unsubstituted heteroalkynyl, substituted or unsubstituted aryl, substituted or unsubstituted heteroaryl, substituted or unsubstituted alkoxyl, substituted or unsubstituted aryloxyl, and substituted or unsubstituted carboxyl;
or pharmaceutically acceptable salts thereof.

2. The compound of claim 1, wherein $R^6$, $R^7$, $R^{13}$ and $R^{14}$ are each independently chosen from F, Cl, Br, and I.

3. The compound of claim 1, wherein $R^6$, $R^7$, $R^{13}$ and $R^{14}$ are each Cl.

4. The compound of claim 1, wherein $R^5$ and $R^{12}$ are each H.

5. The compound of claim 1, having Formula B:

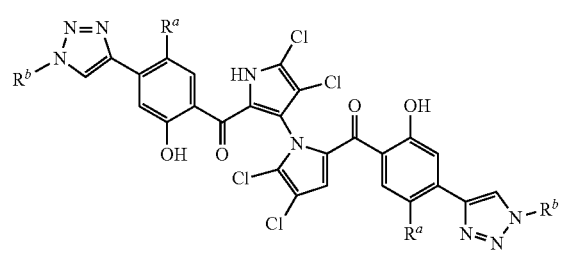

B wherein $R^a$ and $R^b$ are independently chosen from hydrogen, halogen, hydroxyl, cyano, nitro, substituted or unsubstituted sulfonate, substituted or unsubstituted phosphonate, substituted or unsubstituted amino, substituted or unsubstituted alkyl, substituted or unsubstituted cycloalkyl, substituted or unsubstituted heteroalkyl, substituted or unsubstituted heterocycloalkyl, substituted or unsubstituted alkenyl, substituted or unsubstituted cycloalkenyl, substituted or unsubstituted heteroalkenyl, substituted or unsubstituted heterocycloalkenyl, substituted or unsubstituted alkynyl, substituted or unsubstituted heteroalkynyl, substituted or unsubstituted aryl, substituted or unsubstituted heteroaryl, substituted or unsubstituted alkoxyl, substituted or unsubstituted aryloxyl, and substituted or unsubstituted carboxyl;

or pharmaceutically acceptable salts thereof.

6. The compound of claim 5, wherein $R^a$ is chosen from hydrogen and halogen.

7. The compound of claim 5, $R^a$ is chosen from hydrogen and Cl.

8. The compound of claim 5, wherein $R^b$ is chosen from substituted or unsubstituted alkyl, substituted or unsubstituted cycloalkyl, substituted or unsubstituted aryl, and substituted or unsubstituted carboxyl.

9. The compound of claim 5, wherein $R^b$ is chosen from $CH_2CO_2CH_2CH_3$, $CH_2CO_2Bu$, $CH_2CO_2H$, $CH_2Ph$, Ph, cyclohexane, and n-octane.

10. The compound of claim 5, Formula B-1:

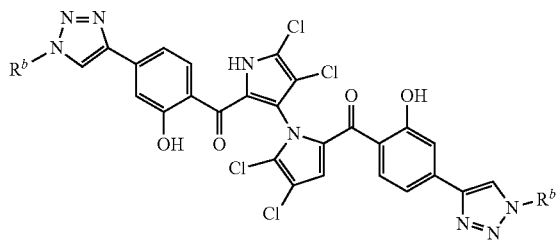

B-1 wherein $R^b$ is selected from substituted or unsubstituted alkyl, substituted or unsubstituted cycloalkyl, substituted or unsubstituted aryl, and substituted or unsubstituted carboxyl;

or pharmaceutically acceptable salts thereof.

11. The compound of claim 10, wherein $R^b$ is chosen from $CH_2CO_2CH_2CH_3$, $CH_2CO_2Bu$, $CH_2CO_2H$, $CH_2Ph$, Ph, cyclohexane, and n-octane.

12. The compound of claim 5, having Formula B-2:

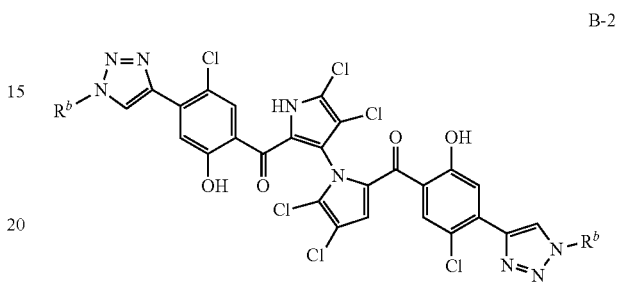

B-2 wherein $R^b$ is chosen from substituted or unsubstituted alkyl, substituted or unsubstituted cycloalkyl, substituted or unsubstituted aryl, and substituted or unsubstituted carboxyl;

or pharmaceutically acceptable salts thereof.

13. The compound of claim 12, wherein $R^b$ is chosen from $CH_2CO_2CH_2CH_3$, $CH_2CO_2Bu$, $CH_2CO_2H$, $CH_2Ph$, Ph, cyclohexane, and n-octane.

14. The compound of claim 5, the compound being selected from the group consisting of:

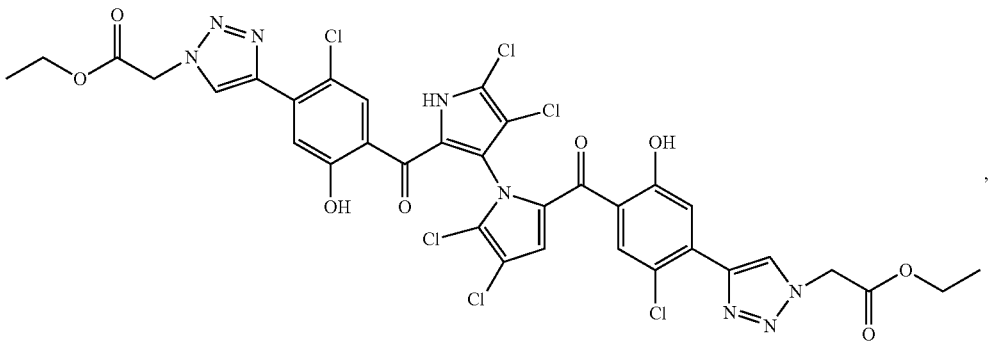

B-3

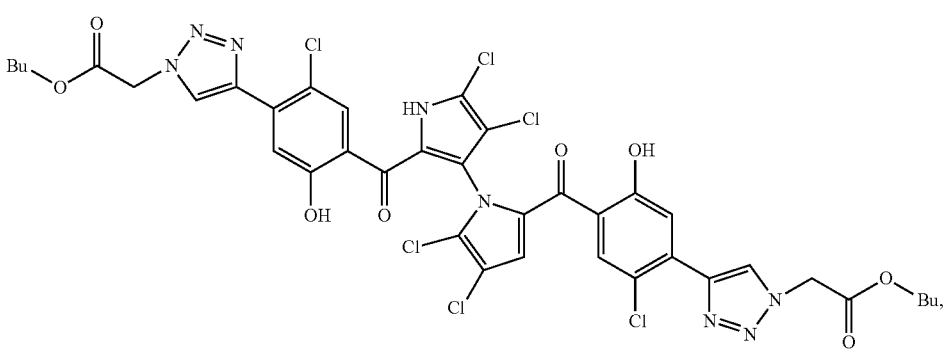

B-4

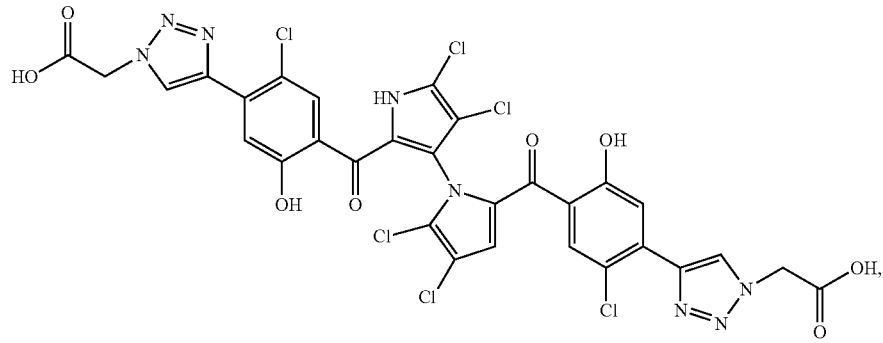
B-5
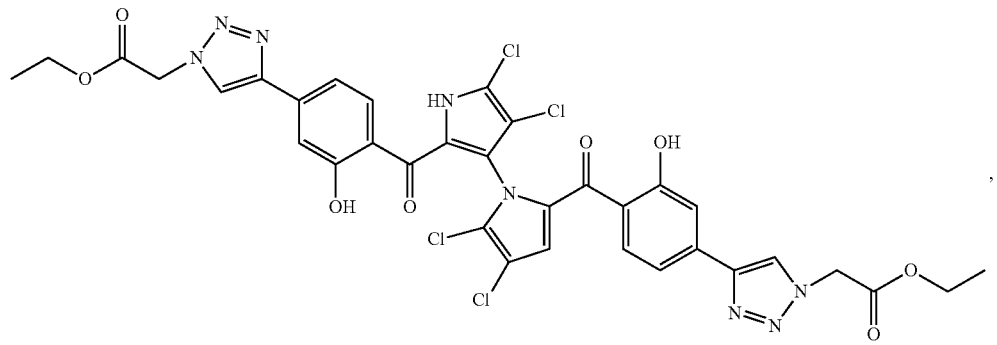
B-6
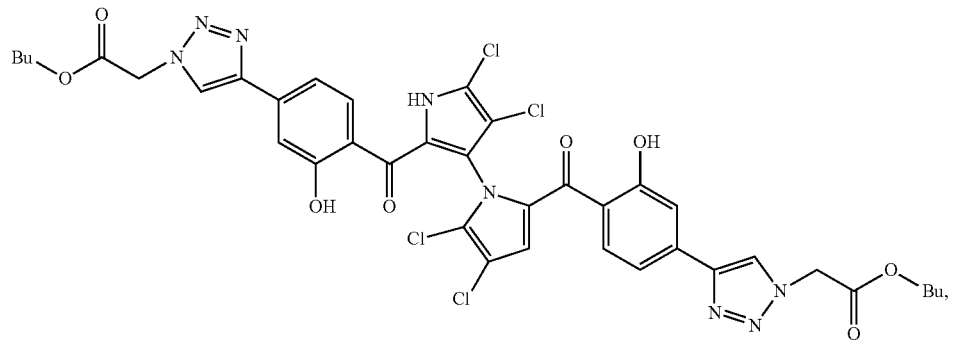
B-7
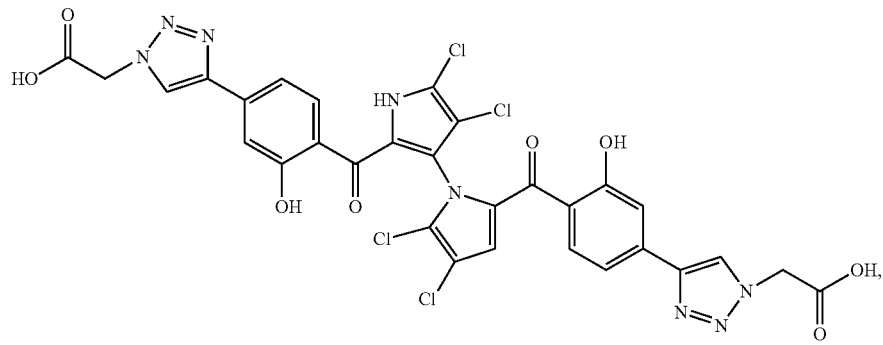
B-8

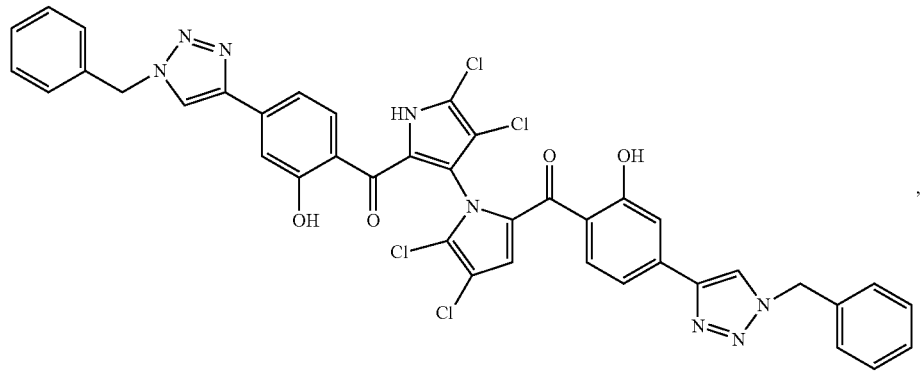

B-9

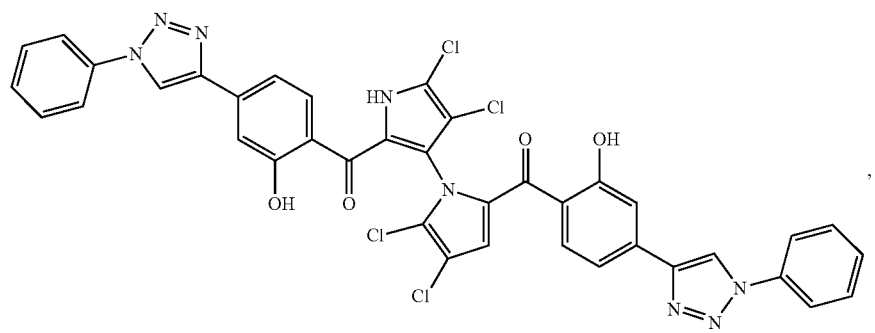

B-10

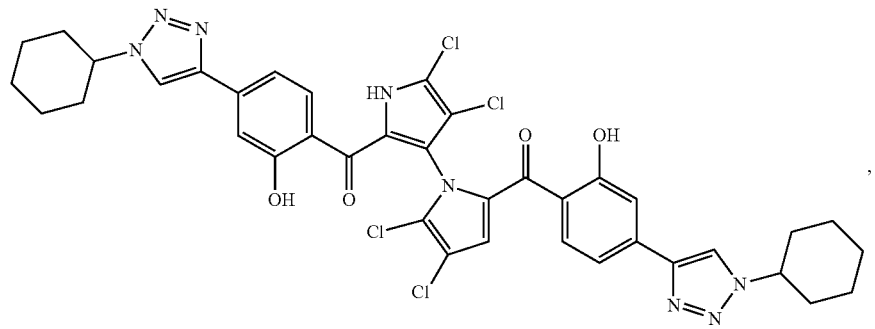

B-11

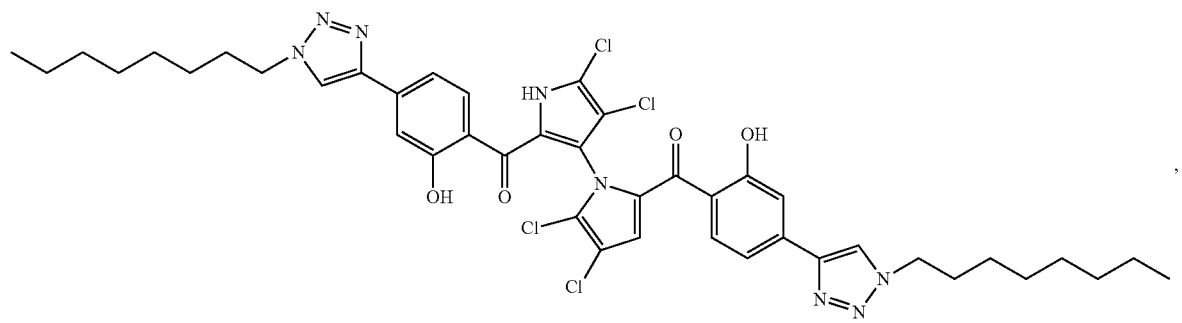

B-12 and pharmaceutically acceptable salts thereof.

15. The compound of claim 14, wherein the compound is a compound having Formula B-5 or Formula B-7 and wherein the butyl group comprises a tert-butyl group.

16. A method of treating cancer in a subject, comprising administering to the subject an effective amount of a compound of claim 1.

17. The method of claim 16, wherein the cancer is selected from the group consisting of bladder cancer, brain cancer, breast cancer, colorectal cancer, cervical cancer, gastrointestinal cancer, genitourinary cancer, head and neck cancer, lung cancer, ovarian cancer, pancreatic cancer, prostate cancer, renal cancer, skin cancer, and testicular cancer.

18. A method of killing a tumor cell in a subject, comprising: contacting the tumor cell with an effective amount of a compound of claim 1.

19. The method of claim 18, wherein the tumor cell is a Mcl-1 dependent cell.

20. The method of claim 18, further comprising irradiating the tumor cell with an effective amount of ionizing radiation.

\* \* \* \* \*